(12) United States Patent
Harrop et al.

(10) Patent No.: US 8,133,681 B2
(45) Date of Patent: Mar. 13, 2012

(54) CHEMO-IMMUNOTHERAPY METHOD

(75) Inventors: Richard Harrop, Newbury (GB);
Michelle Kelleher, Oxford (GB);
William Shingler, Oxford (GB); Susan Mary Kingsman, Oxford (GB); Miles William Carroll, Oxon (GB)

(73) Assignee: Oxford Biomedica (UK) Limited, Oxfordshire (GB)

( * ) Notice: Subject to any disclaimer, the term of this patent is extended or adjusted under 35 U.S.C. 154(b) by 0 days.

(21) Appl. No.: 12/052,710

(22) Filed: Mar. 20, 2008

(65) Prior Publication Data

US 2009/0047307 A1    Feb. 19, 2009

Related U.S. Application Data

(63) Continuation of application No. PCT/GB2006/003507, filed on Sep. 21, 2006.

(30) Foreign Application Priority Data

Sep. 21, 2005 (GB) .................................. 0519303.2

(51) Int. Cl.
*G01N 33/53* (2006.01)
*A61K 39/385* (2006.01)
(52) U.S. Cl. ..................................... 435/7.1; 424/193.1
(58) Field of Classification Search .................... None
See application file for complete search history.

(56) References Cited

U.S. PATENT DOCUMENTS

2010/0226931 A1* 9/2010 Valiante et al. ............ 424/184.1

FOREIGN PATENT DOCUMENTS

| WO | WO00/29428 | | 5/2000 |
|----|------------|---|--------|
| WO | WO 00/29428 | * | 5/2000 |
| WO | WO01/36486 | | 5/2001 |
| WO | WO02/38612 | | 5/2002 |
| WO | WO03/080111 | | 10/2003 |
| WO | WO03/082212 | | 10/2003 |
| WO | WO03/094846 | | 11/2003 |
| WO | WO2004/026337 | | 4/2004 |
| WO | WO2005/043155 | | 5/2005 |
| WO | WO2005/065718 | | 7/2005 |
| WO | WO2006/015882 | | 2/2006 |

OTHER PUBLICATIONS

Mulryan et al (Molecular Cancer Therapeutics, Oct. 2002, 1: 1129-1137).*
Ghiringhelli et al (Eur J Immunol, Feb. 2004, 34:336-344).*
Goldberg et al (Journal of Clinical Oncology, 2004, 22(1): 23-30).*
Danull et al (Proceedings of the American Association for Cancer Research, 2003, 44(2nd), #3840).*
Wolf et al (Clin Cancer Res, 2003, 9(2): 806-821).*
Griffiths et al (British Journal of Cancer, Sep. 13, 2005, 93: 670-677).*
Barnett et al., "Regulatory T cells in ovarian cancer: Biology and therapeutic potential," *Amer. J. Reproduc. Immunol.*, 54(6):369-377, 2005.
Casares et al., "CD4+/CD25+ regulatory cells inhibit activation of tumor-primed CD4+ T cells with IFN-gamma-dependent antiangiogenic activity, as well as long-lasting tumor immunity elicited by peptide vaccination" *J. Immunol.* 171(11):5931-5939, 2003.
Correale et al., "Chemo-Immunotherapy of metastatic colorectal carcinoma with gemcitabine plus FOLFOX 4 followed by subcutaneous granulocyte macrophage coloney-stimulating factor and interleukin-2 induces strong immunogenic and antitumor activity in metastatic colon cancer patients," *J. Clin. Oncol.*, 23(35):8950-8958, 2005.
Dannull et al., "Enhancement of T-cell responses against renal cell carcinoma by elimination of regulatory T cells," *Proc. Amer. Assoc. Cancer Res. Annual Meeting*, 44:765, 2003.
Dannull et al., "Enhancement of vaccine-mediated antitumor immunity in cancer patients after depletion of regulatory T cells," *J. Clin. Invest.*, 115(12):3623-3633, 2005.
Drury et al., "Phase II studies of MVA Expressing the Tumour Antigen 5T4 Given With 5-FU Based Chemotherapies: Safety Immunogenicity and Clinical Respnoses" *Immunol.*, 116 (1):34, 2005.
International Search Report for PCT/GB2006/003507, Jun. 14, 2007.
Lutsiak et al., "Inhibition of CD4<+>25<+> T regulatory cell function implicated in the enhanced immune response by low-dose cyclophosphamid," *Blood*, 105(7):2862-2868, Apr. 1, 2005.
Powell et al., "Large-scale depletion of CD25+ regulatory T cells from patient Leukapheresis samples," *J. Immunother.*, 28(4):1067-5583, 2005.
Sakaguchi, "Naturaly arising CD4+ regulatory T cells for immunologic self-tolerance and negative control of immune responses," *Ann. Rev. Immunol.* 22:531-562, 2004.
Sutmuller et al., "Synergism of Cytotoxic T Lymphocyte-Associated Antigen 4 Blockade and Depletion of CD25+ regulatory T cells in antitumor therapy reveals alternative pathways for suppression of autoreactive cytotoxic T lymphocyte responses," *J. Exp. Med.*, 194(6):823-832, 2001.
Zou, "Regulatory T cells, tumour immunity and immunotherapy," *Nature Rev. Immunol.*, 6(4):295-307, 2006.

* cited by examiner

*Primary Examiner* — Sean Aeder
(74) *Attorney, Agent, or Firm* — Marshall, Gerstein & Borun LLP

(57) ABSTRACT

A method of treating or preventing disease, said method comprising administering to a subject, simultaneously, sequentially or separately, an antigen and a chemotherapeutic agent or agents comprising the steps of: administering the chemotherapeutic agent or agents, and administering an antigen up to 6 weeks after the chemotherapeutic agent.

5 Claims, 6 Drawing Sheets

Figure 1:
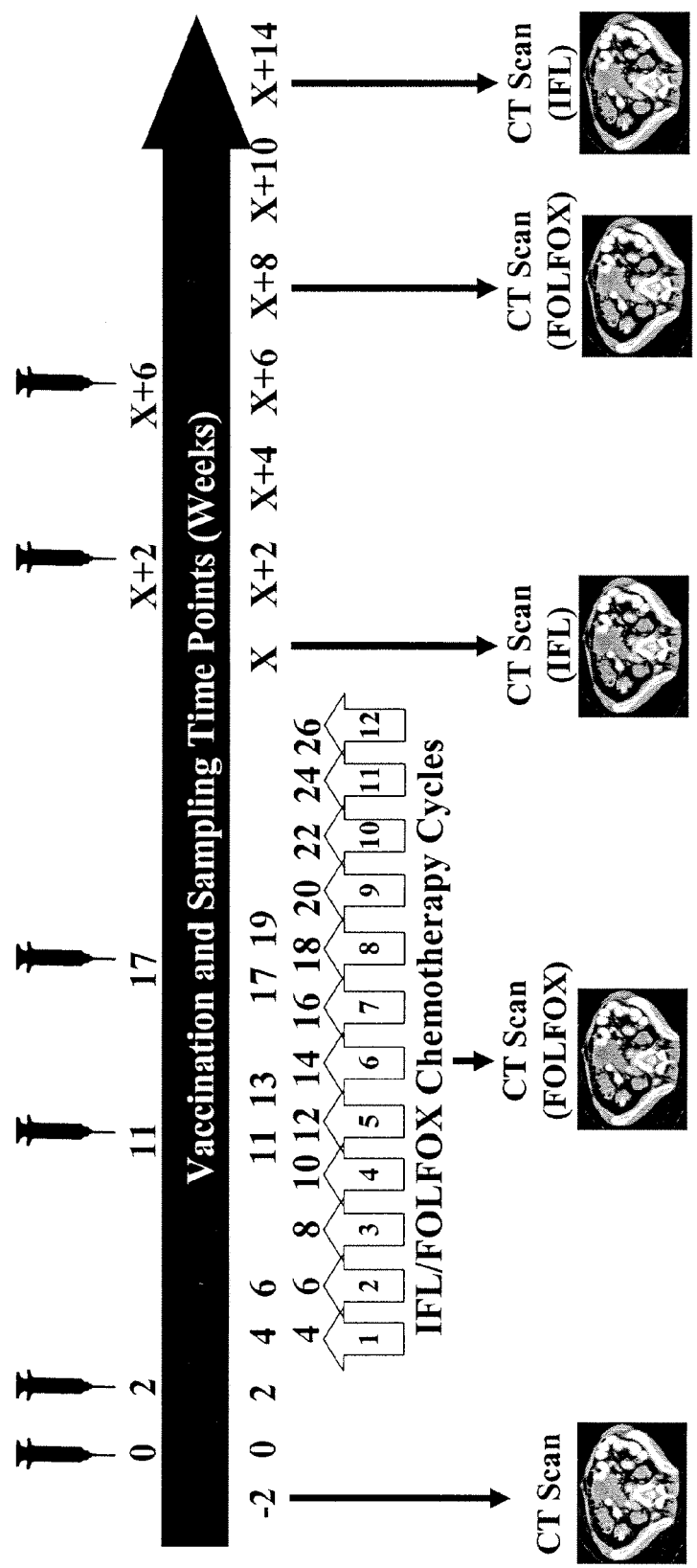

Fig 4A: 5T4 Responses in TV2-IFL
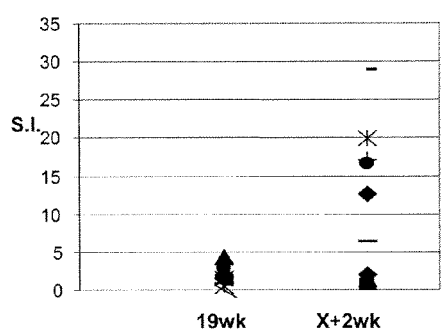
Fig 4B: 5T4 Responses in TV2-FOLFOX
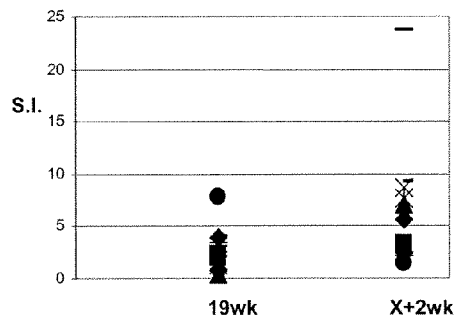
Fig 4C: MVA Responses in TV2-IFL
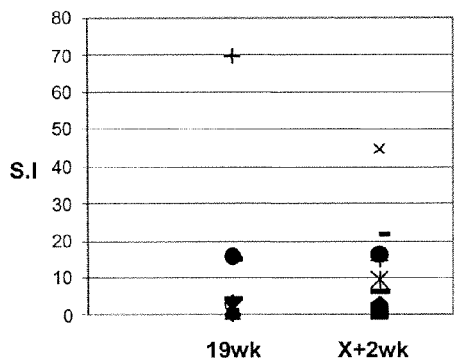
Fig 4D: MVA Responses in TV2
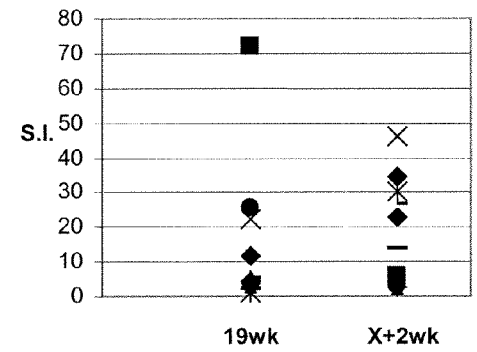
Fig 4E: TT Responses in TV2-IFL
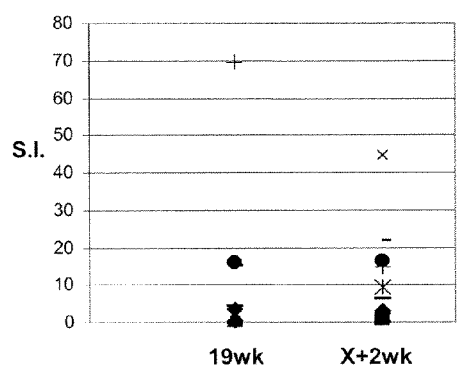
Fig 4F: TT Responses in TV2-FOLFOX
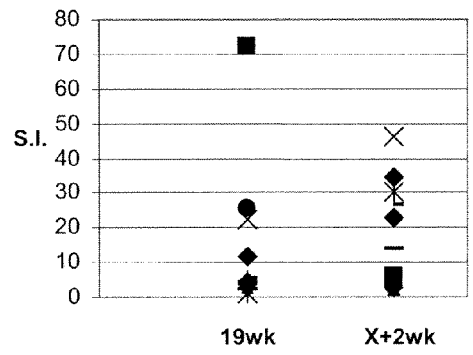
Figure 4A-F

Figure 6A-C

# CHEMO-IMMUNOTHERAPY METHOD

This application is a continuation of International Application No. PCT/GB2006/003507 filed Sep. 21, 2006, incorporated here by reference, which claims priority benefit of Great Britain Patent Application No. 0519303.2 filed Sep. 21, 2005.

FIELD OF THE INVENTION

The present invention relates to a combination therapy for treating an individual with an antigen to elicit an antigen-specific immune response along with treating that individual with a chemotherapeutic agent.

BACKGROUND TO THE INVENTION

Treatment of patients with advanced cancers is generally by chemotherapy. However, for solid tumours, in particular, it is rarely curative and additional routes of therapy are required.

Recently progress in human immunobiotechnology has opened up the field of immunotherapy as a new approach to cancer treatment. Specific immunization against a target antigen has been achieved in some patients with a number of different anticancer vaccines, but improved long term responses are desirable.

Accordingly, there remains a need for improved therapy regimes.

As chemotherapy has a number of observed detrimental effects on the immune system, chemotherapy and immunotherapy are regarded as unrelated or, more commonly, antagonistic forms of therapy. This is because, most chemotherapies kill target cells by apoptosis and this mode of cell death has been regarded immunologically as either non-stimulatory or able to produce immune tolerance—a state where T cells can no longer respond to the presented antigen by mounting an immune response. In addition, a common side effect of chemotherapies is the induction of lymphopaenia i.e. a reduction in lymphocytes and this is assumed to be detrimental to any potential immune response.

SUMMARY OF THE INVENTION

The present invention relates to a combination treatment comprising administering an antigen, to elicit an immune response specific to that antigen, as well as a chemotherapeutic agent or agents. In particular, the present invention is based on the surprising finding that treatment to stimulate an immune response against an antigen by administering an antigen is enhanced by treatment with a chemotherapeutic agent or agents.

Accordingly, in a first aspect of the invention, there is provided a pharmaceutical composition comprising an antigen and a chemotherapeutic agent or agents and a pharmaceutically acceptable carrier, diluent or excipient.

Suitably, such a composition is provided as the two components for separate, simultaneous or subsequent administration in a form such as a kit.

Suitably, the antigen is an antigen to which it would be desirable to elicit an immune response. Such antigens include, for example, inactivated, attenuated or nonpathogenic strains of pathogens which are used as antigens to induce immunity against diseases caused by pathogens such as typhoid, polio, measles, mumps, rubella and tuberculosis, allergenic proteins from pollen and other allergenic material which are isolated and used to immunise a patient, antigenic components of pathogenic organisms such as *Haemophilus influenza* B, Hepatitis B and so forth.

In another embodiment, the antigen may be one which can be used in a method for contraceptive such as a method for inducing an immune response which is generated a sperm or egg specific protein. For example, the antigen may be a zona pellucida protein.

In one embodiment, the antigen is a tumor associated antigen. A suitable tumour associated antigen (TAAs) includes 5T4. Other suitable antigens include TAAs in the following classes: cancer testis antigens (e.g. HOM-MEL-40), differentiation antigens (e.g. HOM-MEL-55), overexpressed gene products (HOM-MD-21), mutated gene products (NY-COL-2), splice variants (HOM-MD-397), gene amplification products (HOM-NSCLC-11) and cancer related autoantigens (HOM-MEL-2.4) as reviewed in Cancer Vaccines and Immunotherapy (2000) Eds Stern, Beverley and Carroll, Cambridge University Press, Cambridge. Further examples include, MART-1 (Melanoma Antigen Recognised by T cells-1) MAGE-A (MAGE-A1, MAGE-A2, MAGE-A3, MAGE-A4, MAGE-A6, MAGE-A8, MAGE-A10, MAGE-A12), MAGE B (MAGE-B1-MAGE-B24), MAGE-C (MAGE-C1/CT7, CT10), GAGE (GAGE-1, GAGE-8, PAGE-1, PAGE-4, XAGE-1, XAGE-3), LAGE (LAGE-1a (1S), -1b(1L), NY-ESO-1), SSX (SSX1-SSX-5), BAGE, SCP-1, PRAME (MAPE), SART-1, SART-3, CTp11, TSP50, CT9/BRDT, gp100, MART-1, TRP-1, TRP-2, MELAN-A/MART-1, Carcinoembryonic antigen (CEA), prostate-specific antigen (PSA), MUCIN (MUC-1) and Tyrosinase. TAAs are reviewed in Cancer Immunology (2001) Kluwer Academic Publishers, The Netherlands. Additional tumour associated antigens include Her 2, survivin and TERT.

By "antigen" is included a means for providing an antigen protein or peptide to be introduced into an individual. As described herein, an antigen may be provided through delivering a peptide or protein or through delivering a nucleic acid encoding a peptide or protein.

By "antigen" in the context of the present invention it is also meant to incorporate an antigenic peptide derived from an antigen. In particular, "tumour associated antigen" is intended to encompass a peptide derived from a tumour associated antigen.

An antigen such as a tumour associated antigen can be provided for use as a medicament in a number of different ways. It can be administered as part of a viral vector. A number of suitable viral vectors will be familiar to those skilled in the art and include a number of vectors described herein.

The TroVax® vaccine (TroVax is a registered US, and European Community trade mark of Oxford Biomedica plc) comprises a viral vector derived from MVA which has been modified to express the tumour associated antigen, 5T4. In one embodiment the tumour antigen for use in the combination of the invention is 5T4 and is provided by the TroVax® vaccine.

Suitable chemotherapeutic agents include any conventional agents. In one embodiment, the chemotherapeutic agent is selected from irinotecan, fluorouracil, leucovorin, and oxaliplatin. In another embodiment a "chemotherapeutic agent" can include a combination of chemotherapeutic agents in a therapy such as FOLFOX or IFL.

In another aspect there is provided a use of a composition according to the present invention in the manufacture of a medicament for the treatment of a disease. Suitably, where the antigen is a tumour associated antigen, the disease is cancer.

In a further aspect there is provided a pharmaceutical product comprising an antigen and a chemotherapeutic agent or agents for simultaneous, sequential or separate use in therapy. Suitably the antigen is a tumour associated antigen.

By "simultaneous" is meant that two agents are administered concurrently. By "sequential" is meant that the two agents are administered one after the other within a time frame such that they are both available to act therapeutically within the same time frame. The optimum time interval between administering the two agents will vary depending on the precise nature of the method for delivering the tumour antigen.

The term "separate" is used to mean that the gap between the administration of the first agent and that of the second is substantial.

In one embodiment, chemotherapy is administered before administration of the antigen. Suitably, chemotherapy is administered 10 weeks before administration of the antigen, preferably less than 10 weeks and, more preferably in about 2 weeks before administration of antigen. In a preferred embodiment, chemotherapy is administered 2 weeks before administration of the antigen.

In one embodiment, the antigen is administered in advance of the beginning of chemotherapy and then again following chemotherapy. In another embodiment, the antigen is administered during chemotherapy as well as before and/or following chemotherapy.

In one embodiment, the antigen is administered at least 24 hours, preferably 48 hours after chemotherapy. Preferably, administration of the antigen takes place up to 8 weeks, preferably up to 6 weeks, even more preferred between 4 and 6 weeks after chemotherapy.

In one embodiment the antigen is administered when the subject to be treated has a reduced $CD4^+CD25^+$ Treg cell count or reduced $CD4^+CD25^+$ Treg cell function.

By "reduced $CD4^+CD25^+$ Treg cell count" is meant a $CD4^+CD25^+$ Treg cell count which is lower then the $CD4^+CD25^+$ Treg cell count determined prior to administering a $CD4^+CD25^+$ Treg cell count lowering agent, such as a chemotherapeutic agent or agents, or Ontak. Preferably the $CD4^+CD25^+$ Treg cell level is at least 15% 30%, 50%, 70%, 90% lower then the $CD4^+CD25^+$ Treg cell level determined prior to administering the $CD4^+CD25^+$ Treg cell count lowering agent (for example a chemotherapeutic agent or agents or Ontak), Most preferably, the vaccination will coincide with the period when the chemotherapy has caused a maximum depletion of $CD4^+CD25^+$ Treg cell.

By "reduced $CD4^+CD25^+$ Treg cell function" is meant a $CD4^+CD25^+$ Treg cell function which is lower then the $CD4^+CD25^+$ Treg cell function determined prior to administering a $CD4^+CD25^+$ Treg cell function lowering agent, such as a chemotherapeutic agent, or Ontak. Preferably the $CD4^+CD25^+$ Treg cell function is at least 15% 30%, 50%, 70%, 90% lower then the $CD4^+CD25^+$ Treg cell function determined prior to administering the $CD4^+CD25^+$ Treg cell function lowering agent (for example a chemotherapeutic agent or agents or Ontak), Most preferably, the vaccination will coincide with the period when the chemotherapy has caused a maximum reduction of $CD4^+CD25^+$ Treg cell function.

In one embodiment, there is provided a pharmaceutical product in accordance with the invention in the form of a pharmaceutical composition comprising a pharmaceutically acceptable carrier, diluent or excipient.

In another aspect there is provided a method of treating or preventing a disease, said method comprising administering to a subject simultaneously, sequentially or separately, an antigen and a chemotherapeutic agent.

Suitably, the method of treating an individual comprises the steps of:

a) administering chemotherapy
b) administering an antigen.

In one embodiment, the method further comprises administering an antigen prior to administering chemotherapy. In another embodiment, the method further comprises administering an antigen during the same time frame as administering chemotherapy.

In another aspect there is provided a method of treating cancer, said method comprising administering to a subject simultaneously, sequentially or separately, a tumour associated antigen and a chemotherapeutic agent.

Suitably, the method of treating an individual comprises the steps of a) administering a tumour antigen to elicit an antitumour response,
b) administering chemotherapy
c) administering a tumour antigen.

In one embodiment the method further comprises the step of determining the $CD4^+CD25^+$ Treg cell count or $CD4^+CD25^+$ Treg cell function. In another embodiment the method comprises determining the $CD4^+CD25^+$ Treg cell count or reduced $CD4^+CD25^+$ Treg cell function prior to and/or during and/or after chemotherapy.

In a further aspect there is provided a use of an antigen in the preparation of a medicament for use in the treatment or prevention of a disease wherein said treatment comprises administering to a subject simultaneously, sequentially or separately a chemotherapeutic agent or agents and an antigen.

In another aspect there is provided a use of an antigen and a chemotherapeutic agent or agents in the preparation of a medicament for use in the treatment or prevention of a disease.

In another aspect there is provided a use of an antigen in the preparation of a medicament for use in the treatment or prevention of a disease wherein said treatment is for use in combination therapy with a chemotherapeutic agent.

In another aspect there is provided a use of a chemotherapeutic agent or agents in the preparation of a medicament for use in the treatment or prevention of a disease wherein said treatment is for use in combination therapy with an antigen.

In a further aspect there is provided a use of an antigen and a chemotherapeutic agent or agents in the manufacture of a medicament for simultaneous, separate or sequential use in the treatment or prevention of a disease wherein the administration pattern comprises administering the antigen prior to administering chemotherapy and administering the antigen after chemotherapy.

In another aspect there is provided a use of an antigen in the preparation of a medicament for administering to a mammal so as to induce an immune response to an antigen wherein the administration of the antigen comprises administering the antigen prior to and/or during and/or after administration of a chemotherapeutic agent in the treatment or prevention of a disease.

Suitably, in one embodiment of any of the above aspects, the antigen is a tumour associated antigen and the disease is cancer.

In a further aspect of the invention, there is provided a method of enhancing an immune response to an antigen by treating with chemotherapy before and/or during and/or after sensitising to the antigen.

In another aspect there is provided a kit comprising a means for administering an antigen in combination with a chemotherapeutic agent or agents for administration.

Other aspects of the present invention are presented in the accompanying claims and in the following description and discussion. These aspects are presented under separate section headings. However, it is to be understood that the teachings under each section heading are not necessarily limited to that particular section heading.

DETAILED DESCRIPTION OF THE INVENTION

Antigens

Tumour associated antigens (TAAs)

TAAs have been characterised either as membrane proteins or altered carbohydrate molecules of glycoproteins and glycolipids, however their functions remain largely unknown. One TAA family, the transmembrane 4 superfamily (TM4SF), usually has four well-conserved membrane-spanning regions, certain cysteine residues and short sequence motifs. There is evidence that TM4SF antigens exist in close association with other important membrane receptors including CD4 and CD8 of T cells (Imai & Yoshie (1993) *J. Immunol.* 151, 6470-6481). It has also been suggested that TM4SF antigens may play a role in signal transduction which in turn, affects cell development, activation and motility. Examples of TM4SF antigens include human melanoma-associated antigen ME491, human and mouse leukocyte surface antigen CD37, and human lymphoblastic leukemia-associated TALLA-1 (Hotta, H. et al. (1988) Cancer Res. 48, 2955-2962; Classon, B. J. et al. (1989) J. Exp. Med. 169: 1497-1502; Tomlinson, M. G. et al. (1996) Mol. Immun. 33: 867-872; Takagi, S. et al. (1995) Int. J. Cancer 61: 706-715).

Further examples of TAAs also include, but are not limited to, TAAs in the following classes: cancer testis antigens (HOM-MEL-40), differentiation antigens (HOM-MEL-55), overexpressed gene products (HOM-MD-21), mutated gene products (NY-COL-2), splice variants (HOM-MD-397), gene amplification products (HOM-NSCLC-11) and cancer related autoantigens (HOM-MEL-2.4) as reviewed in Cancer Vaccines and Immunotherapy (2000) Eds Stern, Beverley and Carroll, Cambridge University Press, Cambridge. Further examples include, MART-1 (Melanoma Antigen Recognised by T cells-1) MAGE-A (MAGE-A1, MAGE-A2, MAGE-A3, MAGE-A4, MAGE-A6, MAGE-A8, MAGE-A10, MAGE-A12), MAGE B (MAGE-B1-MAGE-B24), MAGE-C (MAGE-C1/CT7, CT10), GAGE (GAGE-1, GAGE-8, PAGE-1, PAGE-4, XAGE-1, XAGE-3), LAGE (LAGE-1a (1S), -1b(1L), NY-ESO-1), SSX (SSX1-SSX-5), BAGE, SCP-1, PRAME (MAPE), SART-1, SART-3, CTp11, TSP50, CT9/BRDT, gp100, MART-1, TRP-1, TRP-2, MELAN-A/MART-1, Carcinoembryonic antigen (CEA), prostate-specific antigen (PSA), MUCIN (MUC-1) and Tyrosinase. TAAs are reviewed in Cancer Immunology (2001) Kluwer Academic Publishers, The Netherlands.

In one embodiment, the tumour associated antigen is 5T4.

5T4

5T4 has been previously characterised, for example, in WO89/07947. The sequence of human 5T4 appears in GenBank at accession no. Z29083. The 5T4 antigen may come from a different species, such as murine 5T4 (WO00/29428), canine 5T4 (WO01/36486) or feline 5T4. The antigen may also be derived from a naturally occurring variant of 5T4 found within a particular species, preferably a mammal. Such a variant may be encoded by a related gene of the same gene family, by an allelic variant of a particular gene, or represent an alternative splicing variant of the 5T4 gene. 5T4 and its use has also been described in EP1036091.

A peptide epitope derived from 5T4 from a different species or a splice variant may have a different amino acid sequence from the analogous human wild-type 5T4 peptide epitope. However, as long as the peptide retains the same qualitative binding specificity as the human peptide (i.e. it binds in the peptide binding groove of an MHC molecule of the same haplotype) then it is still an epitope in accordance with the present invention.

Immunogenic Peptides Derived from Antigens

"Antigens" include peptide epitopes derived from specific antigenic proteins including tumour associated antigens. Suitable epitopes include T cell epitopes. Suitably said peptides are "immunogenic peptides" i.e. they are capable of stimulating an anti-tumour associated antigen immune response. Such an immune response includes a cytotoxic T cell response for peptides as well as a cytotoxic T cell response and/or antibody response for protein antigens in general.

In this respect, the term "peptide" is used in the normal sense to mean a series of residues, typically L-amino acids, connected one to the other typically by peptide bonds between the α-amino and carboxyl groups of adjacent amino acids. The term includes modified peptides and synthetic peptide analogues.

A T cell epitope is a short peptide derivable from a protein antigen. Antigen presenting cells can internalise antigen and process it into short fragments which are capable of binding MHC molecules. The specificity of peptide binding to the MHC depends on specific interactions between the peptide and the peptide-binding groove of the particular MHC molecule.

Peptides which bind to MHC class I molecules (and are recognised by CD8+ T cells) are usually between 6 and 12, more usually between 8 and 12 amino or 8 and 10 amino acids in length. Typically, peptides are 9 amino acids in length. The amino-terminal amine group of the peptide makes contact with an invariant site at one end of the peptide groove, and the carboxylate group at the carboxy terminus binds to an invariant site at the other end of the groove. Thus, typically, such peptides have a hydrophobic or basic carboxy terminus and an absence of proline in the extreme amino terminus. The peptide lies in an extended conformation along the groove with further contacts between main-chain atoms and conserved amino acid side chains that line the groove. Variations in peptide length are accommodated by a kinking in the peptide backbone, often at proline or glycine residues.

Peptides which bind to MHC class II molecules are usually at least 10 amino acids, for example about 13-18 amino acids in length, and can be much longer. These peptides lie in an extended conformation along the MHC II peptide-binding groove which is open at both ends. The peptide is held in place mainly by main-chain atom contacts with conserved residues that line the peptide-binding groove.

Antigenic peptides of the present invention may be made using chemical methods (Peptide Chemistry, A practical Textbook. Mikos Bodansky, Springer-Verlag, Berlin.). For example, peptides can be synthesized by solid phase techniques (Roberge J Y et al (1995) Science 269: 202-204), cleaved from the resin, and purified by preparative high performance liquid chromatography (e.g., Creighton (1983) Proteins Structures And Molecular Principles, WH Freeman and Co, New York N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage from a longer polypeptide. For example, the peptide may be obtained by cleavage from a full-length protein such as full length 5T4. The composition of a peptide may be confirmed by amino acid analysis or sequencing (e.g., the Edman degradation procedure).

The term "peptide epitope" encompasses modified peptides. For example tumour associated antigen peptides may be mutated, by amino acid insertion, deletion or substitution, so long as the MHC binding-specificity of the wild-type tumour associated antigen peptide is retained. In a preferred embodiment the modified epitope has greater affinity for the peptide binding groove. Preferably the peptide contains 5 or fewer mutations from the wild-type sequence, more preferably 3 or fewer, most preferably 1 or 0 mutations.

Alternatively (or in addition) modifications may be made without changing the amino acid sequence of the peptide. For example, D-amino acids or other unnatural amino acids can be included, the normal amide bond can be replaced by ester or alkyl backbone bonds, N- or C-alkyl substituents, side chain modifications, and constraints such as disulphide bridges and side chain amide or ester linkages can be included. Such changes may result in greater in vivo stability of the peptide, and a longer biological lifetime.

Other forms of modification included posttranslational modifications such as phosphorylation and glycosylation of the peptides. Posttranslational modified peptides induce essentially the same immune response as other peptides according to the invention. Certain modifications might lead to an increase in the induced immune response whereas others would decrease the response. Other modifications include the addition or removal of a glycosylation or phosphorylations site to change or modulate the immune response stimulated by these peptides.

Modification of epitopes may be performed based on predictions for more efficient T-cell induction derived using the program "Peptide Binding Predictions" devised by K. Parker (NIH) which may be found at www-bimas.dcrt.nih.gov/cgi-bin/molbio/ken_parker_comboform (see also Parker, K. C et al. 1994. J. Immunol. 152:163).

A "modified" antigenic peptide epitope includes peptides which have been bound or otherwise associated to transporter peptides or adjuvants, in order to increase their ability to elicit an immune response. For example, peptides may be fused to TAP independent transporter peptides for efficient transport to HLA and interaction with HLA molecules to enhance CTL epitopes (for review see Yewdell et al., 1998 J Immunother 21:127-31; Fu et al., (1998) J Virol 72:1469-81).

In a further embodiment, antigens or peptides derived from such antigens may be fused to hepatitis B core antigen to enhance T helper and antibody responses (Schodel et al., 1996 Intervirology 39:104-10).

To be an epitope, the peptide should be capable of binding to the peptide-binding groove of a MHC class I or II molecule and be recognised by a T cell.

Cell surface presentation of peptides derived from a given antigen is not random and tends to be dominated by a small number of frequently occurring epitopes. The dominance of a particular peptide will depend on many factors, such as relative affinity for binding the MHC molecule, spatio-temporal point of generation within the APC and resistance to degradation. The epitope hierarchy for an antigen is thought to change with progression of an immune response. After a primary immune response to the immunodominant peptides, epitope "spreading" may occur to sub-dominant determinants (Lehmann et al (1992) Nature 358:155-157).

For any given antigen, cryptic epitopes may also exist. Cryptic epitopes are those which can stimulate a T cell response when administered as a peptide but which fail to produce such a response when administered as a whole antigen. It may be that during processing of the antigen into peptides in the APC the cryptic epitope is destroyed.

The peptide for use in the invention may be an immunodominant epitope, a sub-dominant epitope or a cryptic epitope.

Epitopes for an antigen may be identified by measuring the T cell response to overlapping peptides spanning a portion of the antigen when presented by APC. Such studies usually result in "nested sets" of peptides, and the minimal epitope for a particular T cell line/clone can be assessed by measuring the response to truncated peptides.

The minimal epitope for an antigen may not be the best epitope for practical purposes. It may well be that amino acids flanking the minimal epitope will be required for optimal binding to the MHC.

The peptides are tested in an antigen presentation system which comprises antigen presenting cells and T cells. For example, the antigen presentation system may be a murine splenocyte preparation, a preparation of human cells from tonsil or PBMC. Alternatively, the antigen presentation system may comprise a particular T cell line/clone and/or a particular antigen presenting cell type.

T cell activation may be measured via T cell proliferation (for example using $^3$H-thymidine incorporation) or cytokine production. Activation of TH1-type CD4+ T cells can, for example be detected via IFNγ production which may be detected by standard techniques, such as an ELISPOT assay.

Polyepitope String

It has been found that a particularly effective way to induce an immune response to an antigen is by the use of a polyepitope string, which contains a plurality of antigenic epitopes from one or more antigens linked together. For example, for malaria, a polyepitope string of mainly malaria (*P. falciparum*) CD8 T cell peptide epitopes has been described which also expresses CD4 T cell epitopes from tetanus toxoid and from the 38 Kd mycobacterial antigen of various strains of *M. tuberculosis* and *M. bovis*.

Accordingly, the tumour associated antigen for use in the present invention may be a polyepitope string comprising at least one peptide from a tumour associated antigen. Suitably a polyepitope string is made up of at least one, two, three, four or more peptide epitopes. The string may also comprise another epitope derivable from an antigen such as the 5T4 antigen or an epitope from another antigen—such as another TAA—or combinations thereof. A polyepitope string may optionally comprise additional intervening amino acids between the different tumour antigen epitopes. Suitably epitopes are joined by additional sequences that are absent from the full length protein.

Cell Penetrators

The present invention also provides the use of an antigen or a peptide epitope thereof, or a polyepitope string in association with a cell penetrator.

Antigen presenting cells (such as dendritic cells) pulsed with peptides have proven effective in enhancing antitumour immunity (Celluzzi et al (1996) J. Exp. Med. 183 283-287; Young et al (1996) J. Exp. Med. 183 7-11). It has been shown that it is possible to prolong the presentation of a peptide by dendritic cells (and thus enhance antitumour immunity) by linking it to a cell penetrating peptide (CPP) (Wang and Wang (2002) Nature Biotechnology 20 149-154).

A cell penetrator may be any entity which enhances the intracellular delivery of the peptide/polyepitope string to the antigen presenting cell. For example, the cell penetrator may be a lipid which, when associated with the peptide, enhances its capacity to cross the plasma membrane. Alternatively, the cell penetrator may be a peptide. Several cell penetrating peptide (CPPs) have been identified from proteins, including the Tat protein of HIV (Frankel and Pabo (1988) Cell 55

1189-1193), the VP22 protein of HSV (Elliott and O'Hare (1997) Cell 88 223-233) and fibroblast growth factor (Lin et al (1995) J. Biol. Chem. 270 14255-14258).

The term "associated with" is intended to include direct linkage, for example by a covalent bond. Examples of covalent bonds for linking amino acids include disulphide bridges and peptide bonds. In a preferred embodiment, the peptide/polyepitope string and a CPP are linked by a peptide bond to create a fusion protein.

The term also includes non-covalent linkage, such as association by electrostatic bonding, hydrogen bonding and van der Waals forces. The cell penetrator and peptide/polyepitope string may be associated without covalent or non-covalent bonding. For example the cell penetrator may be a lipid which encapsulates the peptide/polyepitope string (e.g. a liposome).

Compositions for Administering Tumour Associated Antigens

Vector System

A nucleic acid sequence encoding an antigen for use in the present invention may be delivered or administered to a mammal such as a human patient by way of a vector system.

As used herein, a "vector" may be any agent capable of delivering or maintaining nucleic acid in a host cell, and includes viral vectors, plasmids, naked nucleic acids, nucleic acids complexed with polypeptide or other molecules and nucleic acids immobilised onto solid phase particles. Such vectors are described in detail below. It will be understood that the present invention, in its broadest form, is not limited to any specific vector for delivery of the tumour associated antigen-encoding nucleic acid.

Nucleic acids encoding antigens, epitopes and polyepitope strings in accordance with the present invention can be delivered or administered by viral or non-viral techniques.

Non-viral delivery systems include but are not limited to DNA transfection methods. Here, transfection includes a process using a non-viral vector to deliver a gene encoding an antigen to a target mammalian cell.

Typical transfection methods include electroporation, nucleic acid biolistics, lipid-mediated transfection, compacted nucleic acid-mediated transfection, liposomes, immunoliposomes, lipofectin, cationic agent-mediated, cationic facial amphiphiles (CFAs) (Nature Biotechnology 1996 14; 556), multivalent cations such as spermine, cationic lipids or polylysine, 1,2,-bis(oleoyloxy)-3-(trimethylammonio) propane (DOTAP)-cholesterol complexes (Wolff and Trubetskoy 1998 Nature Biotechnology 16: 421) and combinations thereof.

Non-viral delivery systems may also include, but are not limited to, bacterial delivery systems. The use of bacteria as anticancer agents and as delivery agents for anticancer drugs has been reviewed in Expert Opin Biol Ther 2001 March; 1(2):291-300.

Suitable bacteria include, but are not limited to, bacterial pathogens and non-pathogenic commensal bacteria. By way of example, suitable genera may be selected from *Salmonella, Mycobacterium, Yersinia, Shigella, Listeria* and *Brucella*. Recent advances in the pathogenesis and molecular biology of these bacteria have allowed the rational development of new and improved bacterial carriers and more effective gene expression systems. These advances have improved the performance and versatility of these delivery systems.

The bacteria may be invasive intracellular bacteria that are able to transfer eukaryotic expression plasmids into mammalian host cells in vitro and in vivo. Plasmid transfer may take place when the recombinant bacterium dies within the host cell, either due to metabolic attenuation or induction of autolysis. Alternatively, antibiotics may be used and spontaneous transfer has also been observed, indicating that this phenomenon might also occur under physiological conditions. Plasmid transfer has been reported for *Shigella flexneri, Salmonella typhimurium, S. typhi, Listeria monocytogenes* and recombinant *Escherichia coli*, but other invasive bacteria may also be used.

Bacteria may be used for DNA vaccine delivery. Such bacteria may enter the host cell cytosol after phagocytosis, for example, *Shigella* and *Listeria*, or they remain in the phagosomal compartment—such as *Salmonella*. Both intracellular localisations may be suitable for successful delivery of DNA vaccine vectors.

The bacterial delivery systems may utilise *Mycobacterium* in the form of non pathogenic *Mycobacterium* strains, genetic transfer systems in the form of cloning and expression vectors, and related technologies to provide products containing, for example, non toxic immuno-regulating *Mycobacterium* adjuvants, non toxic immuno-stimulating exogenous antigens specific for a variety of diseases, and non toxic amounts of cytokines that boost the TH-1 pathway (Tunis Med 2001 February; 79(2):65-81).

*Salmonella* strains—such as attenuated strains—which comprise defined gene deletions, may be used as suitable delivery systems—such as the delivery of antigens. A number of strategies for delivery by these strains have been attempted, ranging from plasmid-based to chromosomal integration systems. By way of example, Rosenkranz et al. Vaccine 2003, 21(7-8), 798-801 describe eukaryotic expression plasmids encoding cytokines, and assessed their capacity to modulate immune responses in different experimental models. Plasmids encoding mouse IL-4 and IL-18 under cytomegalovirus promoter were constructed and transformed into live attenuated *Salmonella enterica* serovar *Typhi* strain CVD 908-htrA, and *Salmonella enterica* serovar *Typhimurium* strain SL3261.

The use of attenuated *Salmonella typhimurium* as a potential gene delivery vector has been reviewed in Anticancer Res 2002, 22(6A):3261-6.

*Brucella abortus* may also be used as a suitable delivery system as described by Vemulapalli et al. Infect Immun (2000) 68(6):3290-6. *Brucella abortus* strain RB51 is a stable, rough, attenuated mutant widely used as a live vaccine for bovine brucellosis. This strain may be used as a delivery vector, for example, in the delivery of protective antigens of other intracellular pathogens to which the induction of a strong Th1 type of immune response is needed for effective protection.

Boyd et al. Eur J Cell Biol (2000) 79 (10) 659-71 describe the use of *Yersinia enterocolitica* for the delivery of proteins into a wide range of cell types. *Y. enterocolitica* translocates virulence proteins, called Yop effectors, into the cytosol of eukaryotic cells. No limit to the range of eukaryotic cells into which *Y. enterocolitica* can translocate Yops was reported. The Yop effectors YopE, YopH and YopT were each cytotoxic for the adherent cell types tested, showing that not only is *Y. enterocolitica* not selective in its translocation of particular Yop effectors into each cell type, but also that the action of these Yop effectors is not cell type specific. To use the *Yersinia* translocation system for broad applications, a *Y. enterocolitica* translocation strain and vector for the delivery of heterologous proteins into eukaryotic cells was constructed. This strain and vector combination lacks the translocated Yop effectors and allows delivery into eukaryotic cells of heterologous proteins fused to the minimal N-terminal secretion/translocation signal of YopE.

U.S. Pat. No. 5,965,381 describes a recombinant *Yersinia* for the delivery of proteins into eukaryotic cells. Such *Yers-*

*inia* are deficient in the production of functional effector proteins, but are endowed with a functional secretion and translocation system.

Cell adhesion molecules are a large group of molecules involved in a variety of cell-to-cell and cell-to-extra-cellular matrix (ECM) interactions and are exploited by a number of pathogenic micro-organisms as receptors for cell entry. These molecules may be used for the targeting and uptake of both gene and drug delivery systems. Cell adhesion molecules and their use in gene transfer has been reviewed in Adv Drug Deliv Rev 2000 Nov. 15; 44(2-3):135-52.

The gene gun delivery system may also be used for the delivery of DNA, which is a highly reliable method compared to intramuscular inoculation (Jpn J Pharmacol 2000 July; 83(3): 167-74).

Viral delivery systems include but are not limited to adenovirus vectors, adeno-associated viral (AAV) vectors, herpes viral vectors, retroviral vectors, lentiviral vectors or baculoviral vectors, Venezuelan equine encephalitis virus (VEE), poxviruses such as: canarypox virus (Taylor et al 1995 Vaccine 13:539-549), entomopox virus (Li Y et al 1998 XII$^{th}$ International Poxvirus Symposium p 144. Abstract), penguine pox (Standard et al. J Gen Virol. 1998 79:1637-46) alphavirus, and alphavirus based DNA vectors.

Examples of retroviruses include but are not limited to: murine leukaemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukaemia virus (Mo-MLV), FBR murine osteosarcoma virus (FBR MSV), Moloney murine sarcoma virus (Mo-MSV), Abelson murine leukaemia virus (A-MLV), Avian myelocytomatosis virus-29 (MC29), and Avian erythroblastosis virus (AEV).

A detailed list of retroviruses may be found in Coffin et al ("Retroviruses" 1997 Cold Spring Harbour Laboratory Press Eds: J M Coffin, S M Hughes, H E Varmus pp 758-763).

Lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (MV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells (Lewis et al 1992 EMBO. J 11: 3053-3058; Lewis and Emerman 1994 J. Virol. 68: 510-516). In contrast, other retroviruses—such as MLV—are unable to infect non-dividing cells such as those that make up, for example, muscle, brain, lung and liver tissue.

The vector for use in the present invention may be configured as a split-intron vector. A split intron vector is described in PCT patent applications WO 99/15683 and WO 99/15684.

If the features of adenoviruses are combined with the genetic stability of retroviruses/lentiviruses then essentially the adenovirus can be used to transduce target cells to become transient retroviral producer cells that could stably infect neighbouring cells. Such retroviral producer cells engineered to express 5T4 antigen can be implanted in organisms such as animals or humans for use in the treatment of angiogenesis and/or cancer.

The vector for use in the present invention may be configured as a psuedotyped vector.

In the design of retroviral vectors it may be desirable to engineer particles with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector particle to replace or add to the native envelope protein of the virus.

The term pseudotyping means incorporating in at least a part of, or substituting a part of, or replacing all of, an env gene of a viral genome with a heterologous env gene, for example an env gene from another virus. Pseudotyping is not a new phenomenon and examples may be found in WO 99/61639, WO-A-98/05759, WO-A-98/05754, WO-A-97/17457, WO-A-96/09400, WO-A-91/00047 and Mebatsion et al 1997 Cell 90, 841-847.

Pseudotyping can improve retroviral vector stability and transduction efficiency. A pseudotype of murine leukemia virus packaged with lymphocytic choriomeningitis virus (LCMV) has been described (Miletic et al (1999) J. Virol. 73:6114-6116) and shown to be stable during ultracentrifugation and capable of infecting several cell lines from different species.

Poxvirus Vectors

Antigens such as TAAs are weakly immunogenic, being recognised as "self" by the immune system and thus tolerated to a large extent. The use of poxvirus vectors is sometimes able to cause the antigens to be presented such that this tolerance may be overcome at least in part, (especially if immune evasion genes are deleted—see below) thus enabling a host to raise an immune response.

Poxvirus vectors are preferred for use in the present invention. Pox viruses are engineered for recombinant gene expression and for the use as recombinant live vaccines. This entails the use of recombinant techniques to introduce nucleic acids encoding foreign antigens into the genome of the pox virus. If the nucleic acid is integrated at a site in the viral DNA which is non-essential for the life cycle of the virus, it is possible for the newly produced recombinant pox virus to be infectious, that is to say to infect foreign cells and thus to express the integrated DNA sequence. The recombinant pox virus prepared in this way can be used as live vaccines for the prophylaxis and/or treatment of pathologic and infectious disease.

Expression of antigen peptide(s) in recombinant pox viruses, such as vaccinia viruses, requires the ligation of vaccinia promoters to the nucleic acid encoding the 5T4 peptide(s). Plasmid vectors (also called insertion vectors), have been constructed to insert nucleic acids into vaccinia virus through homologous recombination between the viral sequences flanking the nucleic acid in a donor plasmid and homologous sequence present in the parental virus (Mackett et al 1982 PNAS 79: 7415-7419). One type of insertion vector is composed of: (a) a vaccinia virus promoter including the transcriptional initiation site; (b) several unique restriction endonuclease cloning sites located downstream from the transcriptional start site for insertion of nucleic acid; (c) nonessential vaccinia virus sequences (such as the Thymidine Kinase (TK) gene) flanking the promoter and cloning sites which direct insertion of the nucleic acid into the homologous nonessential region of the virus genome; and (d) a bacterial origin of replication and antibiotic resistance marker for replication and selection in *E. Coli*. Examples of such vectors are described by Mackett (Mackett et al 1984, J. Virol. 49: 857-864).

The isolated plasmid containing the nucleic acid to be inserted is transfected into a cell culture, e.g., chick embryo fibroblasts, along with the parental virus, e.g., poxvirus. Recombination between homologous pox DNA in the plasmid and the viral genome respectively results in a recombinant poxvirus modified by the presence of the promoter-gene construct in its genome, at a site which does not affect virus viability.

As noted above, the nucleic acid is inserted into a region (insertion region) in the virus which does not affect virus viability of the resultant recombinant virus. Such regions can be readily identified in a virus by, for example, randomly testing segments of virus DNA for regions that allow recombinant formation without seriously affecting virus viability of the recombinant. One region that can readily be used and is present in many viruses is the thymidine kinase (TK) gene. For example, the TK gene has been found in all pox virus genomes examined [leporipoxvirus: Upton, et al J. Virology 60:920 (1986) (shope fibroma virus); capripoxvirus: Gershon, et al J. Gen. Virol. 70:525 (1989) (Kenya sheep-1); orthopoxvirus: Weir, et al J. Virol 46:530 (1983) (vaccinia); Esposito, et al Virology 135:561 (1984) (monkeypox and variola virus); Hruby, et al PNAS, 80:3411 (1983) (vaccinia); Kilpatrick, et al Virology 143:399 (1985) (Yaba monkey tumour virus); avipoxvirus: Binns, et al J. Gen. Virol 69:1275 (1988) (fowlpox); Boyle, et al Virology 156:355 (1987) (fowlpox); Schnitzlein, et al J. Virological Method, 20:341 (1988) (fowlpox, quailpox); entomopox (Lytvyn, et al J. Gen. Virol 73:3235-3240 (1992)].

In vaccinia, in addition to the TK region, other insertion regions include, for example, HindIII M.

In fowlpox, in addition to the TK region, other insertion regions include, for example, BamHI J [Jenkins, et al AIDS Research and Human Retroviruses 7:991-998 (1991)] the EcoRI-HindIII fragment, BamHI fragment, EcoRV-HindIII fragment, BamHI fragment and the HindIII fragment set forth in EPO Application No. 0 308 220 A1. [Calvert, et al J. of Virol 67:3069-3076 (1993); Taylor, et al Vaccine 6:497-503 (1988); Spehner, et al (1990) and Boursnell, et al J. of Cen. Virol 71:621-628 (1990)].

In swinepox preferred insertion sites include the thymidine kinase gene region.

A promoter can readily be selected depending on the host and the target cell type. For example in poxviruses, pox viral promoters should be used, such as the vaccinia 7.5K, or 40K or fowlpox C1. Artificial constructs containing appropriate pox sequences can also be used. Enhancer elements can also be used in combination to increase the level of expression. Furthermore, the use of inducible promoters, which are also well known in the art, are preferred in some embodiments.

Foreign gene expression can be detected by enzymatic or immunological assays (for example, immuno-precipitation, radioimmunoassay, or immunoblotting). Naturally occurring membrane glycoproteins produced from recombinant vaccinia infected cells are glycosylated and may be transported to the cell surface. High expressing levels can be obtained by using strong promoters.

Other requirements for viral vectors for use in vaccines include good immunogenicity and safety. MVA is a replication-impaired vaccinia strain with a good safety record. In most cell types and normal human tissue, MVA does not replicate. Replication of MVA is observed in a few transformed cell types such as BHK21 cells. Carroll et al (1997) have shown that the recombinant MVA is equally as good as conventional recombinant vaccinia vectors at generating a protective CD8+T cell response and is an efficacious alternative to the more commonly used replication competent vaccinia virus. The vaccinia virus strains derived from MVA, or independently developed strains having the features of MVA which make MVA particularly suitable for use in a vaccine, are also suitable for use in the present invention.

Preferably, the vector is a vaccinia virus vector such as MVA or NYVAC. Most preferred is the vaccinia strain modified virus ankara (MVA) or a strain derived therefrom. Alternatives to vaccinia vectors include avipox vectors such as fowlpox or canarypox known as ALVAC and strains derived therefrom which can infect and express recombinant proteins in human cells but are unable to replicate.

In one aspect of the present invention at least one immune evasion gene is deleted from the poxvirus vector.

Viruses, especially large viruses such a poxviruses which have an extensive coding capacity and can thus encode a variety of genes, have developed a number of techniques for evading the immune system of their hosts. For example, they are able to evade non-specific defences such as complement, interferons and the inflammatory response, as well as to interfere with or block the function of cytokines. A number of these immune evasion polypeptides have been deleted from MVA, with the exception of the interferon resistance protein in the left terminal region.

Poxviruses in general, are large DNA viruses which establish acute, rather than latent, infections. They encode so many antigenic proteins that antigenic variation is difficult, thus relying on active immune evasion to protect themselves from the mammalian immune system. They possess a number of genes which encode polypeptides which are responsible for interfering with a number of aspects of the immune system: they disrupt interferon action, interfere with complement, cytokine activity, inflammatory responses and CTL recognition (for a review, Smith et al., (1997) Immunol Rev 159:137-154). Removal of these proteins is beneficial in promoting the ability of weak immunogens encoded on a poxvirus vector to elicit an immune response in a subject.

An immune evasion gene or polypeptide is a gene, or its product, which assists the virus in evading the mammalian immune system. Preferably, the gene or gene product interferes with the working of the immune system, at least one level. This may be achieved in a number of ways, such as by interfering in signalling pathways by providing competitors for signalling molecules, by providing soluble cytokine receptor mimics and the like.

Immune evasion genes include, but are not limited to, the following:

Interferon evasion genes. Vaccinia possesses at least three genes which interfere with IFN action. The E3L gene expresses a 25 Kd polypeptide which competes with P1 protein kinase for binding to dsRNA, an event which leads to activation of P1, phosphorylation of eIF2$\alpha$ and resultant failure of translation initiation complex assembly. This pathway is ordinarily responsive to IFN activation, but is impeded by E3L expression thus allowing translation initiation to proceed unimpeded.

The K3L gene expresses a 10.5 Kd polypeptide which also interferes with P1 activity, since it is effectively an eIF2$\alpha$ mimic and acts as a competitor for P1 protein kinase. Its mode of action is thus similar to E3L.

The A18R gene is predicted to encode a helicase, which appears to interfere with the 2',5'-oligoadenylate pathway, which is in turn IFN responsive. 2',5'-A activates RNAse L, which acts to prevent viral translation. Expression of A18R appears to reduce 2',5'-A levels in infected cells.

Complement. The product of the B5R gene of vaccinia is known to be highly related to factor H, a regulator of the alternative complement pathway. This pathway may be activated by antigen alone, unlike the classical pathway. The B5R gene product thus may interfere with the alternative complement pathway.

The C21L gene is in turn related to C4b-binding protein in humans, and interacts with cells bearing C4b on the surface to prevent binding to the CR1 complement receptor.

Soluble Cytokine Receptors. The product of the vaccinia WR B15R gene (B16R in Copenhagen strain vaccinia) is related to IL1-R.

The WR gene ORF SalF19R, A53R in Copenhagen strain vaccinia, encodes a TNF receptor. However, in wild-type virus both of these genes are believed to be inactive due to fragmentation of the ORFs.

The B8R gene is believed to encode a soluble IFNγ receptor, providing the virus with yet another IFN evasion mechanism.

Inflammation. A number of genes are believed to be involved in the prevention of inflammatory responses to viral infection. These include A44L, K2L, B13R and B22R.

In one aspect of the present invention, the majority of the immune evasion genes are deleted from the recombinant poxvirus vector. Preferably, all the immune evasion genes are deleted. Thus, in one aspect of the present invention, the recombinant poxvirus vector is a recombinant MVA vector in which the K3L interferon resistance protein gene has been disrupted or deleted.

Preferred are poxviruses which are non-hazardous to the intended subject. Thus, for example, for use in humans, poxviruses which are either host-range restricted, such as avipox viruses, or otherwise attenuated, such as attenuated strains of vaccinia (including NYVAC and MVA) are preferred. Most preferred are attenuated vaccinia virus strains, although non-vaccinia strains are usefully employed in subjects with pre-existing smallpox immunity.

A construct which contains at least one nucleic acid which codes for a tumour associated antigen epitope(s) flanked by MVA DNA sequences adjacent to a naturally occurring deletion, e.g. deletion II, within the MVA genome, is introduced into cells infected with MVA, to allow homologous recombination.

Once the construct has been introduced into the eukaryotic cell and the tumour associated antigen epitope DNA has recombined with the viral DNA, the desired recombinant vaccinia virus, can be isolated, preferably with the aid of a marker (Nakano et al Proc. Natl. Acad. Sci. USA 79, 1593-1596 [1982], Franke et al Mol. Cell. Biol. 1918-1924 [1985], Chakrabarti et al Mol. Cell. Biol. 3403-3409 [1985], Fathi et al Virology 97-105 [1986]).

The construct to be inserted can be linear or circular. A circular DNA is preferred, especially a plasmid. The construct contains sequences flanking the left and the right side of a naturally occurring deletion, e.g. deletion II, within the MVA genome (Altenburger, W., Suter, C. P. and Altenburger J. (1989) Arch. Virol. 105, 15-27). The foreign DNA sequence is inserted between the sequences flanking the naturally occurring deletion.

For the expression of at least one nucleic acid, it is necessary for regulatory sequences, which are required for the transcription of the nucleic acid to be present upstream of the nucleic acid. Such regulatory sequences are known to those skilled in the art, and includes for example those of the vaccinia 11 kDa gene as are described in EP-A-198,328, and those of the 7.5 kDa gene (EP-A-110,385).

The construct can be introduced into the MVA infected cells by transfection, for example by means of calcium phosphate precipitation (Graham et al Virol. 52, 456-467 [1973; Wigler et al Cell 777-785 [1979] by means of electroporation (Neumann et al EMBO J. 1, 841-845 [1982]), by microinjection (Graessmann et al Meth. Enzymology 101, 482-492 (1983)), by means of liposomes (Straubinger et al Methods in Enzymology 101, 512-527 (1983)), by means of spheroplasts (Schaffner, Proc. Natl. Acad. Sci. USA 77, 2163-2167 (1980)) or by other methods known to those skilled in the art. Transfection by means of liposomes is preferred.

The recombinant vectors for use in the present invention can have a tropism for a specific cell type in the mammal. By way of example, the recombinant vectors of the present invention can be engineered to infect professional APCs such as dendritic cells and macrophages. Dendritic cells are known to be orchestrators of a successful immune response especially that of a cell mediated response. It has been shown that ex vivo treatment of dendritic cells with antigen or viral vectors containing such a target antigen, will induce efficacious immune responses when infused into syngeneic animals or humans (see Nestle F O, et al. Vaccination of melanoma patients with peptide- or tumor lysate-pulsed dendritic cells, Nat. Med. 1998 March; 4(3):328-32 and Kim C J et al. Dendritic cells infected with poxviruses encoding MART-1/Melan A sensitize T lymphocytes in vitro. J. Immunother. 1997 July; 20(4):276-86. The recombinant vectors can also infect tumour cells. Alternatively, the recombinant vectors are able to infect any cell in the mammal.

Other examples of vectors include ex vivo delivery systems, which include but are not limited to DNA transfection methods such as electroporation, DNA biolistics, lipid-mediated transfection and compacted DNA-mediated transfection.

The vector may be a plasmid DNA vector. As used herein, "plasmid" refers to discrete elements that are used to introduce heterologous DNA into cells for either expression or replication thereof. Selection and use of such vehicles are well within the skill of the artisan.

Suitably the vector system for administration of the tumour associated antigen is the TroVax® vaccine, a cancer vaccine in clinical development for delivery of 5T4 using an attenuated vaccinia virus vector (MVA). TroVax® is currently being evaluated in phase II clinical trials in late stage colorectal, renal and prostate cancer patients. Trials using TroVax are described, for example, in PCT/GB2005/000026. Furthermore variations or modifications based on TroVax to administer tumour associated antigens is also envisaged.

Pulsed Cells

The present invention also provides administration of an antigen using cells pulsed with tumour associated antigen or peptides.

Preferably the cells to be pulsed are capable of expressing MHC class I or class II molecules.

MHC class I molecules can be expressed on nearly all cell types, but expression of MHC class II molecules is limited to so-called "professional" antigen presenting cells (APCs); B cells, dendritic cells and macrophages. However, expression of MHC class II can be induced on other cell types by treating with IFNγ.

Expression of MHC class I or MHC class II molecules can also be achieved by genetic engineering (i.e. provision of a gene encoding the relevant MHC molecule to the cell to be pulsed). This approach has the advantage that an appropriate MHC haplotype(s) can be chosen which bind specifically to the peptide(s).

Preferably the cell to be pulsed is an antigen presenting cell, i.e. a cell which, in a normal immune response, is capable of processing an antigen and presenting it at the cell surface in conjunction with an MHC molecule. Antigen presenting cells include B cells, macrophages and dendritic cells. In an especially preferred embodiment, the cell is a dendritic cell.

Preferably the cell is capable of expressing an MHC molecule which binds a peptide according to the first aspect of the invention in its peptide binding groove. For example, the cell may express one of the following HLA restriction elements: B8, Cw7 or A2 (for MHC class I).

Peptide pulsing protocols are known in the art (see for example Redchenko and Rickinson (1999) J. Virol. 334-342; Nestle et al (1998) Nat. Med. 4 328-332; Tjandrawan et al (1998) J. Immunotherapy 21 149-157). For example, in a standard protocol for loading dendritic cells with peptides, cells are incubated with peptide at 50 µg/ml with 3 µg/ml β-2 microglobulin for two hours in serum free medium. The unbound peptide is then washed off.

The pulsed cell of the invention may be used as a vaccine, for example to stimulate a prophylactic or therapeutic immune response against a specific tumour associated antigen.

The present invention therefore also provides a method for treating and/or preventing a disease which comprises the step of administering a peptide-pulsed cell to a subject in need of same in combination with a chemotherapeutic agent.

Nucleic Acid

The antigen for use in the composition or medicament or for administration in a combination in accordance with the invention may be provided through a nucleic acid molecule encoding said tumour associated antigen.

A "nucleic acid", as referred to herein, may be DNA or RNA, naturally-occurring or synthetic, or any combination thereof. Nucleic acids according to the invention are limited only in that they serve the function of encoding a tumour associated antigen peptide in such a way that it may be translated by the machinery of the cells of a host organism. Thus, natural nucleic acids may be modified, for example to increase the stability thereof. DNA and/or RNA, but especially RNA, may be modified in order to improve nuclease resistance of the members. For example, known modifications for ribonucleotides include 2'-O-methyl, 2'-fluoro, 2'-NH$_2$, and 2'-O-allyl. The modified nucleic acids according to the invention may comprise chemical modifications which have been made in order to increase the in vivo stability of the nucleic acid, enhance or mediate the delivery thereof, or reduce the clearance rate from the body. Examples of such modifications include chemical substitutions at the ribose and/or phosphate and/or base positions of a given RNA sequence. See, for example, WO 92/03568; U.S. Pat. No. 5,118,672; Hobbs et al., (1973) Biochemistry 12:5138; Guschlbauer et al., (1977) Nucleic Acids Res. 4:1933; Schibaharu et al., (1987) Nucleic Acids Res. 15:4403; Pieken et al., (1991) Science 253:314, each of which is specifically incorporated herein by reference.

Nucleic acids encoding suitable antigens or peptide derived therefrom will be familiar to those skilled in the art or can be derived using methods which are standard to those skilled in the art. For example, a DNA for use in the present invention is obtainable by chemical synthesis, using polymerase chain reaction (PCR) or direct cleavage from a longer polynucleotide, such as the entire tumour associated antigen coding sequence or a fragment thereof.

Nucleic acids encoding suitable antigens and peptides or polyepitope strings derived therefrom may be codon optimised. Codon optimisation has previously been described in WO 99/41397 and WO01/79518. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase protein expression. By the same token, it is possible to decrease expression by deliberately choosing codons for which the corresponding tRNAs are known to be rare in the particular cell type. Thus, an additional degree of translational control is available. Codon usage tables are known in the art for mammalian cells, as well as for a variety of other organisms.

Variants/Fragments/Homologues/Derivatives

The present invention encompasses the use of nucleotide and amino acid sequences encoding antigens and variants, homologues, derivatives and fragments thereof.

The term "variant" is used to mean a naturally occurring polypeptide or nucleotide sequence which differs from a wild-type sequence.

The term "fragment" indicates that a polypeptide or nucleotide sequence comprises a fraction of a subject sequence. Preferably the sequence comprises at least 50%, more preferably at least 65%, more preferably at least 80%, more preferably at least 90%, most preferably at least 90% of the subject sequence. If the fragment is a fragment of an amino acid then preferably the fragments are 6-12 amino acids in length. More preferably, the fragments are 8, 9 or 10 amino acids in length.

The term "homologue" means an entity having a certain homology with the subject amino acid sequences and the subject nucleotide sequences. Here, the term "homology" can be equated with "identity".

In the present context, a homologous sequence is taken to include an amino acid sequence, which may be at least 75, 85 or 90% identical, preferably at least 95 or 98% identical to the subject sequence. Typically, the homologues will comprise the same activity as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence, which may be at least 75, 85 or 90% identical, preferably at least 95 or 98% identical to the subject sequence. Typically, the homologues will comprise the same activity as the subject sequence. Although homology can also be considered in terms of similarity (i.e. amino acid residues having similar chemical properties/functions), in the context of the present invention it is preferred to express homology in terms of sequence identity.

Methods for determining sequence identity are familiar to those skilled in the art.

One suitable homologue of 5T4 is described in GB 0615655.8 herein incorporated by reference.

Vaccine/Pharmaceutical Composition

The present invention provides a vaccine/pharmaceutical composition comprising an antigen, a peptide epitope derived from a tumour associated antigen, a polyepitope string, a nucleic acid sequence, a vector system and/or a cell as described above for use in combination with a chemotherapeutic agent or agents.

For administering the antigen or derivatives as described above, the vaccine may by prepared as an injectable, either as liquid solution or suspension; solid form suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminium hydroxide, aluminium phosphate, aluminium potassium sulphate (alum), beryllium sulphate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as Amphigen (oil-in-water), Alhydrogel (aluminium hydroxide), or a mixture of Amphigen and Alhydrogel are used. Only aluminium hydroxide is approved for human use.

The proportion of immunogen and adjuvant can be varied over a broad range so long as both are present in effective amounts. For example, aluminium hydroxide can be present in an amount of about 0.5% of the vaccine mixture ($Al_2O_3$ basis). Conveniently, the vaccines are formulated to contain a final concentration of immunogen in the range of from 0.2 to 200 μg/ml, preferably 5 to 50 μg/ml, most preferably 15 μg/ml.

After formulation, the vaccine may be incorporated into a sterile container which is then sealed and stored at a low temperature, for example 4° C., or it may be freeze-dried. Lyophilisation permits long-term storage in a stabilised form.

The vaccine may be administered in a convenient manner such as by the oral, intravenous (where water soluble), intramuscular, subcutaneous, intranasal, intradermal or suppository routes or implanting (e.g. using slow release molecules).

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

Peptides and polypeptides may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

5T4 peptides may be administered with costimulatory molecules such as those involved in the interaction between receptor-ligand pairs expressed on the surface of antigen presenting cells and T cells. Such costimulatory molecules can be administered by administration of the protein molecule or of the corresponding nucleic acid encoding the protein molecule. Suitable costimulatory molecules include CD40, B7-1, B7-2, CD54, members of the ICAM family (eg ICAM-1, -2, or -3), CD58, SLAM ligands, polypeptides that bind heat stable antigen, polypeptides which bind to members or the TNF receptor family (e.g. 4-1BBL, TRAF-1, TRAF-2, TRAF-3, OX40L, TRAF-5, CD70) and CD 154. Peptides may also be administered in combination with stimulatory chemokines or cytokines including, for example, IL-2, IL-3, IL4, SCF, IL-6, IL7, IL-12, IL15, IL16, IL18, G-CSF, GM-CSF, IL-1alpha, IL-11, MIP-1, LIF, c-kit ligand, thrombopoietin and flt3 ligand, TNF-α and interferons such as IFN-α or IFN-γ. Chemokines may also be used in combination with the antigen or peptides, such as CCL3 or CCL5 or may be fused with the peptides of the invention (e.g. CXCL10 and CCL7). Where the antigen or peptides are administered by administering a nucleic acid encoding the peptide, the costimulatory molecule may also be administered by administering the corresponding nucleic acid encoding the costimulatory molecule.

For example, treatment with anti-CTLA-4, anti-CD25, anti-CD4, the fusion protein IL13Ra2-Fc, and combinations thereof (such as anti-CTLA-4 and anti-CD25) have been shown to upregulate anti-tumour immune responses and would be suitable to be used in combination with the peptides of the present invention. The regulatory T-cell (Treg) inhibitor ONTAK (IL-2 diptheria toxin conjugate $DAB_{389}IL2$) has also been shown to enhance vaccine-mediated antitumour, thus inhibitors of Tregs are also suitable for use with the vaccines of the present invention.

Heterologous Vaccination Regimes

Regimes for administration of vaccines/pharmaceutic compositions according to the present invention may be determined by conventional efficacy testing. Especially preferred, however, are regimes which include successive priming and boosting steps. It is observed that such regimes achieve superior breaking of immune tolerance and induction of T cell responses (see Schneider et al., 1998 Nat Med 4:397-402) as well as induction of B cell and antibody responses.

Prime-boost regimes may be homologous (where the same composition is administered in subsequent doses) or heterologous (where the priming and boosting compositions are different). For example, the priming composition may be a non-viral vector (such as a plasmid) encoding a tumour associated antigen and the boosting composition may be a viral vector (such as a poxvirus vector) encoding a tumour associated antigen, wherein either or both of said "tumour associated antigens" is an epitope or polyepitope string of the present invention.

Prophylactic/Therapeutic Methods

The present invention also provides the use of a combination according to the present invention in the manufacture of a medicament for use in the prevention and/or treatment of a disease.

There is also provided a method for treating and/or preventing a disease in a subject which comprises the step of administering an effective amount of a combination according to the present invention.

As used herein, the terms "treatment", "teating" and "therapy" include curative effects, palliative effects, alleviation effects, prevention of progression, prophylactic effects and any effect which improves the survival of a patient.

Where the vaccine is or comprises a class I peptide epitope, the immune response elicited may involve the activation of 5T4 specific cytotoxic T-lymphocytes. Where the vaccine is or comprises a class II epitope, the immune response elicited may involve the activation of $T_H1$ and/or $T_H2$ cells.

Advantageously, the response is an anti-tumour immunotherapeutic response which is effective to inhibit, arrest or reverse the development of a tumour in a subject.

Chemotherapeutic Agents

"Chemotherapeutic agents" for use in the combination of the present invention are those agents which are agents suitable for anti-cancer or anti-tumour therapies.

Suitable chemotherapeutic agents include standard compounds used in chemotherapy, intercalating agents, and platinum containing compounds, for example. Suitable agents include, but are not limited to all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine.

In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

In one embodiment, the chemotherapeutic agent is cyclophosphamide. In this embodiment, the cyclophosphamide may, preferably be administered in a low dose form. Low dose cyclophosphamide has been observed to enhance an antitumour response in an adoptive cell transfer immunotherapy approach (see Dudley et al. J. Clin. Oncol. (2005) 23, 2346-2357).

In another embodiment, the composition may further comprise a kinase inhibitor, for separate, simultaneous separate or combined use in the treatment of tumours. Suitable kinase inhibitors include those which have been shown to possess anti-tumour activity (such as gefitinib (Iressa) and erlotinib (Tarceva) and these could be used in combination with the peptides. The receptor tyrosine kinase inhibitors, such as Sunitinib malate and Sorafenib which have been shown to be effective in the treatment of renal cell carcinoma are also suitable to be used in the composition.

Other Combination Therapies

The invention further relates to the use of tumour antigen targeting molecules, such as anti-tumour antigen antibodies, for example anti-5T4 scFvs. Tumour antigen targeting molecules also includes T cell receptors (TCRs), including the synthetic TCRs described in WO 2004/033695 and WO 99/60119. These antibodies may be used to (i) to target natural or exogenous 5T4 in situ and/or (ii) deliver immune enhancer molecules, such as B7.1, to natural or exogenous 5T4 in situ (Carroll et al. (1998) J Natl Cancer Inst 90(24): 1881-7). This potentiates the immunogenicity of 5T4 in the subject.

The present invention may also be used with the adoptive transfer of tumour infiltrating lymphocytes isolated from patients (Dudley et al. J. Clin. Oncol. (2005) 23:2346-2357).

Diseases

Diseases which can be treated and/or prevented in accordance with the invention include any of those in which an antigen-specific immune response can contribute to that prevention and/or treatment.

In a preferred embodiment, the disease (which is preventable/treatable using a combination according to the present invention) is a cancer. In particular the disease may be a carcinoma of, for example, the breast, lung, stomach, pancreas, endometrium, cervix, colorectum, kidney or prostate as well as melanoma.

Preferably the disease is one which can be shown to be positive for the tumour associated antigen which is present in the combination.

For example, WO89/07947 describes an immunohistochemical screen of neoplastic tissues using an anti-5T4 monoclonal antibody. Thus, where the tumour associated antigen is 5T4, the disease is, preferably, a cancer which can be shown to be 5T4 positive by diagnostic testing (such as with an anti-5T4 antibody), for example: an invasive carcinoma of the Ampulla of Vater, breast, colon, endometrium, pancreas, or stomach; a squamous carcinoma of the bladder, cervix, lung or oesophagus; a tubulovillous adenoma of the colon; a malignant mixed Mullerian tumour of the endometirem; a clear cell carcinoma of the kidney; a lung cancer (large cell undifferentiated, giant cell carcinoma, bronchoalveolar carcinoma, metastatic leiomyosarcoma); an ovarian cancer (a Brenner tumour, cystadenocarcinoma, solid teratoma); a cancer of the testis (seminoma, mature cystic teratoma); a soft tissue fibrosarcoma; a teratoma (anaplastic germ cell tumours); or a trophoblast cancer (choriocarcimoma (e.g. in uterus, lung or brain), tumour of placental site, hydatidiform mole).

Dosage and Administration

Administration and $CD4^+CD25^+$ Treg Cell Count/CD4+CD25+ Treg Cell Function

In some embodiments of the present invention the antigens and vaccines of the present invention are administered at a reduced $CD4^+CD25^+$ Treg cell count or reduced CD4+CD25+ Treg cell function. Preferably, the optimum timing of vaccination would co-incide with the period when the $CD4^+CD25^+$ Treg cell count reducing agent or the CD4+CD25+ Treg cell function reducing agent, such as a chemotherapeutic agent or agents or Ontak, has caused a maximum depletion/reduction of function of Tregs.

Determination of $CD4^+CD25^+$ Treg Cell Count

The degree of depletion can be determined by analysis of peripheral blood mononuclear cells (PBMCs) isolated from patient blood taken at 24 h periods following a dose of chemotherapy, until the next dose of chemotherapy or for up to 6 weeks after the last administration of chemotherapy. Treg cells are a specific subset of CD4+ T cells that express CD25 at levels higher than CD4 negative cells; and thus Treg levels are assayed by determining the percentage of all CD4+ T cells that are CD4+ CD25+. Thus the levels of CD4+ CD25+hi. Therefore the levels of CD4+ CD25+hi (Tregs) T cells relative to total CD4+ T cell levels will be determined before and after administration the Treg-reducing agent.

In the case of cyclophosphamide, maximum depletion of CD4+CD25+ Tregs occurred four days after administration of CY (Lutsiak et al. 2005 Blood 105:2862-2868).

Levels of other types of T regulatory cells, such as TGF-β producing TH3 cells, IL-10 producing Tr1 cells and CD8+CD28− T cells, may be determined by secretion of cytokines, staining for some cell surface markers and the ability to suppress immune responses (Marshall et al, 2004. Blood. 103:1755-1762; Wei et al, 2005. Cancer Res 65: 5020-6; Leong et al, 2006 Immunol. Lett. 15:229-236; for reviews see Levings and Roncarlo, 2005. CTMI 292:303-326; Huehn, Siegmund and Hamann, 2005. CITR 293:89-114; Faria and Weiner, 2005 Immunol. Rev. 206:232-259; Weiner, 2001 Immunol. Rev. 182:207-214; Weiner et al, 2001. Microbes infect. 3:947-954; Roncarlo et al, 2001 Immunol. Rev. 182: 68-79).

Determination of $CD4^+CD25^+$ Treg Cell Function

Reduction of $CD4^+CD25^+$ Treg cell function will be determined by measuring the loss of suppressive activity of these cells in a number of in vitro assays including proliferation and ELISPOT assays.

Assays can be set up with PBMCs undepleted or depleted of $CD4^+CD25^+$ Treg cells. $CD4^+CD25^+$ Treg cells can be purified from PBMCs, for example by $CD4^+$ and $CD25^+$ separation techniques using magnetic beads or flow cytometry. In the presence of functional $CD4^+CD25^+$ Treg cells, immune responses may not be detected due to suppression caused by the Tregs. In the absence of functional $CD4^+CD25^+$ Treg cells, immune responses may be detected. Purified $CD4^+CD25^+$ Treg cells added back to the depleted PBMCs would result in suppression of these immune responses. In the instance of cells with a reduced function, immune responses may be detected even when said cells are present in the assays. The loss of Treg function would be determined by performing such assays on PBMCs taken before and after administration of the CD4+CD25+ Treg cell function reducing agent.

Chemotherapy Cycles

It is apparent for the skilled person that the compositions, methods and uses of the present invention can be adapted to the specific chemotherapeutic agents and antigens used within the invention without undue experimentation. In particular, a chemotherapeutic agent or agents used in the present invention might require a specific administration and dosage schedule. These administration and dosage schedules might vary for different chemotherapeutic agent. Generally, a chemotherapeutic agent or agents might be administered in short frequent intervals (for example, every 1 or 2 hours) followed by longer periods without administration (for example, 2 week intervals). This succession of administration and non-administration constitutes a chemotherapy cycle. A chemotherapy treatment might consist of a number of cycles depending on the agent used. The period between chemotherapy cycles constitutes the rest period. A rest period varies between different chemotherapeutic agents and treatments. Examples of such chemotherapeutic agents and the recommended rest periods are given in the table below.

| Drug Class | Drug | Usual Dosage and Route |
| --- | --- | --- |
| Alkylating drugs | Mechlorethamine (nitrogen mustard) | 6 mg/m$^2$ IV |
| | Chlorambucil (Leukeran) | 4-10 mb/day po |
| | Cyclophosphamide (Cytokxan) | 600 mg/m$^2$/IV<br>50-200 mg/m$^2$ po |
| | Melphan (Alkeran) | 1 mg/kg po q 4 wk |
| | Ifosfamide (Ifex) | 2-4 g/m$^2$/day<br>IV × 3-5 days<br>q 3-4 wk |
| Antimetabolites<br>Folate antagonist | Methotrexate | 2.5-5.0 mg/day po<br>25-50 mg/1 dose/wk po<br>100-10,000 Mg/m$^2$<br>IV (with rescue) |
| Purine antagonist | 6-Mercaptopurine | 100 mg/m$^2$/day |
| Pyrimidine antagonist | 5-Fluorouracil | po<br>300-1000/m$^2$ IV or continuous infustion |
| | Cytarabine | 100 mg/m$^2$ IV continuous infusion |
| | Gemcitabine (Gemzar) | 1200 g/m$^2$/wk IV |
| Spindle poison (from plants) Vincas | Vinblastine (Velban | 0.1-0.2 mg/kg IV q 7-10 days |
| | Vincristine (Oncovin) | 1.4 mg/m$^2$/wk IV |
| | Vinorelbine (Navelbine) | 20 mg/m$^2$/wk IV |
| | Paclitaxel (Taxol) | 135 mg-200 g/mL IV q3 wk |
| | Docetaxel (Taxotere) | 100 g/m$^2$ IV q 3 wk |
| Podophyllotoxins | Etoposide (VePesid) | 100 mg/m$^2$/day IV for 3-5 days 100 mg/day po for 14 days/mo |
| | Irinotecan (Camptosar) | 100-125 g/m$^2$ IV wk IV |
| | Topotecan (Hycamtin) | 1.5 g/m$^2$ IV daily × 5 days q 3-4 wk |
| Antibiotics | Doxorubicin (Adrianmycin) | 40-75 mg/m$^2$ rapidly IV or 30 mg/m/day for 3 days by continuous IV |

| Drug Class | Drug | Usual Dosage and Route |
|---|---|---|
| | Bleomycin (Blenoxane) | 6-15 U/m² sc or IV |
| | Mitomycin | Usually 10 to 12 mg/m², slowly IV |
| Nitrosoureas | Carmustine (BiCNU) | 150-200 mg/m² IV q 6 wk |
| | Lomustine (CeeNU) | 100-130 mg/m² po q 6 wk |
| Inorganic ions | Cisplatin (Platinol) | 60-100 mg/m² IV or 20 mg/m² IV daily × 5 days |
| | Carboplatin (Paraplatin) | 300 g/m² or target area under the curve of 5-6 IV q 3 wk |

It is understood that a treatment, consisting of a number of cycles and defined rest periods might vary also among different patients. Furthermore, such treatment might vary for different combinations and mixtures of chemotherapeutic agent. A skilled person will select the suitable number of cycles and rest periods for each patient and chemotherapeutic agent or chemotherapeutic agent combination.

The regimes of administration of antigen and chemotherapeutic agent or agents according to the present invention are adapted to the specific agent and agent combinations used. It is understood that a full treatment employing the compositions, methods and uses of the present invention could span a number of separate chemotherapy cycles. It is further understood that the treatment patterns could be repeated any number of times as required. In particular, the compositions, methods and uses of the present invention cover administration of vaccines prior to and/or, during and/or after administration of a chemotherapeutic agent, a chemotherapeutic cycle or an entire chemotherapeutic treatment of several cycles in accordance with the chemotherapeutic agent/vaccine combination chosen. It is further understood that the compositions, methods and uses according to the present invention are used within a treatment regime which includes also other treatments such as surgery and/or radiotherapy.

Preferably the antigen would be administered during rest periods within or after chemotherapy cycles. Timing could be optimised by measuring the reduction of Treg levels or Treg function during each chemotherapeutic treatment.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

For example, suitable doses for the administration of the chemotherapeutic regimes FOLFOX and IFL are set out in the examples section herein. In addition, suitable regimes for the administration of these regimes in combination with administration of a tumour antigen are set out herein.

The invention is further described, for the purposes of illustration only, in the following examples in which reference is made to the following Figures.

FIG. 1 shows a diagrammatic of the vaccination and monitoring regime described in the Examples section.

Figure 2:
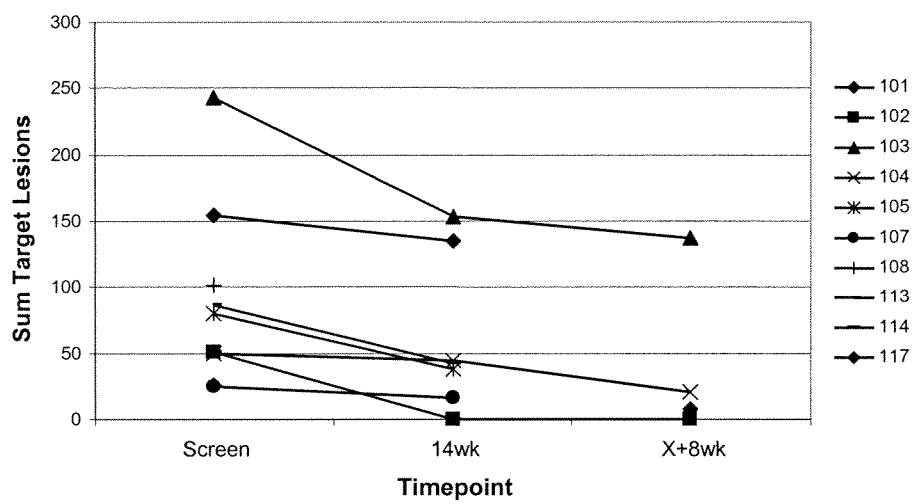

FIG. 2: TV2-FOLFOX: Tumour dimensions throughout the clinical trial time course. The figure illustrates the sum of the target tumour lesions for evaluable patients at 3 CT scan time points (prior to TroVax vaccination (screen) and at weeks 14 and X+8).

Figure 3:
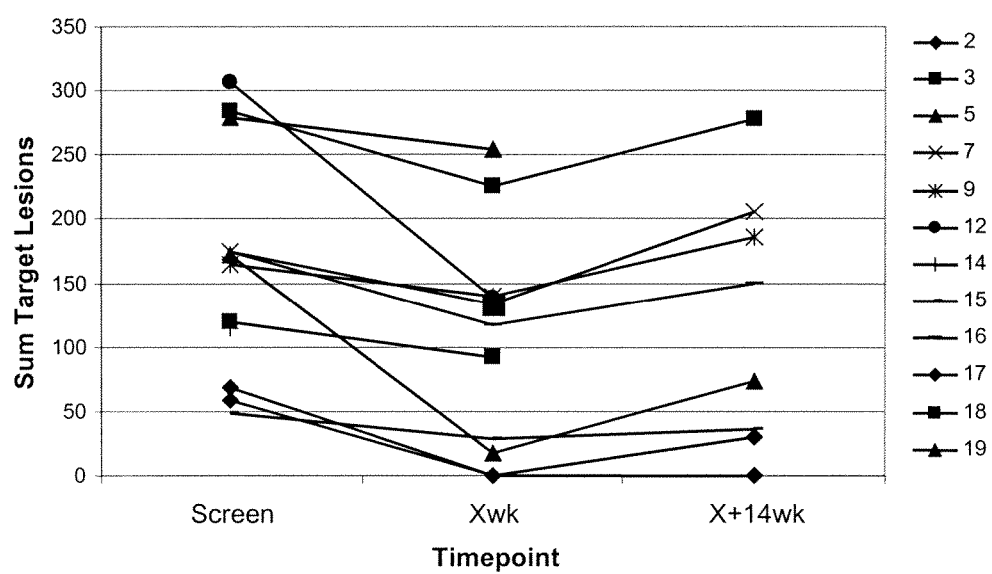

FIG. 3 TV2-IFL: Tumour dimensions throughout the clinical trial time course. The figure illustrates the sum of the target tumour lesions at 3 time points: prior to TroVax vaccination (screen) and at weeks X and X+14.

Figure 5:
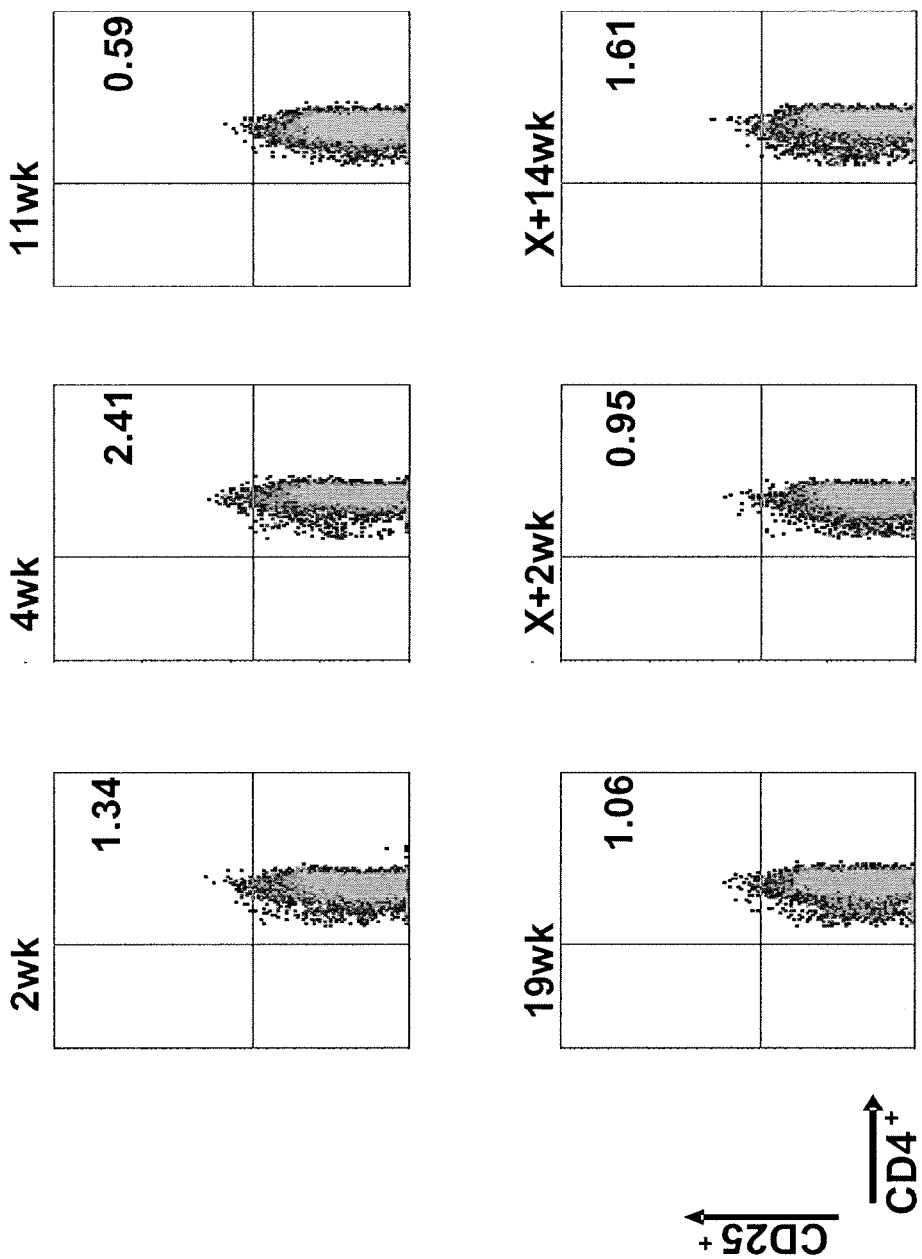

FIG. 4a shows 5T4 Responses in TV2-IFL, FIG. 4b shows 5T4 Responses in TV2-FOLFOX, FIG. 4c shows MVA Responses in TV2-IFL, FIG. 4d shows MVA Responses in TV2-FOLFOX, FIG. 4e shows TT Responses in TV2-IFL and FIG. 4f shows TT Responses in TV2-FOLFOX FIG. 5 Percentages of $CD4^+CD25^+$ Tregs (right hand quadrant) for patient TV2-016 at various time points during the TV2 trial. Results are shown as the percentage of $CD4^+$ T cells.

Figure 6:
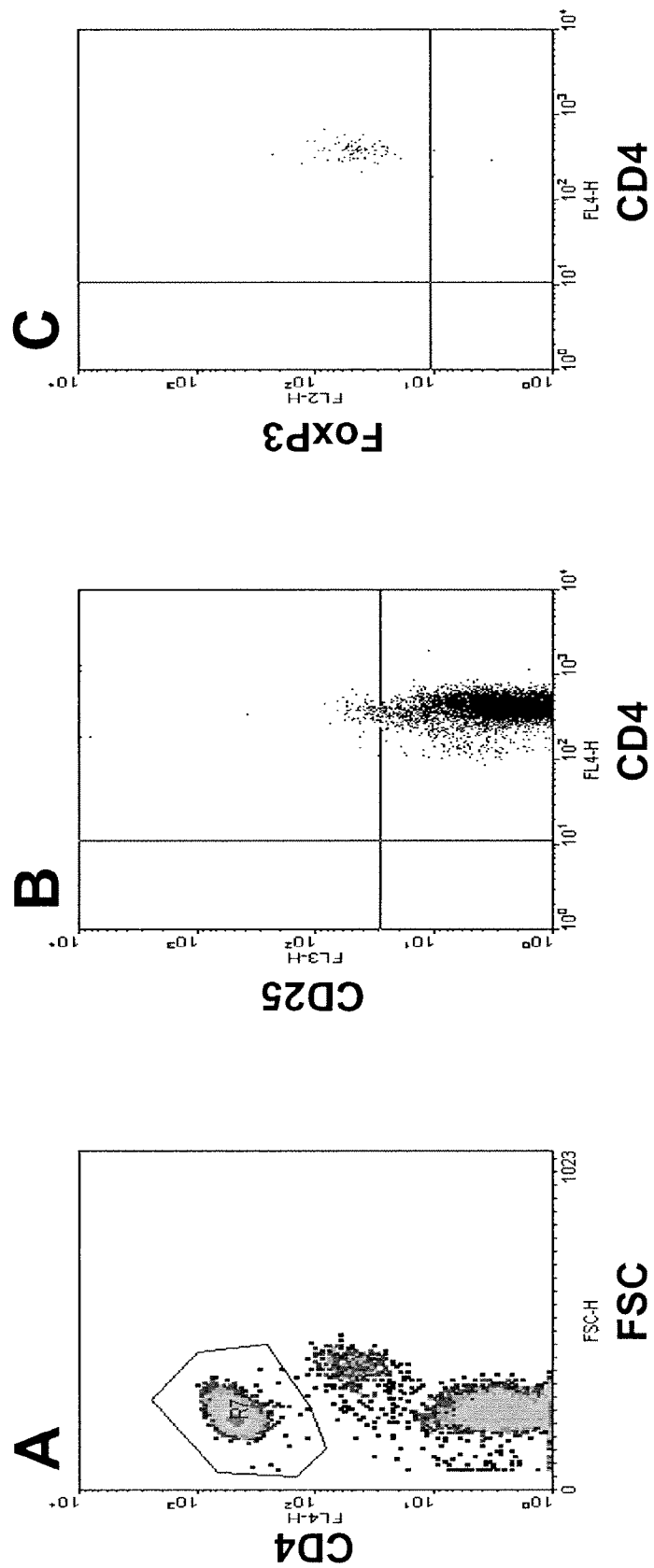

FIG. 6 Confirmation of $CD4^+CD25^+$ Treg phenotype by staining for intracellular FoxP3 expression. $CD4^+$ T cells were gated (A) and their CD25 expression ascertained (B). $CD25^{+hi}$ expressers were selected by setting a strict quadrant (B; top right quadrant). The cells in this right hand quadrant were gated and most expressed FoxP3 (C; top right hand quadrant).

Figure 7:
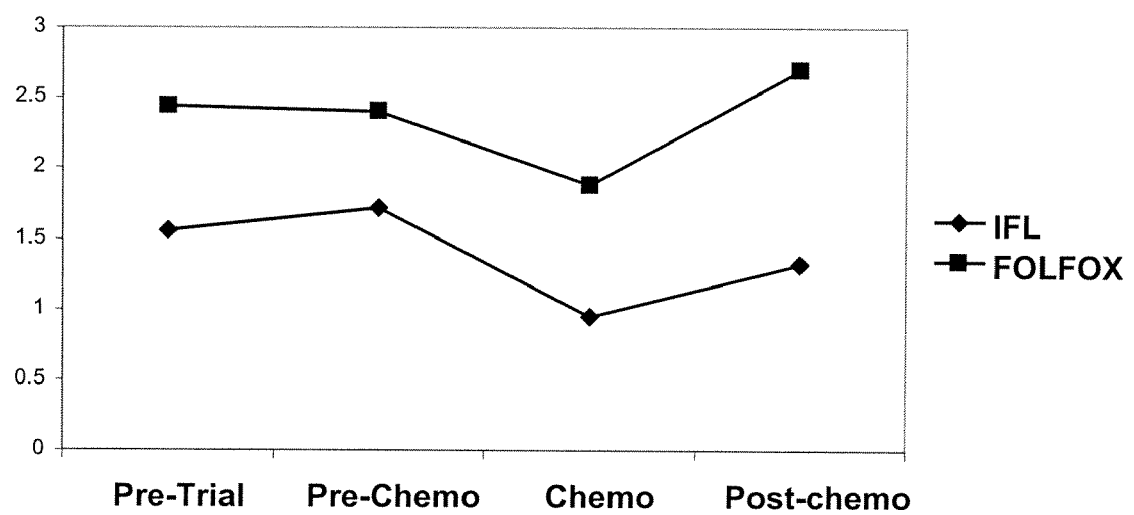

FIG. 7. The mean percentage of $CD4^+CD25^+$ Tregs within the $CD4^+$ T cell population for TV2-IFL (black n=7) and –FOLFOX (grey n=6) patients.

EXAMPLES

Summary

These examples summarise the kinetics of immune responses detected in both TV2 IFL and FOLFOX trials and investigates relationships between clinical and immunological responses.

Immune Responses and Kinetics

All evaluable patients in both TV2 IFL (n=12) and FOLFOX (n=11) clinical trials mounted 5T4 specific cellular and/or humoral immune responses as detailed below:

| Trial (Nos. evaluable patients) | Nos patients showing 5T4 specific immune responses | | | |
|---|---|---|---|---|
| | ELISA | Proliferation | ELISPOT | Any Assay |
| IFL (n = 12) | 10 (83%) | 10 (83%) | 11 (92%) | 12 (100%) |
| FOLFOX (n = 11) | 10 (91%) | 10 (91%) | 10 (91%) | 11 (100%) |

In both trials, mean antibody titres increased following each of the 6 vaccinations (compared to the previous sampling time point).

In the FOLFOX trial, mean antibody titres during chemotherapy (weeks 4-19) were comparable to post-chemotherapy (weeks X+2-X+10). However, in the IFL trial, mean antibody titres during chemotherapy were significantly lower than post-chemotherapy suggesting that the IFL chemotherapy regimen may effect on antibody responses.

In both trials, the greatest mean antibody titre occurred at week X+8 i.e. following the 6 h immunisation.

Mean 5T4 proliferative responses showed little or no increase following any of the 6 vaccinations, although individual patients did show increases.

In both trials, proliferative responses were greatest following completion of chemotherapy compared to during chemotherapy.

In both trials, 5T4 specific proliferative responses showed a significant increase between weeks 19 and X+2; this was not the case for MVA or TT responses suggesting that both chemotherapy regimes impact on the detection of proliferative responses to a self antigen but not to foreign antigens ex vivo.

In general, patients enrolled into the TV2 trials mounted 5T4 specific cellular and humoral immune responses of greater magnitude and longevity than seen in an earlier trial (TV1) in which patients recruited onto a TroVax® monotherapy trial had been previously treated with chemotherapy some time before TroVax was administered.

Clinical Responses

Possible trends relating 5T4 specific immune responses with clinical response were investigated by ranking the magnitude of each patients' immune response alongside their reported tumour response.

TV2-FOLFOX: The data presented indicates that high 5T4 specific antibody titres and ELISPOT (but not proliferative) responses are associated more frequently with complete and partial responses than with stable or progressive disease.

This observation is consistent when responses are analysed over the entire monitoring timecourse, during and post chemotherapy. If data from both ELISA and ELISPOT are integrated and the magnitude of the combined responses tabulated alongside clinical responses, higher scores cluster more frequently with positive tumour responses (CR+PR). Patients classified as SD or PD at 14 wk or X+8 wk have the lowest combined scores. Combining ELISA and ELISPOT data yields stronger trends than each assay analysed individually.

TV2-IFL: Strong immune responses in the IFL trial occurred primarily following completion of chemotherapy. Clinical benefit will be assessed by monitoring survival and making comparisons between immunological responses and overall survival will be investigated once the data are available.

Data Analysis: Analysis of Immune Response Kinetics a. Within each trial, only data from evaluable (per protocol) patients have been analysed.

b. All data are presented in a similar manner. Antigen specific responses are tabulated for each evaluable patient at each time point analysed. In addition, the mean antigen-specific immune responses are tabulated on a population basis for each trial at:

1. EACH time point
2. Prior to vaccination (weeks −2 and 0)
3. During chemotherapy (weeks 4-19)
4. Post-chemotherapy (weeks X+2 to X+14 (IFL) or X+10 (FOLFOX))

It should be stated that 2 TroVax injections occur during chemotherapy and 2 following completion of chemotherapy. Furthermore, the 15 week time period during chemo includes 6 blood sampling time points. Following completion of chemotherapy, IFL patients are monitored for 14 weeks which also includes 6 sampling time points. FOLFOX patients are monitored for 10 weeks following completion of chemotherapy and this comprises 5 sampling time points.

c. The FOLD increase in immune response after each vaccination is tabulated.

In addition, the fold increase between weeks 19 and X+2 (i.e. the end of chemotherapy and following completion of chemotherapy) is also noted.

Data Analysis: Analysis of Correlates Between Immune Response and Tumour Response The MEAN 5T4 specific immune responses have been determined for all evaluable patients for each of the 3 core immuno-monitoring assays (ELISA, proliferation and ELISPOT). Responses have been ranked in ascending order and compared against the respective tumour responses (some CT scans are outstanding). Mean 5T4 specific immune responses were determined over 3 time periods: (i) Over all post TroVax time points i.e. from week 2 to week X+10 for FOLFOX patients and week 2 to X+14 for IFL patients, (ii) Over all post-TroVax time points occurring during the period of chemotherapy (weeks 4-19) and (iii) over all post-TroVax time points occurring following completion of chemotherapy (weeks X+2 to X+10 for FOLFOX or X+14 for IFL).

Furthermore, 5T4 specific ELISPOT, proliferation and antibody responses were integrated and compared against the reported clinical responses.

To achieve this, each evaluable patient was simply scored relative to the magnitude of the greatest immune response detected. For example, the patient with the highest mean 5T4 antibody titre across the selected monitoring period (i.e. all post TroVax time points, during chemo, post chemo) was given a score of 100%, all other patients were scored as a percentage of the greatest response. To integrate the assays, the scores per assay for each patient were simply summed. Such an analysis does take into consideration the magnitude of the patients' immune responses but gives equal "weight" to all assays.

Methods and Protocols

Trovax+FOLFOX

A phase II clinical trial for an open label study of TroVax given in conjunction with 5-fluorouracil/leukovorin/oxaliplatin (FOLFOX) was conducted for determining safety and immunogenicity before, during and after chemotherapy.

a) Study Design

This is an open label administration of up to six injections of TroVax in conjunction with a standard schedule of 5-FU/oxaliplatin/leukovorin in patients with advanced colorectal cancer. A total of fifteen patients are enrolled in order to obtain 10 evaluable patients. The dosage regimen is two injections, given before chemotherapy, two during chemotherapy (assumed to last for up to 6 months) and two injections after chemotherapy has ceased. Patients could be on study for a maximum of 40 weeks to assess tolerability of the treatment regimen, induction of humoural and cellular immunity to 5T4 cell surface antigen, and immune response to the vector b) Treatment Trovax Patients are immunised with a single intramuscular injection of Trovax 10× at weeks 0, 2, 11, 17, and 2 and 6 weeks after last dose of chemotherapy Oxaliplatin/5-FU/Leukovorin Patients commence chemotherapy at week 4. The chemotherapy is given at 2 weekly intervals for 12 weeks (6 cycles, weeks 4, 6, 8, 10, 12, 14). An assessment of response is made in the week after completion of cycle 6 (week 14; CT/MRI scan). Further chemotherapy cycles (up to a maximum of 6 cycles, weeks 16, 18, 20, 22, 24, 26) are administered if deemed in the patient's interest by the investigator.

c) Concurrent Treatments

The 5-FU/leukovorin chemotherapy is given by the modified de Gramont regimen (MdG) along with oxaliplatin, (OxMdG).

The standard regimen given at the Leeds Teaching Hospitals NHS Trust is as follows;
1 Two hour infusion of leukovorin 175 mg (or 350 mg of racemic folinic acid) in 250 ml 5% dextrose.
2 Two hour infusion of oxaliplatin 85 mg/m$^2$ in 250 ml 5% dextrose.
5 minute bolus injection of 5-fluorouracil 400 mg/m$^2$.
4 46 hour infusion of 5-fluorouracil 2400 mg/m$^2$ given through a Baxter LV5 pump.

Antiemetics, including intravenous 5HT-3 antagonists and dexamethasone, are given prior to each cycle of chemotherapy. Oral antiemetic therapy, consisting of a three-day course of reducing doses of dexamethasone and domperidone, as required, is given to the patients. All antiemetic therapy required is recorded in the CRF.

TroVax+IFL a) Treatment Plan and Methods

Patients complying with the entry criteria are invited to enter the study. After giving fully informed consent, patients are subjected to a physical examination to document general fitness to proceed with the trial. If possible, tissue is obtained for determination of 5T4 status. At that time, metastases and/or local recurrence are documented using relevant CT scans and the level of CEA (5 ml) surface antigen in blood is checked. Blood is drawn for haematology and clinical chemistry (10 ml), pituitary hormone screen (ACTH, TSH, LH, FSH; 10 ml), auto-antibodies (10 ml) and immunological testing (antibodies to 5T4 and vector, cellular responses to 5T4 and other antigens; 100 ml). This screen should not occur more than two weeks before the immunisation schedule begins.

At week 0 and week 2, the patients are immunised with a single intramuscular injection of TroVax. Before both injections, blood is again drawn for measurement of CEA and immunological testing (100 ml).

Patients commence chemotherapy at week 4. The chemotherapy continues at two weekly intervals for up to 12 months if the patients respond, although six months is the common duration of treatment. Blood is obtained prior to the dose of chemotherapy at weeks 4 and 6 for CEA and immunological testing (100 ml). Blood is obtained for haematology (5 ml) before each dose of chemotherapy.

Further injections with TroVax are given at weeks 11 and 17 (i.e. in the interval between doses of chemotherapy. Blood is drawn for CEA and immunological testing (100 ml) before each of these injections and two weeks later (weeks 13 and 19).

The chemotherapy then continues for as long as is decided appropriate by the patient's physician. At the end of chemotherapy, CT scan restaging of the disease are obtained. Two weeks after the chemotherapy ends (X+2 weeks), TroVax is again given by a single intramuscular injection. Before the injection and 2 weeks after that (X+4 weeks), blood is obtained for CEA and immunological testing (100 ml). A final injection is given four weeks after the previous injection (X+6 weeks). Before this injection and two (X+8 weeks) and four weeks (X+10 weeks) after that, blood is obtained for CEA and immunological testing (100 ml). A final follow up visit is conducted four weeks later (X+14 weeks).

b) Concurrent Treatments

De Gramont regimen: Patients receive leukovorin (200 mg/m$^2$/day) as a two-hour intravenous infusion, followed by 5-FU as an intravenous bolus at 400 mg/m$^2$/day, and then as a 22-hour continuous infusion at 600 mg/m$^2$/day, repeated on 2 consecutive days. Irinotecan (180 mg/m$^2$; 30-minute intravenous infusion) is administered on day 1, simultaneously with leucovorin administration. This cycle is repeated every 2 weeks.

Modified De Gramont: Patients receive leucovorin and bolus 5FU on day 1, followed by infusional 5FU over 46 hours.

Patients included in this trial may not be given any other anticancer treatments for the duration of the trial. A requirement for such treatment necessitates removal of the patient from the trial.

Medications intended to relieve symptoms are prescribed at the discretion of the Investigator and recorded in the Case Report Form (CRF). The patients should also keep a record of any over the counter medicines consumed and these should be noted in the CRF.

Immunomonitoring

The assays used to undertake the immuno-monitoring can be split into those which measure either cellular or humoral responses and are listed below:

Measurement of Cellular Responses

1. Proliferation Assay

This assay is performed using PBMCs processed from fresh blood and set up on the day of blood sampling.

The proliferation assay is based upon the ability of immune cells (primarily CD4$^+$ T cells) to respond to specific proteins. One of the ways in which a T cell will respond following interaction with its target protein, is by rapid cell division. The response to such stimuli can simply be measured by counting the number of cells present in a culture before and after the addition of a stimulating agent. However, this can be both laborious and difficult since the responding cells may constitute only a small proportion of the total cell population. In practice therefore, any enhanced cell division is measured by the incorporation of $^3$H-Thymidine into cellular DNA, a process which is closely related to underlying changes in cell number. The proliferative responses induced by a test protein can be compared to that induced by medium alone (no stimulation control). The data are transformed to yield a stimulation index (S.I.) which is defined as: "Mean CPM of PBMCs incubated with test antigen divided by the mean CPM of PBMCs incubated with medium alone". This relative measure of cellular activity is widely utilised to enable comparisons between samples taken during longitudinal studies (e.g. patients enrolled in clinical trials) and to handle differences in the background proliferation to medium alone.

Preparation of plasma and PBMCs from whole blood and measurement of antigen specific proliferative responses in clinical samples were according to standard techniques using a cell harvester and TopCount. Methods are described, for example, in Braybrooke J P, Slade A, Deplanque G, et al: Phase I study of MetXia-P450 gene therapy and oral cyclophosphamide for patients with advanced breast cancer or melanoma. Clin Cancer Res 11:1512-1520, 2005 and Harrop R, Ryan M G, Golding H, et al: Monitoring of human immunological responses to vaccinia virus. Methods Mol Biol 269: 243-266, 2004.

2. ELISPOT

The enzyme linked immunospot (ELISPOT) assay was described more than 13 years ago for the detection of specific immune cells at the single cell level. The ELISPOT assay is used for a wide range of applications including the monitoring of cellular responses in patients with cancer undergoing immunotherapeutic treatment. The IFNγ ELISPOT assay exhibits a high level of sensitivity that permits detection of <10 responding cells per million PBMCs. With this assay, it is possible to detect memory T cells functionally responding to an antigenic stimulus through the secretion of the cytokine IFNγ. Furthermore, the IFNγ ELISPOT assay does not require the use of fresh cells or radioactive substances, making it a simpler and more transferable technique than other assays such as the Chromium release assay which has been traditionally used in vaccine trials to measure T cells responses.

An important advantage of the IFNγ ELISPOT is that it is a direct measurement of a Th1 cell-mediated immune response. As such, it is useful for monitoring the effectiveness of a vaccine to induce cell-mediated immunity. In addition, freshly collected or frozen PBMCs can be used for evaluation in the IFNγ ELISPOT. This is a distinct advantage in the analysis of samples taken from patients at multiple timepoints throughout a clinical trial program. The use of frozen PBMCs enables the batching of samples and hence reduces the overall variability of the assay. In addition, the availability of frozen test samples means that assays can be repeated.

PBMCs are plated into coated wells and incubated overnight at 37° C., 5% $CO_2$ with the appropriate antigen. After approximately 6 hours of co-culture, memory cells specific for the antigen begin to secrete IFNγ that is, in turn, captured by the membrane bound antibody. Thus, IFNγ binding occurs in the immediate environment surrounding the cytokine-secreting cell. After approximately 20 hours, the cells are washed off. Subsequently, the assay utilises two high affinity cytokine-specific antibodies directed against different epitopes on the same cytokine molecule. Spots are generated with a colourimetric reaction in which soluble substrate is cleaved, leaving an insoluble precipitate at the site of the reaction. The resulting spot represents a footprint of the original cytokine producing cell. The number of spots is a direct measurement of the frequency of cytokine producing T cells and the number of spots increases proportionately with the strength of the immune response. Activated $CD8^+$ T Cells, $CD4^+$ helper T cells and NK cells secrete this cytokine. Comparison of the frequency of antigen-specific T cells before, during and after an immunisation cycle should reflect the relative immunogenicity of the vaccine being evaluated.

Preparation of plasma and PBMCs from whole blood and measurement of cellular immune responses to vectors in clinical trial samples were performed by ELISPOT using an automated ELISPOT plate reader following standard protocols as described, for example, in Braybrooke J P, Slade A, Deplanque G, et al: Phase I study of MetXia-P450 gene therapy and oral cyclophosphamide for patients with advanced breast cancer or melanoma Clin Cancer Res 11:1512-1520, 2005. Harrop R, Ryan M G, Golding H, et al: Monitoring of human immunological responses to vaccinia virus. Methods Mol Biol 269:243-266, 2004.

Measurement of Humoral Responses (ELISA)

The enzyme linked immunosorbent assay (ELISA) is based upon the ability of antibodies to bind their target protein in a highly specific manner. The analysis of antigen-specific antibody responses by ELISA is a widely utilised and well-established technique. The assay can be used to provide a relative measure of antigen-specific antibody concentrations in serum (or other fluids). One of the many applications of the technique is to monitor antibody levels following vaccination to determine whether treatment increases the concentration of the antibody of interest.

To measure the antigen specific antibody response, the target protein is bound to the surface of a 96-well ELISA plate. Following a blocking step (to minimise non-specific binding of antibodies directly to the plastic), plasma is added to the plate and incubated at room temperature. Each well is then washed to further minimise non-specific binding of antibodies. A secondary antibody, specific for the species of the test serum (e.g. anti-human), is added to each well. The secondary antibody is conjugated to an enzyme (e.g. peroxidase) which, upon incubation with a chromogenic substrate (e.g. OPD) catalyzes its conversion into a coloured, soluble product which can be quantified using a spectrophotometer. Generally, the greater the colour change the greater the concentration of antibody present in the test serum Preparation of plasma and PBMCs from Whole Blood and Measurement of Antigen specific antibody titres were performed by ELISA following standard techniques and using a Dynex MRX plate reader for immunological assays along with a Dynex plate washer in accordance with the manufacturers instructions. Suitable methods are described, for example, in Braybrooke J P, Slade A, Deplanque G, et al: Phase I study of MetXia-P450 gene therapy and oral cyclophosphamide for patients with advanced breast cancer or melanoma. Clin Cancer Res 11:1512-1520, 2005. Harrop R, Ryan M G, Golding H, et al: Monitoring of human immunological responses to vaccinia virus. Methods Mol Biol 269: 243-266, 2004.

Assay Controls

For the measurement of antibody responses by ELISA, pooled human plasma recovered from 5 healthy donors is used as a negative control. As a positive control, plasma recovered from patients enrolled in previous clinical trials (patient TV1-102 (10 wk) or patient BC2-102 from TV1 or BC2 clinical trials respectively) is used. Both negative and positive control plasma are included on all assay plates and "pass/fail" acceptance criteria applied to each plate.

Acceptance criteria/Statistical methods to be used.

Assay acceptance criteria and data handling are followed. A positive immune response due to vaccination is defined separately for each assay as detailed below:

ELISA

Antibody titre is defined as the greatest dilution of plasma at which the mean optical density (O.D.) of the test plasma is ≧2 fold the mean O.D. of the negative control (normal human serum; NHS) at the same dilution.

A positive 5T4 specific antibody response induced by vaccination will be reported if:
   a. The antibody titre compared to NHS is ≧10 and
   b. The post-injection antibody titre is ≧2 fold the antibody titre determined at both of the pre-injection time-points.

Proliferation Assay

Results from proliferation assays will be reported as a stimulation index (S.I.) which is defined as:

$$S.I. = \frac{\text{Incorporation of } ^3\text{H-Thymidine by } PBMCs \text{ cultured with test antigen}}{\text{Incorporation of } ^3\text{H-Thymidine by } PBMCs \text{ cultured with medium alone}}$$

A positive 5T4 proliferative response induced by vaccination will be reported if:
   a. The stimulation index (S.I.) to the 5T4 antigen (protein or peptide) is ≧2 and
   b. The C.V. of replicates containing the 5T4 antigen is <100% and
   c. The S.I. induced by the 5T4 antigen after immunisation is ≧2 fold greater than the
      highest S.I. induced by the antigen at either of the pre-injection time-points.

ELISPOT

A positive 5T4 ELISPOT response induced by vaccination will be reported if:
   a. The mean spot forming units (SFU)/well in response to a 5T4 antigen (protein or peptide) is ≧3 fold the mean SFU/well in wells containing medium alone and
   b. The mean SFU/well in response to a 5T4 antigen is ≧10 and c. The 5T4 antigen specific precursor frequency (number of antigen specific cells per $10^6$ total PBMCs), after immunisation is $\geq 2$ fold the precursor frequency at either of the pre-injection time-points.

Results

1. TV2-FOLFOX 1.1 Source Clinical and Patient Data

Seventeen patients were recruited into the TV2-FOLFOX trial of whom 11 became evaluable for assessment of immunological responses (Table 1).

TABLE 1

Clinical Data.

| Patient ID | Alive/Dead | Tumour Response | | Sum Target Lesions | | | Survival (weeks from wk 0) |
|---|---|---|---|---|---|---|---|
| | | 14 wk | X + 8 wk | Screen | 14 wk | X + 8 wk | |
| 101 | Alive | PR | PR | 26 | Too small | 8 | 91 |
| 102 | Dead | CR | CR | 51 | 0 | 0 | 58 |
| 103 | Alive | PR | PR | 243 | 153 | 137 | 78 |
| 104 | Alive | SD | PD | 50 | 44 | 20 | 70 |
| 105 | Dead | PR | SD | 80 | 38 | | 53 |
| 106 | Alive | NE | NE | 69 | NE | NE | 67 |
| 107 | Alive | PR | PD | 25 | 16 | | 63 |
| 108 | Alive | CR | CR | 101 | N/A | | 61 |
| 109 | Dead | WD | 0 | WD | WD | WD | 5 |
| 110 | Alive | WD | 0 | WD | WD | WD | 60 |
| 111 | Dead | WD | NE | WD | WD | WD | 9 |
| 112 | Dead | NE | NE | ND | 150 | | 41 |
| 113 | Alive | PD | PD | 86 | 42 | | 54 |
| 114 | Alive | ??CR?? | 0 | 51 | 0 | | 52 |
| 115 | Dead | NE | 0 | 122 | N/A | | 37 |
| 116 | Alive | PR | 0 | 43 | 24 | | 50 |
| 117 | Alive | SD | 0 | 154 | 135 | | 50 |

All 17 ITT (intention to treat) patients are included in the table.
Evaluable patients (n = 11) are indicated by shading (survival data current to date).
Key: WD = Patient withdrawn therefore no result available; N/A = Measurement taken but not currently available.

FIG. 2 shows TV2-FOLFOX: Tumour dimensions throughout the clinical trial time course. The figure illustrates the sum of the target tumour lesions for evaluable patients at 3 CT scan time points (prior to TroVax vaccination (screen) and at weeks 14 and X+8).

Of the 11 evaluable patients, all showed a reduction in tumour burden at week 14. CT scans are only available for 4 patients at week X+8, all of which showed further decreases in tumour load compared to week 14.

1.2 Immunological Responses 1.2.1 Antibody Responses

5T4 specific antibody titres for each evaluable patient across the entire monitoring time course are illustrated in table 2.

Table 2: 5T4 specific antibody responses. Results are expressed as a 5T4 specific antibody titre (the greatest serum dilution at which the test sample has a mean O.D. (490 nm) $\geq 2$ fold that of the negative control sample (normal human serum; NHS)) at each sampling time point. Results tabulated in bold which have $\geq 10$ represent positive antibody responses. Mean titres are reported for all patients at each time point and also at multiple time points pre-vaccination, during chemotherapy and post chemo. In addition, the fold increase in mean antibody titre compared to the previous time point is shown after each vaccination.

TABLE 2

| Patient No | 5T4 Specific Antibody Titre at Timepoints (weeks) Post Primary Immunisation | | | | | | | | | | | | | |
|---|---|---|---|---|---|---|---|---|---|---|---|---|---|---|
| | −2 | 0 | 2 | 4 | 6 | 11 | 13 | 17 | 19 | X + 2 | X + 4 | X + 6 | X + 8 | X + 10 |
| 101 | <10 | <10 | <10 | <10 | <10 | <10 | <10 | <10 | <10 | <10 | <10 | <10 | <10 | <10 |
| 102 | <10 | <10 | 10 | 1280 | 80 | 40 | 40 | 20 | 40 | 20 | 80 | 80 | 80 | 80 |
| 103 | <10 | <10 | <10 | 80 | 20 | <10 | <10 | <10 | 20 | <10 | 20 | 20 | 320 | 320 |
| 104 | <10 | <10 | <10 | <10 | <10 | <10 | 10 | <10 | 10 | <10 | <10 | <10 | 40 | 20 |
| 105 | <10 | <10 | <10 | 40 | 10 | <10 | <10 | <10 | <10 | <10 | <10 | <10 | 160 | 80 |
| 107 | <10 | <10 | <10 | 160 | 1280 | 160 | 160 | 80 | 320 | <10 | 160 | 160 | 1280 | 160 |
| 108 | <10 | <10 | <10 | 40 | 40 | <10 | 1280 | 320 | 320 | 20 | 640 | 160 | 640 | 1280 |
| 113 | <10 | <10 | <10 | 160 | <10 | <10 | 20 | <10 | <10 | <10 | <10 | <10 | <10 | <10 |
| 114 | <10 | <10 | 20 | 320 | 160 | <10 | <10 | <10 | <10 | <10 | <10 | <10 | <10 | 10 |
| 116 | <10 | <10 | 10 | 20 | 20 | <10 | 10 | <10 | 80 | <10 | 80 | 40 | 80 | 40 |
| 117 | <10 | <10 | <10 | 10 | 10 | <10 | 10 | <10 | 40 | <10 | 20 | <10 | 160 | 80 |
| Mean Titre | <10 | <10 | 3.6 | 207 | 147.3 | 18.2 | 139.1 | 38.2 | 75.5 | 3.6 | 90.9 | 42 | 250.9 | 188.2 |
| Fold ↑ | | | 52 | | | 7.7 | | 2 | 0.05 | 23 | | | 3.7 | |
| Mean Titre | <10 | | 3.6 | | | 102.6 | | | | | | 115.1 | | |

Over the entire post-TroVax immuno-monitoring time course, the mean 5T4 specific antibody titre was 100. The majority of patients sero-converted by week 4 (i.e. following 2 TroVax vaccinations). The mean antibody titres in the FOL-FOX trial were high during chemotherapy (mean titre of 103), decreased following the completion of chemotherapy (between weeks 19 and X+2) and increased moderately following completion of chemotherapy (mean titre of 115). Increases in the mean antibody titre were seen after each of the 6 vaccinations.

1.2.2 Proliferative Responses

Tables 3 a-b detail antigen specific proliferative responses for each evaluable patient across the entire monitoring time course. The responses to 5T4 (3a) and MVA (3b) have been analysed. 5T4 represents the key antigen against which it is hoped to induce a potent and long-lived immune response. As the vector used to deliver 5T4, MVA represents a very useful "internal control" on which responses can be "benchmarked". Patients are expected to mount strong immune responses against MVA (a complex and foreign pathogen) and such responses can be compared, both in terms of their magnitude and kinetics, to those induced against 5T4.

Tables 3a-b: Summary proliferative responses of PBMCs recovered from patients following in vitro restimulation with 5T4 (a) and MVA (b). Results are expressed as a stimulation index (proliferation induced by medium alone÷proliferation induced by test antigen). A stimulation index $\geq 2$ (indicated by bold text) is considered to be a positive response at that time point. Proliferative responses which are positive (S.I.$\geq 2$) and at least 2 fold greater than the pre-injection (−2 or 0 week) responses are indicated in bold.

TABLE 3a

TV2-FOLFOX: Proliferative responses to 5T4

| Patient | Sampling Time points (weeks) | | | | | | | | | | | | |
|---|---|---|---|---|---|---|---|---|---|---|---|---|---|
| | −2 | 0 | 2 | 4 | 6 | 11 | 13 | 17 | 19 | X + 2 | X + 4 | X + 6 | X + 8 | X + 10 |
| 101 | 23.4 | 9.4 | 12 | 3.5 | 17 | 29.1 | 2 | 1.7 | 1.9 | 4.4 | 1.9 | 0.8 | 2.7 | 1.1 |
| 102 | 10.4 | 2.9 | 0.3 | 2.1 | 4.4 | 11 | 20.7 | 5.2 | 0.72 | 2.45 | 6.05 | 1.99 | 6.97 | 6.21 |
| 103 | 4.7 | 2.1 | 2.5 | 6.3 | 6.2 | 1.8 | 0.6 | 2.7 | 2.05 | 3.31 | 7.25 | 4.86 | 2.15 | 2.57 |
| 104 | 1.6 | 0.6 | 0.6 | 0.4 | 1 | 1.16 | 0.64 | 1.13 | 0.41 | 7.11 | 2.90 | 1.10 | 16.10 | 0.24 |
| 105 | 2.3 | 0.9 | 1.6 | 3.4 | 1.2 | 0.9 | 1.2 | 2.41 | 1.33 | 8.67 | 9.75 | 13.53 | 17.34 | 0.60 |
| 107 | 2.6 | 1 | 1.3 | 1.5 | 0.96 | 0.53 | 7.27 | 4.49 | 1.78 | 7.60 | 13.63 | 24.55 | 16.47 | 26.93 |
| 108 | 0.7 | 3.8 | 0.3 | 0.90 | 5.02 | 0.41 | 2.57 | 5.00 | 7.85 | 1.46 | 6.35 | 1.39 | 11.93 | 5.39 |
| 113 | 0.57 | 2.11 | 1.25 | 0.75 | 9.95 | 5.33 | 9.52 | 4.19 | 3.54 | 2.23 | 8.48 | 12.66 | 7.91 | 52.68 |
| 114 | 3.50 | 1.71 | 0.39 | 2.11 | 1.08 | 4.26 | 1.66 | 0.81 | 4.09 | 9.18 | 26.66 | 5.76 | 10.17 | 51.99 |
| 116 | 0.38 | 0.39 | 11.41 | 4.21 | 5.92 | 9.71 | 0.66 | 5.84 | 3.10 | 23.67 | 7.36 | 11.56 | 0.78 | 18.66 |
| 117 | 2.65 | 1.52 | 1.68 | 6.86 | 9.93 | 8.38 | 0.65 | 2.09 | 3.95 | 5.57 | 12.71 | 18.35 | 25.99 | 19.53 |
| Mean SI | 4.8 | 2.4 | 3 | 2.9 | 5.7 | 6.6 | 4.3 | 3.2 | 2.8 | 6.9 | 9.4 | 8.8 | 10.8 | 16.9 |
| Fold ↑ | | | 1.2 | 0.97 | | | 0.7 | | 0.9 | 2.5 | 1.4 | | 1.2 | |
| Mean SI | | 3.6 | | | | | 4.3 | | | | | 10.5 | | |

TABLE 3b

TV2-FOLFOX: Proliferative responses to MVA

| Patient | Sampling Time points (weeks) | | | | | | | | | | | | |
|---|---|---|---|---|---|---|---|---|---|---|---|---|---|
| | −2 | 0 | 2 | 4 | 6 | 11 | 13 | 17 | 19 | X + 2 | X + 4 | X + 6 | X + 8 | X + 10 |
| 101 | 4.7 | 2.8 | 69 | 26.7 | 23 | 7.8 | 2.7 | 1.1 | 15.6 | 3.7 | 0.7 | 1.1 | 2.0 | 14.2 |
| 102 | 1.5 | 1.3 | 6.3 | 6 | 3.2 | 5.6 | 6.5 | 5 | | 4.19 | 22.76 | 10.68 | 1.98 | 33.17 | 16.06 |
| 103 | 0.7 | 0.9 | 13.8 | 5.8 | 0.3 | 7.5 | 6.3 | 14.7 | 72.1 | 5.96 | 17.92 | 17.93 | 5.35 | 12.01 |
| 104 | 0.4 | 0.9 | 5.4 | 0.1 | 2.6 | 0.4 | 0.56 | 11.33 | 2.40 | 1.92 | 1.47 | 0.92 | 17.21 | 0.62 |
| 105 | 1.3 | 0.5 | 1 | 45.4 | 4.8 | 2.58 | 94.32 | 9.06 | 22.51 | 46.25 | 143.03 | 80.49 | 116.15 | 0.80 |
| 107 | 1.4 | 0.2 | 7 | 62.1 | 45.76 | 39.37 | 71.10 | 43.13 | 1.13 | 30.23 | 351.08 | 131.36 | 118.01 | 167.20 |
| 108 | 0.4 | 0.4 | 19.5 | 18.12 | 3.11 | 33.92 | 1.27 | 40.55 | 25.41 | 3.00 | 155.15 | 3.22 | 154.92 | 9.90 |
| 113 | 21.64 | 18.07 | 40.50 | 18.74 | 8.92 | 6.10 | 15.94 | 8.22 | 4.71 | 2.59 | 37.35 | 51.55 | 40.05 | 69.76 |
| 114 | 0.50 | 1.29 | 1.17 | 11.21 | 1.12 | 2.38 | 20.86 | 1.62 | 5.45 | 26.36 | 201.10 | 51.28 | 39.54 | 101.36 |
| 116 | 0.66 | 0.31 | 37.81 | 14.96 | 6.15 | 4.61 | 1.31 | 4.65 | 2.06 | 13.86 | 4.83 | 2.15 | 0.74 | 3.65 |
| 117 | 2.83 | 2.13 | 13.34 | 170.57 | 48.10 | 23.02 | 0.63 | 10.37 | 11.70 | 34.63 | 164.26 | 122.77 | 274.13 | 236.88 |
| Mean SI | 3.3 | 2.6 | 19.5 | 34.5 | 13.4 | 12.1 | 20.1 | 13.6 | 15.2 | 17.4 | 98.9 | 42.2 | 72.8 | 57.5 |
| Fold ↑ | | | 7.5 | 1.8 | | | 1.7 | | 1.1 | 1.1 | 5.7 | | 1.7 | |
| Mean SI | | 2.9 | | | | | 18.2 | | | | | 57.8 | | |

The mean proliferative responses to 5T4 and MVA show differences in both the magnitude and longevity of the response. Each antigen will be addressed in turn:

A. 5T4

For all evaluable FOLFOX patients, the mean 5T4 specific proliferative response was elevated following TroVax vaccination compared to pre-injection (6.8 compared to 3.6). Such responses were stronger following completion of chemotherapy compared to during chemotherapy (10.5 compared to 4.3 respectively). This differential is most marked between weeks 19 and X+2 i.e. between the last time point at which most patients were still receiving chemotherapy and the first time point following completion of chemotherapy. This observation was particularly unexpected because patients did not receive a vaccination within this period (the last vaccination was at week 17). FOLFOX patients showed a 2.5 fold increase in mean proliferative responses between weeks 19 and X+2, which was the greatest fold increase observed between consecutive time points, being greater than following any of the 6 vaccinations. Very small increases in the mean 5T4 proliferative responses were detected in the FOLFOX trial following the 1st, 5th and 6th vaccinations but not at vaccinations given during chemotherapy.

B. MVA

As expected, the mean proliferative responses to MVA were of greater magnitude than the corresponding 5T4 responses. The mean MVA specific proliferative response following TroVax vaccination was 35 compared to a pre-injection SI of 2.9. The MVA specific proliferative responses were greater following completion of chemotherapy than during chemotherapy (57.8 compared to 18.2 respectively), a similar increase was seen with 5T4. However, unlike 5T4, there was little difference in the proliferative responses detected at weeks 19 and X+2.

1.3 Comparisons of Immunological and Clinical Responses 1.3.1 Summary Immunological Responses Across All Assays

TABLE 4

Summary immune responses detected in all evaluable patients

| Patient ID | Tumour Response 14 wk | Tumour Response X + 8 wk | Anecdotal Immunological Responses |
|---|---|---|---|
| 101 | PR | PR | ELISA: No 5T4 Abs<br>PROLIF: No response cf screen<br>ELISPOT: Very strong to protein, Weak to Pep pool #5 |
| 102 | CR | CR | ELISA: Very strong, commencing early and sustained<br>PROLIF: No response cf screen<br>ELISPOT: Very strong to protein and Class I and II pep |
| 103 | PR | PR | ELISA: Moderate, commencing early, increasing after Cx<br>PROLIF: No response cf screen<br>ELISPOT: Weak |
| 104 | SD | PD | ELISA: Weak<br>PROLIF: Moderate and transient post-chemo<br>ELISPOT: Weak |
| 105 | PR | SD | ELISA: Weak, increasing after Cx<br>PROLIF: Good post-chemo<br>ELISPOT: Very strong to Class I peps |
| 107 | PR | NA | ELISA: Very strong, commencing early and sustained<br>PROLIF: Strong post-chemo<br>ELISPOT: Strong and sustained to Class I peps |
| 108 | CR | CR | ELISA: Very strong, commencing early and sustained<br>PROLIF: Moderate and transient<br>ELISPOT: Very strong post chemo to protein and Class I pep |
| 113 | PD | PD | ELISA: Weak and transient<br>PROLIF: Strong and sustained<br>ELISPOT: Very Weak |
| 114 | CR | NA | ELISA: Moderate early but not sustained<br>PROLIF: Strong post-chemo<br>ELISPOT: Weak to protein |
| 116 | PR | NA | ELISA: Moderate Ab response pre, during and post Cx<br>PROLIF: Very strong and sustained throughout<br>ELISPOT: Weak pre and post-Cx |
| 117 | SD | NA | ELISA: Weak<br>PROLIF: Storng and sustained<br>ELISPOT: No response |

1.32 Analysis of Antibody Responses Versus Clinical Responses

The MEAN 5T4 antibody titres in all evaluable patients was compared against the reported clinical responses. The mean 5T4 antibody titre was determined over 3 time periods: (i) Over all post TroVax time points i.e. from week 2 to week X+10 (or the last data point available), (ii) Over all post-TroVax time points occurring during the period of chemotherapy (weeks 4-19) and (iii) over all post-TroVax time points occurring following completion of chemotherapy (weeks X+2 to X+10).

Tables 5a-5c: The tables illustrate the mean 5T4 antibody titres over the entire monitoring period (weeks 2–X+10; Table 5a), during chemotherapy (weeks 4-19; Table 5b) and following completion of chemotherapy (weeks X to X+10; Table 5c). The mean titres are ranked from LOWEST to HIGHEST alongside the clinical response attributed to that patient at weeks 14 and X+8.

TABLE 5a

Entire time course
Mean Post TroVax 5T4 Titres v Tumour Resopnse

| Patient | Titre | 14 wk | X + 8 wk |
|---|---|---|---|
| 101 | 0.0 | PR | PR |
| 104 | 6.7 | SD | PD |
| 113 | 15.0 | PD | PD |
| 105 | 22.7 | PR | SD |
| 117 | 27.5 | SD | 0 |
| 116 | 31.7 | PR | 0 |
| 114 | 42.5 | CR | 0 |
| 103 | 66.7 | PR | PR |
| 102 | 154.2 | CR | CR |
| 107 | 326.7 | PR | 0 |
| 108 | 395.0 | CR | CR |

TABLE 5b

During chemotherapy
Mean Post TroVax During Chemo 5T4 Titres v Tumour Resopnse

| Patient | Titre | 14 wk | X + 8 wk |
|---|---|---|---|
| 101 | 0.0 | PR | PR |
| 105 | 2.0 | PR | SD |
| 104 | 3.3 | SD | PD |
| 117 | 11.7 | SD | 0 |
| 103 | 20.0 | PR | PR |
| 116 | 21.7 | PR | 0 |
| 113 | 30.0 | PD | PD |
| 114 | 80.0 | CR | 0 |
| 102 | 250.0 | CR | CR |
| 108 | 333.3 | CR | CR |
| 107 | 360.0 | PR | 0 |

TABLE 5c

Post chemotherapy
Mean Post TroVax Post Chemo 5T4 Titres v Tumour Resopnse

| Patient | Titre | 14 wk | X + 8 wk |
|---|---|---|---|
| 101 | 0 | PR | PR |
| 113 | 0 | PD | PD |
| 114 | 2 | CR | 0 |
| 104 | 12 | SD | PD |
| 105 | 48 | PR | SD |
| 116 | 48 | PR | 0 |
| 117 | 52 | SD | 0 |
| 102 | 68 | CR | CR |
| 103 | 136 | PR | PR |
| 107 | 352 | PR | 0 |
| 108 | 548 | CR | CR |

It can be seen that patients with CRs (and many with PRs) fall in the bottom half of the tables i.e. have higher mean 5T4 antibody titres than those patients with SD or PD. In table 14c, the post-chemotherapy 5T4 titres are reported alongside the tumour responses at week X+8. A number of X+8 wk CT scans are outstanding, but it can be seen that patients with CRs and PRs are clustered at the bottom of the table (i.e. have high post-chemo Ab titres). The main patient who does not fit with this pattern is patient 101 who did not mount an antibody response or proliferative response to 5T4 but showed a strong ELISPOT response to 5T4 protein post chemotherapy and a moderate response to a class I peptide.

1.3.3 Analysis of Proliferative Responses versus Clinical Responses

The MEAN 5T4 proliferative responses (SIs) in all evaluable patients were compared against the reported clinical responses (some CT scans are outstanding). The mean proliferative responses were determined over 3 time periods (the entire monitoring timecourse, during chemotherapy and following completion of chemotherapy) and are tabulated in tables 6 a-c.

Tables 6a-6c: The tables illustrate the mean 5T4 proliferative responses over 3 different time periods: Table 6a the entire monitoring period (weeks 2-X+10), Table 6b during chemotherapy (weeks 4-19) and Table 6c following completion of chemotherapy (weeks X to X+10). The mean proliferative responses are ranked from LOWEST to HIGHEST alongside the clinical response attributed to that patient at weeks 14 and X+8.

TABLE 6a

Entire time Course
Mean Post TroVax 5T4 Sis v Tumour Resopnse

| Patient | SI | 14 wk | X + 8 wk |
|---|---|---|---|
| 104 | 2.73 | SD | PD |
| 103 | 3.52 | PR | PR |
| 108 | 4.05 | CR | CR |
| 105 | 5.16 | PR | SD |
| 102 | 5.67 | CR | CR |
| 101 | 6.51 | PR | PR |
| 116 | 8.34 | PR | 0 |
| 107 | 8.92 | PR | 0 |
| 117 | 9.64 | SD | 0 |
| 114 | 9.85 | CR | 0 |
| 113 | 9.87 | PD | PD |

TABLE 6b

During chemotherapy
Mean Post TroVax During Chemo 5T4 SIs v Tumour Resopnse

| Patient | SI | 14 wk | X + 8 wk |
|---|---|---|---|
| 104 | 0.79 | SD | PD |
| 105 | 1.74 | PR | SD |
| 114 | 2.34 | CR | 0 |
| 107 | 2.76 | PR | 0 |
| 103 | 3.28 | PR | PR |
| 108 | 3.63 | CR | CR |
| 116 | 4.91 | PR | 0 |
| 117 | 5.31 | SD | 0 |
| 113 | 5.55 | PD | PD |
| 102 | 7.35 | CR | CR |
| 101 | 9.20 | PR | PR |

TABLE 6c

Post chemotherapy
Mean Post TroVax Post Chemo 5T4 SIs v Tumour Resopnse

| Patient | SI | 14 wk | X + 8 wk |
|---|---|---|---|
| 101 | 2.18 | PR | PR |
| 103 | 4.03 | PR | PR |
| 102 | 4.73 | CR | CR |
| 108 | 5.30 | CR | CR |
| 104 | 5.49 | SD | PD |
| 105 | 9.98 | PR | SD |
| 116 | 14.20 | PR | 0 |

TABLE 6c-continued

Post chemotherapy
Mean Post TroVax Post Chemo 5T4 SIs v
Tumour Resopnse

| Patient | SI | 14 wk | X + 8 wk |
|---|---|---|---|
| 117 | 16.43 | SD | 0 |
| 113 | 16.79 | PD | PD |
| 107 | 17.84 | PR | 0 |
| 114 | 20.75 | CR | 0 |

Proliferative responses in this patient group were low during chemotherapy compared to post-chemotherapy (mean SIs of 4.3 compared to 10.4). Furthermore, the greatest mean proliferative response occurred at week X+10. A potent proliferative response at this time would not impact on tumour responses detected at week X+8, but may have a positive effect on patient survival. Such calculations will be undertaken as the data become available.

1.3.4 Analysis of ELISPOT Versus Clinical Responses

The MEAN 5T4 ELISPOT responses (antigen specific cells per $10^6$ PBMCs) in all evaluable patients were compared against the reported clinical responses. The mean ELISPOT responses were determined at selected time points over the entire monitoring time course and are tabulated in tables 7 a-c.

Tables 7a-7c: The tables illustrate the mean 5T4 specific ELISPOT responses (all 5T4 protein and peptide antigens) over the entire time course (7a), during chemotherapy (7b) or following completion of chemotherapy (7c). The mean ELISPOT responses are ranked from LOWEST to HIGHEST alongside the clinical response attributed to that patient at weeks 14 and X+8.

TABLE 7a

All 5T4 antigens, entire time course
Mean Post TroVax 5T4 TOTAL ELISPOT v
Tumour Resopnse

| Patient | ELISPOT | 14 wk | X + 8 wk |
|---|---|---|---|
| 113 | 0 | PD | PD |
| 117 | 0 | SD | 0 |
| 103 | 8.9 | PR | PR |
| 104 | 12 | SD | PD |
| 116 | 13.8 | PR | 0 |
| 114 | 42.9 | CR | 0 |
| 107 | 49.3 | PR | 0 |
| 108 | 159.2 | CR | CR |
| 105 | 311.7 | PR | SD |
| 101 | 315.2 | PR | PR |
| 102 | 431.2 | CR | CR |

TABLE 7b

All 5T4 antigens, during chemo
Mean Post TroVax 5T4 TOTAL ELISPOT
During Chemo v Tumour Resopnse

| Patient | ELISPOT | 14 wk | X + 8 wk |
|---|---|---|---|
| 103 | 0 | PR | PR |
| 113 | 0 | PD | PD |
| 117 | 0 | SD | 0 |
| 116 | 7.5 | PR | 0 |
| 104 | 28.4 | SD | PD |
| 114 | 49.4 | CR | 0 |
| 108 | 53 | CR | CR |
| 107 | 65 | PR | 0 |
| 101 | 83.3 | PR | PR |

TABLE 7b-continued

All 5T4 antigens, during chemo
Mean Post TroVax 5T4 TOTAL ELISPOT
During Chemo v Tumour Resopnse

| Patient | ELISPOT | 14 wk | X + 8 wk |
|---|---|---|---|
| 102 | 477 | CR | CR |
| 105 | 500.8 | PR | SD |

TABLE 7c

All 5T4 antigens, post chemo
Mean Post TroVax 5T4 TOTAL ELISPOT
Post Chemo v Tumour Resopnse

| Patient | ELISPOT | 14 wk | X + 8 wk |
|---|---|---|---|
| 113 | 0 | PD | PD |
| 117 | 0 | SD | 0 |
| 104 | 2.6 | SD | PD |
| 103 | 4.4 | PR | PR |
| 116 | 20 | PR | 0 |
| 107 | 42.3 | PR | 0 |
| 114 | 48.8 | CR | 0 |
| 105 | 247.7 | PR | SD |
| 101 | 534 | PR | PR |
| 108 | 557.1 | CR | CR |
| 102 | 653.3 | CR | CR |

A clustering of positive clinical responses with high mean ELISPOT responses is observed. In particular, the magnitude of responses to all 5T4 antigens over all time points and during the post chemotherapy period relates well to the reported tumour responses.

1.3.5 Integrated Analysis of Immunological v Clinical Responses

5T4 specific ELISPOT, proliferation and antibody responses were integrated and compared against the reported clinical responses. To achieve this, each evaluable patient was simply scored relative to the magnitude of the greatest immune response detected. For example, the patient with the highest mean 5T4 antibody titre across the selected monitoring period (i.e. all post TroVax time points, during chemo, post chemo) was given a score of 100%, all other patients were scored as a percentage of the greatest response. To integrate the assays, the scores per assay for each patient were simply added Such an analysis does take into consideration the magnitude of the patients' immune responses but gives equal "weight" to all assays. Tables 8a and b detail the hierarchy of integrated immunological responses (antibody+ELISPOT in table 8a and antibody+ELISPOT+Proliferation in table 8b) versus the reported clinical responses.

TABLE 8a

Integrated analysis of ELISPOT and Antibody assays over the entire immuno-monitoring time course v clinical responses

| | Tumour Response | | Combined Titre + ELISPOT |
|---|---|---|---|
| Patient | 14 wk | X + 8 wk | Score |
| 113 | PD | PD | 3.8 |
| 104 | SD | PD | 4.5 |
| 117 | SD | 0 | 7 |
| 116 | PR | 0 | 11.2 |
| 103 | PR | PR | 19.1 |
| 114 | CR | 0 | 20.7 |
| 101 | PR | PR | 73.1 |

TABLE 8a-continued

Integrated analysis of ELISPOT and Antibody assays over the entire immuno-monitoring time course v clinical responses

| | Tumour Response | | Combined Titre + ELISPOT |
|---|---|---|---|
| Patient | 14 wk | X + 8 wk | Score |
| 105 | PR | SD | 78.1 |
| 107 | PR | 0 | 94.1 |
| 108 | CR | CR | 136.9 |
| 102 | CR | CR | 139 |

TABLE 8b

Integrated analysis of ELISPOT, Antibody and Proliferation assays over the entire immuno-monitoring time course v clinical responses

| | Tumour Response | | Combined SI + Titre + ELISPOT |
|---|---|---|---|
| Patient | 14 wk | X + 8 wk | Score |
| 104 | SD | PD | 32.2 |
| 103 | PR | PR | 54.7 |
| 116 | PR | 0 | 98 |
| 113 | PD | PD | 103.8 |
| 117 | SD | 0 | 104.7 |
| 114 | CR | 0 | 120.5 |
| 105 | PR | SD | 130.4 |
| 101 | PR | PR | 139 |
| 108 | CR | CR | 177.9 |
| 107 | PR | 0 | 184.4 |
| 102 | CR | CR | 196.5 |

1.3.6 Comparisons of Immunological and Clinical Responses: Preliminary Conclusions This preliminary analysis indicates that some high magnitude 5T4 specific immune responses cluster with positive clinical responses. Such trends are discussed individually below:

A. ELISA

High 5T4 specific antibody titres are associated more frequently with complete and partial responses than with stable or progressive disease. This observation is consistent when responses are analysed over the entire monitoring time course, during and post chemotherapy. When analysing the post-chemo antibody responses, high titres cluster with CRs and PRs at the X+8 wk CT scan time point. The main exception to these trends is patient 101 who did not sero-convert but who mounted a strong ELISPOT response.

B. Proliferation

The magnitude of 5T4 specific proliferative responses does not appear to cluster with positive tumour responses (CRs and PRs). However, proliferative responses were greater following the completion of chemotherapy, with the greatest overall responses occurring at week X+10 i.e. too late to impact on tumour responses. These responses may reflect positively on survival.

C. ELISPOT

The magnitude of 5T4 specific ELISPOT responses appear to cluster with positive tumour responses. This trend is evident when the ELISPOT data are analysed across the entire time course, during chemotherapy and following the completion of chemotherapy.

D. Integrated Analysis: ELISA+ELISPOT

If data from both ELISA and ELISPOT are integrated and the magnitude of the combined responses tabulated alongside clinical responses, higher scores cluster more frequently with positive tumour responses. Patients classified as SD or PD at 14 wk or X+8 wk have the lowest combined scores.

E. Integrated Analysis: ELISA+ELISPOT+Proliferation

If data from both ELISA, ELISPOT and proliferation are integrated and the magnitude of the combined responses tabulated alongside clinical responses, again higher scores cluster more frequently with positive tumour responses.

2. TV2 IFL 2.1 Source Clinical and Patient Data

Nineteen patients were recruited into the TV2-FOLFOX trial of whom 12 became evaluable for assessment of immunological responses (Table 9).

TABLE 9

Clinical Data

| Patient ID | Alive/ Dead | Tumour Response | | Sum Target Lesions | | | Survival (weeks from wk 0) |
|---|---|---|---|---|---|---|---|
| | | Xwk | X + 14 wk | Screen | Xwk | X + 14 wk | |
| 001 | Dead | N/A | WD | 45 | WD | WD | 42 |
| 002 | Alive | CR | CR | 59 | 0 | 0 | 101 |
| 003 | Dead | PR | PD | 119 | 92 | N/A | 66 |
| 004 | Dead | WD | WD | 135 | WD | WD | 9 |
| 005 | Dead | PR | PD | 172 | 17 | 74 | 77 |
| 006 | Dead | N/A | N/A | 360 | WD | WD | 11 |
| 007 | Dead | SD | PD | 174 | 133 | 205 | 68 |
| 008 | Dead | WD | WD | 180 | WD | WD | 3 |
| 009 | Dead | SD | PD | 164 | 140 | 186 | 63 |
| 010 | Alive | PD | WD | 36 | 56 | WD | 82 |
| 011 | Dead | WD | WD | 38 | WD | WD | 0 |
| 012 | Dead | PR | PD | 306 | 138 | | 67 |
| 013 | Dead | PD | PD | 68 | 68 | WD | 58 |
| 014 | Alive | SD | | 114 | N/A | | 74 |
| 015 | Alive | PR | PD | 48 | 29 | 36 | 74 |
| 016 | Alive | PR | PD | 175 | 117 | 149 | 74 |
| 017 | Alive | PR | PD | 69 | Resolv | 30 | 71 |
| 018 | Alive | SD | PD | 284 | 225 | 278 | 66 |
| 019 | Alive | PD | PD | 279 | 254 | WD | 60 |

All 19 ITT patients are included in the table.
Evaluable patients are indicated by shading (survival data current to date).
Key: WD = Patient withdrawn therefore no result available; N/A = No data FIG. 3 shows TV2-IFL: Tumour dimensions throughout the clinical trial time course. The figure illustrates the sum of the target tumour lesions at 3 time points: prior to TroVax vaccination (screen) and at weeks X and X+14.

Of the 11 CT scan datasets available for the 12 evaluable patients, all showed a decrease in the sum of the target lesions at the Xwk time point. By X+14 wk, 5 patients (of 7 scans available) had target tumour burdens which remained below the level they were at screening.

2.2 Immunological Responses 2.2.1 Antibody Responses

Table 10 details the 5T4 specific antibody titres for each evaluable patient across the entire monitoring time course in the TV2-IFL trial.

Tables 10: 5T4 specific antibody responses. Results are expressed as a 5T4 specific antibody titre (the greatest serum dilution at which the test sample has a mean O.D. (490 nm)$\geq 2$ fold that of the negative control sample (normal human serum; [NHS]) at each sampling time point. Results tabulated in bold and $\geq 10$ represent positive antibody responses. Mean titres are reported for all patients at each time point and also at multiple time points pre-vaccination, during chemotherapy and post chemo. In addition, the fold increase in mean antibody titre compared to the previous time point is shown after each vaccination.

| Patient | 5T4 Specific Antibody Titre at Timepoints (weeks) Post Primary Immunisation | | | | | | | | | | | | | | |
|---|---|---|---|---|---|---|---|---|---|---|---|---|---|---|---|
| No | −2 | 0 | 2 | 4 | 6 | 11 | 13 | 17 | 19 | X + 2 | X + 4 | X + 6 | X + 8 | X + 10 | X + 14 |
| 002 | <10 | <10 | <10 | <10 | <10 | <10 | <10 | <10 | <10 | <10 | <10 | <10 | <10 | <10 | <10 |
| 003 | <10 | <10 | <10 | <10 | <10 | <10 | 20 | 20 | 40 | <10 | <10 | 10 | 20 | 20 | 40 |
| 005 | <10 | <10 | <10 | <10 | <10 | <10 | <10 | <10 | <10 | <10 | <10 | <10 | <10 | <10 | <10 |
| 007 | <10 | <10 | <10 | 160 | 80 | 10 | 10 | 10 | 10 | <10 | 20 | 40 | 20 | 10 | <10 |
| 009 | <10 | <10 | <10 | 10 | <10 | <10 | <10 | <10 | <10 | <10 | 10 | 10 | 160 | 80 | WD |
| 012 | <10 | <10 | 10 | 40 | <10 | <10 | <10 | <10 | <10 | <10 | <10 | <10 | 640 | 640 | <10 |
| 014 | <10 | <10 | <10 | 20 | <10 | <10 | <10 | <10 | <10 | <10 | <10 | <10 | 80 | 40 | 40 |
| 015 | <10 | <10 | <10 | <10 | <10 | <10 | <10 | <10 | <10 | <10 | <10 | <10 | 80 | 20 | <10 |
| 016 | <10 | <10 | <10 | 10 | <10 | <10 | 10 | <10 | <10 | <10 | 40 | 40 | 160 | 80 | 40 |
| 017 | <10 | <10 | <10 | <10 | <10 | <10 | <10 | <10 | <10 | <10 | 20 | <10 | 80 | 80 | 40 |
| 018 | <10 | <10 | <10 | <10 | <10 | <10 | <10 | <10 | 40 | <10 | 320 | 640 | 5120 | 1280 | 1280 |
| 019 | <10 | <10 | 10 | 20 | 10 | <10 | 10 | <10 | 10 | <10 | 10 | 10 | <10 | 20 | <10 |
| Mean Titre | <10 | <10 | 1.7 | 21.7 | 7.5 | 0.8 | 4.2 | 1.7 | 8.3 | <10 | 35 | 62.5 | 530 | 189.2 | 130.9 |
| Fold ↑ | | | | 13 | | | 5.3 | | 4.9 | ? | ? | | 8.5 | | |
| Mean Titre | | <10 | | | 7.4 | | | | | | | | 158.3 | | |

Over the entire post-TroVax immuno-monitoring time course, the mean 5T4 specific antibody titre was observed. The majority of patients sero-converted by week 4 (i.e. following 2 TroVax vaccinations). The mean antibody titres in the IFL trial were very low during chemotherapy (mean titre of 7.4), decreased following the completion of chemotherapy (between weeks 19 and X+2) and increased dramatically following completion of chemotherapy (mean titre of 158.3). Increases in the mean antibody titre were seen after each of the 6 vaccinations.

2.2.2 Proliferative Responses

Tables 11a-b detail antigen specific proliferative responses for each evaluable patient across the entire monitoring time course. The responses to 5T4 (11a) and MVA (11b) have been analysed Tables 11a and b: Summary proliferative responses of PBMCs recovered from patients following in vitro restimulation with 5T4 (a) and MVA (b). Results are expressed as a stimulation index (proliferation induced by medium alone÷proliferation induced by test antigen). A stimulation index ≧2 (indicated by bold text) is considered to be a positive response at that time point. Proliferative responses which are positive (S.I.≧2) and at least 2 fold greater than the pre-injection (−2 or 0 week) responses are indicated by red text.

TABLE 11a

TV2-IFL: Proliferative responses to 5T4

| Patient | Sampling Timepoints (weeks) | | | | | | | | | | | | | | |
|---|---|---|---|---|---|---|---|---|---|---|---|---|---|---|---|
| | −2 | 0 | 2 | 4 | 6 | 11 | 13 | 17 | 19 | X + 2 | X + 4 | X + 6 | X + 8 | X + 10 | X + 14 |
| 002 | 1.1 | 7.1 | 5.4 | 3.3 | 2.7 | 1 | 1 | 1.3 | 0.44 | 2.5 | 2.8 | 0.8 | 1.1 | 1.6 | 3.11 |
| 003 | 6.6 | 32.8 | 10.4 | 17.7 | 26.7 | 0.6 | 0.8 | 5.7 | 1.7 | 1.95 | 3.6 | 0.5 | 11.5 | 2.62 | 1.99 |
| 005 | 1 | 4.3 | 8.9 | 6.1 | 1 | 1.2 | 0.6 | 2.7 | 1.5 | 0.9 | 0.4 | 1.3 | 1.5 | 0.6 | 0.87 |
| 007 | 2.2 | 6.1 | 7.6 | 1.7 | 1.3 | 26.7 | 4.2 | 2.1 | 4.3 | 1.4 | 2.7 | 2.7 | 0.9 | 1.52 | 0.64 |
| 009 | 1.3 | 17.5 | 6.1 | 7.6 | 1.3 | 1.9 | 1.2 | 2.1 | 0.5 | 1.03 | 5.21 | 2.03 | 0.43 | 4.50 | WD |
| 012 | 2.2 | 2.2 | 2.2 | 3.1 | 3.9 | 1.5 | 1.7 | 2.1 | 1.55 | 19.83 | 22.47 | 39.70 | 2.24 | 14.13 | 19.64 |
| 014 | 4.2 | 1.7 | 17.7 | 2 | 2.6 | 2 | 1.2 | 4.2 | 2.88 | 16.58 | 4.99 | 5.65 | 6.04 | 1.31 | 10.13 |
| 015 | 2.3 | 2.8 | 7 | 5.6 | 4.5 | 0.5 | 0.76 | 1.81 | 0.73 | 17.08 | 3.96 | 5.02 | 1.76 | 2.10 | 3.94 |
| 016 | 1.9 | 1.3 | 7.6 | 8.6 | 0.9 | 2.7 | 4.6 | 1.9 | 0.92 | 28.86 | 3.35 | 8.41 | 8.57 | 3.12 | 7.73 |
| 017 | 3.5 | 8 | 2.1 | 0.6 | 0.9 | 2.1 | 3.5 | 1.27 | 0.82 | 6.38 | 11.30 | 2.45 | 4.91 | 4.71 | 1.27 |
| 018 | 0.6 | 3.3 | 1.3 | 2.9 | 1.3 | 0.97 | 0.82 | 1.14 | 1.93 | 12.65 | 9.65 | 5.61 | 5.72 | 2.80 | 1.60 |
| 019 | 0.6 | 2.3 | 1.58 | 1.31 | 2.72 | 25.08 | 10.83 | 18.67 | N/A | 0.74 | 4.01 | 12.83 | 1.17 | 3.00 | 2.59 |
| Mean SI | 2.3 | 7.5 | 6.5 | 5 | 4.1 | 5.5 | 2.6 | 3.7 | 1.6 | 9.2 | 6.2 | 7.3 | 3.8 | 3.5 | 4.9 |
| Fold ↑ | | | 0.9 | 0.8 | | | 0.5 | | 0.4 | | 5.8 | 0.7 | | 0.5 | |
| Mean SI | | 4.9 | | | | | 3.8 | | | | | | 5.8 | | |

TABLE 11b

TV2-IFL: Proliferative responses to MVA

| Patient | Sampling Timepoints (weeks) | | | | | | | | | | | | | | |
|---|---|---|---|---|---|---|---|---|---|---|---|---|---|---|---|
| | −2 | 0 | 2 | 4 | 6 | 11 | 13 | 17 | 19 | X + 2 | X + 4 | X + 6 | X + 8 | X + 10 | X + 14 |
| 002 | 0.4 | 1.3 | 3.2 | 13.7 | 4.9 | 1.2 | 1.7 | 1.6 | 1.7 | 0.4 | 0.3 | 5.3 | 1.1 | 1 | 10.41 |
| 003 | 1.1 | 1 | 10.6 | 14.8 | 12 | 1.8 | 3.1 | 0.7 | 0.4 | 2.2 | 29.1 | 20.4 | 35.3 | 52.67 | 8.60 |

TABLE 11b-continued

TV2-IFL: Proliferative responses to MVA

| | Sampling Timepoints (weeks) | | | | | | | | | | | | | | |
|---|---|---|---|---|---|---|---|---|---|---|---|---|---|---|---|
| Patient | −2 | 0 | 2 | 4 | 6 | 11 | 13 | 17 | 19 | X + 2 | X + 4 | X + 6 | X + 8 | X + 10 | X + 14 |
| 005 | 2.1 | 4.5 | 27 | 16.2 | 2 | 8.7 | 2.5 | 1.2 | 0.4 | 0.2 | 0.6 | 1.5 | 2.3 | 4.8 | 12.50 |
| 007 | 1 | 1.7 | 70 | 72.6 | 6.3 | 5.8 | 6.5 | 1 | 0.9 | 1.9 | 8.6 | 9.2 | 42.72 | 54.25 | 38.90 |
| 009 | 5.3 | 21 | 25.5 | 23 | 17.8 | 1.1 | 0.7 | 0.7 | 2.6 | 44.60 | 100.56 | 21.50 | 83.07 | 20.31 | WD |
| 012 | 0.8 | 0.6 | 1.97 | 6.1 | 5.4 | 0.7 | 2.8 | 1.5 | 1.63 | 9.25 | 43.60 | 5.28 | 1.22 | 45.61 | 0.93 |
| 014 | 1.1 | 0.7 | 11 | 0.5 | 0.8 | 0.2 | 1 | 0.89 | 15.92 | 16.49 | 32.54 | 24.99 | 69.54 | 2.01 | 7.97 |
| 015 | 0.8 | 1 | 1 | 1.7 | 2.3 | 8.8 | 4.08 | 47.44 | 69.59 | 14.87 | 9.44 | 15.03 | 7.13 | 6.23 | 3.56 |
| 016 | 1.3 | 1 | 2.5 | 0.6 | 0.3 | 1.4 | 6.3 | 2.53 | 15.19 | 21.58 | 6.58 | 12.96 | 46.31 | 4.45 | 11.84 |
| 017 | 0.8 | 0.8 | 1.2 | 0.1 | 0.5 | 0.88 | 0.30 | 4.16 | 4.32 | 6.13 | 4.77 | 1.51 | 41.83 | 2.48 | 1.06 |
| 018 | 0.6 | 2.1 | 17.7 | 38.2 | 14 | 7.76 | 3.85 | 15.01 | 3.33 | 3.15 | 45.89 | 14.03 | 25.55 | 4.78 | 11.18 |
| 019 | 0.2 | 1 | 1.49 | 6.83 | 53.15 | 21.13 | 12.22 | 12.73 | N/A | 0.93 | 4.34 | 25.10 | 1.88 | 7.97 | 4.72 |
| Mean SI | 1.3 | 3.1 | 14.4 | 16.2 | 9.9 | 5 | 3.8 | 7.5 | 10.5 | 10.1 | 23.9 | 13.1 | 29.8 | 17.2 | 10.2 |
| Fold ↑ | | | 4.6 | 1.1 | | | 0.8 | | 1.4 | 1 | 2.4 | | 2.3 | | |
| Mean SI | | 0.95 | | | | 4 | | | | | | | 11.9 | | |

The mean proliferative responses to 5T4 and MVA show differences in both the magnitude and longevity of the response. Each antigen will be addressed in turn:

A. 5T4

Overall, the mean proliferative response to 5T4 showed no increase following TroVax vaccination compared to pre-injection (both have a mean SI of 4.9). Therefore, at the population level and across ALL time points, IFL patients show no increase in the mean proliferative response to 5T4 post-TroVax vaccination. However, at specific time points responses are elevated in individual patients. Responses were elevated following completion of chemotherapy (S.I. of 5.8 post-chemo versus 3.8 during chemo) and this differential was most marked between weeks 19 and X+2 i.e. between the last time point at which most patients were still receiving chemotherapy and the first time point following completion of chemotherapy. This observation was unexpected because patients did not receive a vaccination within this period, their last vaccination took place at week 17. IFL patients showed a 6 fold increase in mean proliferative responses between weeks 19 and X+2 (SI of 1.6 v 9.2 respectively) which was the greatest fold increase observed, being greater than following any of the 6 vaccinations.

B. MVA

The mean proliferative response to MVA was 6 fold greater following TroVax vaccination compared to pre-injection (mean S.I. of 13.2 compared to 2.2 respectively). The MVA specific proliferative response was greater following completion of chemotherapy than during chemotherapy which was similar to the pattern observed for 5T4. However, unlike 5T4, there was no difference in the proliferative response detected at weeks 19 and X+2 (mean S.I.s of 10.5 versus 10.1 respectively).

2.3 Comparisons of Immunological and Clinical Responses
2.3.1 Summary Immunological Responses Across All Assays

TABLE 12

Summary immune responses seen in all evaluable patients

| Patient ID | Tumour Response | | Summary Immunological Responses |
|---|---|---|---|
| | Xwk | X + 14 wk | |
| 002 | CR | CR | ELISA: No 5T4 Ab response detected |
| | | | PROLIF: No response cf screen |
| | | | ELISPOT: Weak response single time point to peptide #77 |
| 003 | PR | PD | ELISA: Weak Ab response during and post-chemotherapy |
| | | | PROLIF: No response cf screen |
| | | | ELISPOT: Very weak to 5T4 and pool #8 at X + 8 wk only |
| 005 | PR | PD | ELISA: No 5T4 Ab response detected |
| | | | PROLIF: Weak and transient response cf screen |
| | | | ELISPOT: Strong responses pre and post Cx to multiple Peps |
| 007 | SD | PD | ELISA: Weak Ab response pre Cx, moderate post Cx |
| | | | PROLIF: Weak but transient response cf screen |
| | | | ELISPOT: Very strong to 5T4 protein only. Post Cx |
| 009 | SD | PD | ELISA: Weak Ab response pre Cx, moderate post Cx |
| | | | PROLIF: No response cf screen |
| | | | ELISPOT: Very strong to Class I peps pre and post Cx |
| 012 | PR | PD | ELISA: Weak Ab response pre Cx, strong post Cx |
| | | | PROLIF: Strong response but only post-chemo |
| | | | ELISPOT: Very strong to multiple peps pre and post Cx |
| 014 | SD | | ELISA: Weak Ab response pre Cx, moderate post Cx |
| | | | PROLIF: Strong response pre and post-chemo |
| | | | ELISPOT: No responses |
| 015 | PR | PD | ELISA: No Ab response pre or during Cx, moderate post Cx |
| | | | PROLIF: Strong but transient response pre and post-chemo |
| | | | ELISPOT: Very Weak to one class II peptide at one timepoint |

TABLE 12-continued

Summary immune responses seen in all evaluable patients

| Patient ID | Tumour Response Xwk | X + 14 wk | Summary Immunological Responses |
|---|---|---|---|
| 16 | PR | PD | ELISA: Weak Ab response pre Cx, moderate post Cx<br>PROLIF: Strong response pre, during but primarily post-Cx<br>ELISPOT: Weak response to class II peptide #41 |
| 017 | PR | PD | ELISA: No Ab response pre or during Cx, moderate post Cx<br>PROLIF: No response cf screen<br>ELISPOT: Very weak to peptide pool #13 @ 1 timepoint |
| 018 | SD | PD | ELISA: No Ab response pre Cx, very strong post Cx<br>PROLIF: Strong transient response post-Cx<br>ELISPOT: Very strong and sustained class I pools 1, 5 and 20 |
| 019 | PD | PD | ELISA: Very weak Ab response throughout<br>PROLIF: Strong response during and post-Cx<br>ELISPOT: Very weak single timepoint |

2.3.2 Analysis of Antibody Responses Versus Clinical Responses

The MEAN 5T4 antibody titres in all evaluable patients were compared against the reported clinical responses (some CT scans are outstanding). Mean 5T4 antibody titres were determined over 3 time periods: (i) Over all post TroVax time points i.e. from week 2 to week X+10 (or the last data point available), (ii) Over all post-TroVax time points occurring during the period of chemotherapy (weeks 4-19) and (iii) over all post-TroVax time points occurring following completion of chemotherapy (weeks X+2 to X+14). Tables 13a-13c rank the mean antibody titres against the respective clinical responses reported in that patient.

Tables 13a-13c: The tables illustrate the mean 5T4 antibody titres over the entire monitoring period (weeks 2–X+14; Table 13a), during chemotherapy (weeks 4-19; Table 13b) and following completion of chemotherapy (weeks X to X+14; Table 13c). The mean titres are ranked from LOWEST to HIGHEST alongside the clinical response attributed to that patient at weeks X and X+14.

TABLE 13a

Entire Time Course
Mean Post TroVax 5T4 Titres v Tumour Response

| Patient | Titre | Xwk | X + 14 wk |
|---|---|---|---|
| 2 | 0.0 | CR | CR |
| 5 | 0.0 | PR | PD |
| 15 | 7.7 | PR | PD |
| 19 | 7.7 | PD | PD |
| 3 | 13.1 | PR | PD |
| 14 | 13.8 | SD | |
| 17 | 16.9 | PR | PD |
| 9 | 22.5 | SD | PD |
| 7 | 27.7 | SD | PD |
| 16 | 29.2 | PR | PD |
| 12 | 102.3 | PR | PD |
| 18 | 667.7 | SD | PD |

TABLE 13b

During Chemotherapy
Mean Post TroVax 5T4 Titres During Chemo v Tumour Response

| Patient | Titre | X wk | X + 14 wk |
|---|---|---|---|
| 2 | 0.0 | CR | CR |
| 5 | 0.0 | PR | PD |
| 15 | 0.0 | PR | PD |
| 17 | 0.0 | PR | PD |
| 9 | 1.7 | SD | PD |
| 14 | 3.3 | SD | |
| 16 | 3.3 | PR | PD |
| 12 | 6.7 | PR | PD |
| 18 | 6.7 | SD | PD |
| 19 | 8.3 | PD | PD |
| 3 | 13.3 | PR | PD |
| 7 | 45.0 | SD | PD |

TABLE 13c

Post Chemotherapy
Mean Post TroVax 5T4 Titres Post Chemo v Tumour Response

| Patient | Titre | X wk | X + 14 wk |
|---|---|---|---|
| 2 | 0.0 | CR | CR |
| 5 | 0.0 | PR | PD |
| 19 | 6.7 | PD | PD |
| 3 | 15.0 | PR | PD |
| 7 | 15.0 | SD | PD |
| 15 | 16.7 | PR | PD |
| 14 | 26.7 | SD | |
| 17 | 36.7 | PR | PD |
| 9 | 52.0 | SD | PD |
| 16 | 60.0 | PR | PD |
| 12 | 213.3 | PR | PD |
| 18 | 1440.0 | SD | PD |

Antibody responses in this patient group were very low during chemotherapy compared to post-chemotherapy (mean titres of 7 compared to 158). Furthermore, the greatest mean antibody titre occurred at week X+8. A potent antibody response at this time may not impact on tumour responses detected at week X+14, but may have a positive effect on patient survival.

2.3.3 Analysis of Proliferative Responses Versus Clinical Responses

The MEAN 5T4 proliferative responses (SIs) in all evaluable patients were compared against the reported clinical responses (some CT scans are outstanding). The mean proliferative responses were determined over 3 time periods (the entire monitoring timecourse, during chemotherapy and following completion of chemotherapy) and are tabulated in tables 14 a-c.

Tables 14a-14c: The tables illustrate the mean 5T4 proliferative responses over 3 different time periods: Table 14a the entire monitoring period (weeks 2–X+14), Table 14b during chemotherapy (weeks 4-19) and Table 14c following completion of chemotherapy (weeks X to X+14). The mean proliferative responses are ranked from LOWEST to HIGHEST alongside the clinical response attributed to that patient at weeks X and X+14.

TABLE 14a

Entire Time course
Mean Post TroVax 5T4 SI v Tumour Resopnse

| Pateient | SI | X wk | X + 14 wk |
|---|---|---|---|
| 2 | 2.08 | CR | CR |
| 5 | 2.12 | PR | PD |
| 9 | 2.83 | SD | PD |
| 17 | 3.25 | PR | PD |
| 18 | 3.72 | SD | PD |
| 15 | 4.21 | PR | PD |
| 7 | 4.44 | SD | PD |
| 14 | 5.94 | SD | |
| 3 | 6.60 | PR | PD |
| 16 | 6.71 | PR | PD |
| 19 | 7.04 | PD | PD |
| 12 | 10.31 | PR | PD |

TABLE 14b

During Chemotherapy
Mean Post TroVax 5T4 SI During Chemo v Tumour Resopnse

| Pateient | SI | X wk | X + 14 wk |
|---|---|---|---|
| 18 | 1.51 | SD | PD |
| 17 | 1.53 | PR | PD |
| 2 | 1.62 | CR | CR |
| 5 | 2.18 | PR | PD |
| 12 | 2.31 | PR | PD |
| 15 | 2.32 | PR | PD |
| 9 | 2.43 | SD | PD |
| 14 | 2.48 | SD | |
| 16 | 3.27 | PR | PD |
| 7 | 6.72 | SD | PD |
| 3 | 8.87 | PR | PD |
| 19 | 11.72 | PD | PD |

TABLE 14c

Post Chemotherapy
Mean Post TroVax 5T4 SI Post Chemo v Tumour Resopnse

| Pateient | SI | X wk | X + 14 wk |
|---|---|---|---|
| 5 | 0.93 | PR | PD |
| 7 | 1.64 | SD | PD |
| 2 | 1.99 | CR | CR |
| 9 | 2.64 | SD | PD |
| 3 | 3.69 | PR | PD |
| 19 | 4.06 | PD | PD |
| 17 | 5.17 | PR | PD |
| 15 | 5.64 | PR | PD |
| 18 | 6.34 | SD | PD |
| 14 | 7.45 | SD | |

TABLE 14c-continued

Post Chemotherapy
Mean Post TroVax 5T4 SI Post Chemo v Tumour Resopnse

| Pateient | SI | X wk | X + 14 wk |
|---|---|---|---|
| 16 | 10.01 | PR | PD |
| 12 | 19.67 | PR | PD |

2.3.4 Analysis of ELISPOT Responses Versus Clinical Responses

The MEAN 5T4 ELISPOT responses (antigen specific cells per 106 PBMCs) in all evaluable patients were compared against the reported clinical responses (some CT scans are outstanding). The mean ELISPOT responses were determined at selected time points over the entire monitoring time course and are tabulated in tables 15 a-c.

Tables 15a-15c: The tables illustrate the mean 5T4 ELISPOT responses over the entire time course (15a), during chemotherapy (15b) or post-chemotherapy (15c). The mean ELISPOT responses are ranked from LOWEST to HIGHEST alongside the clinical response attributed to that patient at weeks X and X+14.

TABLE 15a

All 5T4 antigens, entire time course
Mean Post TroVax 5T4 TOTAL ELISPOT v Tumour Response

| Patient | ELISPOT | X wk | X + 14 wk |
|---|---|---|---|
| 2 | 47.5 | CR | CR |
| 3 | 6.7 | PR | PD |
| 5 | 91.6 | PR | PD |
| 7 | 33.5 | SD | PD |
| 9 | 371.8 | SD | PD |
| 12 | 99.2 | PR | PD |
| 14 | 0 | SD | |
| 15 | 7.2 | PR | PD |
| 16 | 33.5 | PR | PD |
| 17 | 5.7 | PR | PD |
| 18 | 165.6 | SD | PD |
| 19 | 4.1 | PD | PD |

TABLE 15b

All 5T4 antigens, during chemotherapy
Mean Post TroVax DURING Chemo 5T4 ELISPOT v Tumour Response

| Patient | ELISPOT | X wk | X + 14 wk |
|---|---|---|---|
| 3 | 0 | PR | PD |
| 7 | 0 | SD | PD |
| 16 | 0 | PR | PD |
| 17 | 0 | PR | PD |
| 14 | 0 | SD | |
| 19 | 13.6 | PD | PD |
| 15 | 14.4 | PR | PD |
| 12 | 26.3 | PR | PD |
| 18 | 79.7 | SD | PD |
| 5 | 91.7 | PR | PD |
| 2 | 113.25 | CR | CR |
| 9 | 264.4 | SD | PD |

TABLE 15c

All 5T4 antigens, post chemotherapy
Mean Post TroVax POST Chemo 5T4
ELISPOT v Tumour Resopnse

| Patient | ELISPOT | X wk | X + 14 wk |
|---|---|---|---|
| 15 | 0 | PR | PD |
| 19 | 0 | PD | PD |
| 14 | 0 | SD | |
| 3 | 8.9 | PR | PD |
| 17 | 13.3 | PR | PD |
| 2 | 26.5 | CR | CR |
| 7 | 50.3 | SD | PD |
| 16 | 55.8 | PR | PD |
| 5 | 91.6 | PR | PD |
| 12 | 189.3 | PR | PD |
| 18 | 236.1 | SD | PD |
| 9 | 425.4 | SD | PD |

Analysis of 5T4 ELISPOT responses showed a better clustering of high 5T4 responses with beneficial clinical responses than did the same calculation using proliferation as a variable.

2.3.5 Integrated Analysis of Immunological v Clinical Responses

5T4 specific ELISPOT, proliferation and antibody responses were integrated and compared against the reported clinical responses. To achieve this, each evaluable patient was simply scored relative to the magnitude of the greatest immune response detected. For example, the patient with the highest mean 5T4 antibody titre across the selected monitoring period (i.e. all post TroVax time points, during chemo, post chemo) was given a score of 100%, all other patients were scored as a percentage of the greatest response. To integrate the assays, the scores per assay for each patient were simply added Such an analysis does take into consideration the magnitude of the patients' immune responses but gives equal "weight" to all assays. Tables 16 a and b detail the hierarchy of integrated immunological responses (antibody+ELISPOT in table 16a and antibody+ELISPOT+Proliferation in table 16b) versus the reported clinical responses.

TABLE 16a

Integrated analysis of ELISPOT + Antibody assays over the entire immuno-monitoring time course v clinical responses

| | Tumour Response | | Combined Titre + ELISPOT |
|---|---|---|---|
| Patient | X wk | X + 14 wk | Score |
| 14 | SD | | 2 |
| 19 | PD | PD | 2 |
| 15 | PR | PD | 3 |
| 3 | PR | PD | 4 |
| 17 | PR | PD | 5 |
| 2 | CR | CR | 13 |
| 7 | SD | PD | 13 |
| 16 | PR | PD | 13 |
| 5 | PR | PD | 25 |
| 12 | PR | PD | 42 |
| 9 | SD | PD | 103 |
| 18 | SD | PD | 145 |

TABLE 16b

Integrated analysis of ELISPOT, Antibody and Proliferation assays over the entire immuno-monitoring time course v clinical responses

| | Tumour Response | | Combined SI + Titre + ELISPOT |
|---|---|---|---|
| Patient | X wk | X + 14 wk | Score |
| 2 | CR | CR | 33 |
| 17 | PR | PD | 37 |
| 15 | PR | PD | 44 |
| 5 | PR | PD | 46 |
| 7 | SD | PD | 56 |
| 14 | SD | | 60 |
| 3 | PR | PD | 68 |
| 19 | PD | PD | 70 |
| 16 | PR | PD | 78 |
| 9 | SD | PD | 130 |
| 12 | PR | PD | 142 |
| 18 | SD | PD | 181 |

Strong immune responses in the IFL trial occurred primarily following completion of chemotherapy. Therefore it is unlikely that the immune response would have a beneficial impact on the tumour by the X week CT scan and possibly not even by X+14.

3. A Comparison of Immune Responses Occurring in the FOLFOX and IFL Trials 3.1 Antibody Responses Over the entire immuno-monitoring time course, the mean 5T4 specific antibody titres (to date) were similar for both trials, 76 for TV2-IFL and 100 for TV2-FOLFOX (Table 17). However, the kinetics of the antibody responses were different for each trial. In the IFL trial, antibody responses were very low during chemotherapy (a mean titre of 7 between weeks 4 to 19) but increased dramatically (>20 fold) following completion of chemotherapy (a mean titre of 158 between weeks X+2 and X+14). In contrast, mean antibody titres in the FOLFOX trial were high during chemotherapy (mean titre of 103) and increased moderately following completion of chemotherapy (mean titre of 115). In both trials, the mean antibody titres decreased between weeks 19 and X+2. Increases in antibody titre were seen after all 6 vaccinations in both trials.

TABLE 17

A comparison of 5T4 specific antibody responses between TV2 IFL and FOLFOX trials.

| | Mean Response | |
|---|---|---|
| Measurement of 5T4 Specific Antibody Responses | FOLFOX (n = 11) | IFL (n = 12) |
| Mean 5T4 Ab response (pre TroVax) | <10 | <10 |
| Mean 5T4 Ab response (all time points) | 100 | 76.1 |
| Mean 5T4 Ab response (during chemo) | 102.6 | 7.4 |
| Mean 5T4 Ab response (post chemo) | 115.1 | 158.3 |

3.1.1 Statistical Analysis of 5T4 Specific Antibody Responses Detected in TV2 IFL and FOLFOX Trials A statistical analysis of the data was undertaken on a "per trial" basis using Wilcoxon. Results are as follows:
(a) Response during chemotherapy (weeks 2 to 19)
IFL: mean score (titre)=0.44 (<10)
FOLFOX: mean score (titre)=1.73 (17)
Difference between groups P=0.011 (P<2%)
Conclusion: There is a significant difference in the antibody titres detected in the IFL and FOLFOX groups during the period in which patients receive chemotherapy.

(b) Response after chemotherapy (weeks X+2 to X+10)
IFL: mean score (titre)=1.85 (18)
FOLFOX: mean score (titre)=2.29 (24)
Difference between groups P=0.53 (NS)

Conclusion: There is no significant difference in the antibody titres detected in the IFL and FOLFOX groups during the period following completion of chemotherapy.

(c) Change from during to after chemotherapy (weeks 2-19 v X+2–X+10)
IFL: mean score (titre) during=0.44 (<10) after=1.85 (18) change=1.41 (×2.7) P=0.020 (P<2%)
FOLFOX: mean score (titre) during=1.73 (17) after=2.29 (24) change=0.56 (×1.5) P=0.16 (NS)

Conclusion: There is a significant difference in the antibody titres detected in the IFL group during chemotherapy compared to post-chemotherapy. In contrast, there is no significant difference in the FOLFOX group.

(d) Change from week 19 to week X+2
IFL:
mean score (titre) week 19=0.67 (<10)
mean score (titre) week X+2=0.00 (<10)
change=−0.67 (×0.62) P=0.13 (NS)
FOLFOX:
mean score (titre) week 19=2.27 (24)
mean score (titre) week X+2=0.36 (<10)
change=−1.91 (×0.27) P=0.016 (<2%) difference between groups P=0.10 (NS)

Conclusion: Between weeks 19 and X+2 there is no significant difference in the antibody titres detected in the IFL group but a significant decrease in the titres in the FOLFOX group.

3.2 Proliferative Responses

5T4 specific proliferative responses were of greater magnitude in the FOLFOX compared to the IFL trial (Table 18). In both trials, proliferative responses were of greater magnitude following completion of chemotherapy. The differential was most profound between weeks 19 and X+2 as illustrated in FIGS. 4 a-b. However, such differences were not as apparent when the responses to MVA or TT were analysed (FIGS. 4c-4f).

TABLE 18

A comparison of 5T4 specific proliferative responses between TV2 IFL and FOLFOX trials.

| Measurement of 5T4 Specific Immune Response | Mean Response | |
|---|---|---|
| | FOLFOX (n = 11) | IFL (n = 12) |
| Mean 5T4 proliferative response (pre TroVax) | 3.6 | 4.9 |
| Mean 5T4 proliferative response (all time points) | 6.8 | 4.9 |
| Mean 5T4 proliferative response (during chemo) | 4.3 | 3.8 |
| Mean 5T4 proliferative response (post chemo) | 10.5 | 5.8 |

FIG. 4a shows 5T4 Responses in TV2-IFL, FIG. 4b shows 5T4 Responses in TV2-FOLFOX, FIG. 4c shows MVA Responses in TV2-IFL, FIG. 4d shows MVA Responses in TV2-FOLFOX, FIG. 4e shows TT Responses in TV2-IFL and FIG. 4f shows TT Responses in TV2-FOLFOX 3.2.1 Statistical Analysis of 5T4 Specific Proliferative Responses Detected in TV2 μL and FOLFOX Trials A statistical analysis (Wilcoxon) was undertaken to assess the significance of antigen-specific immune responses detected in TV2 FOLFOX and IFL trials.

(a) change in proliferative responses from baseline to post-vaccination (weeks −2 and 0 versus weeks 2 to week X+14 (IFL) or week X+10 (FOLFOX))
5T4
IFL: mean log (S.I.) baseline=1.05 (2.9) post-v 1.02 (2.8) change=−0.03 (×0.97) P=0.96 (NS)
FOLFOX: mean log (S.I.) baseline=0.69 (2.0) post-v=1.25 (3.5) change=0.56 (×1.8) P=0.10 (NS)
MVA
IFL: mean log (S.I.) baseline=0.17 (1.2) post-v=1.62 (5.1) change=1.45 (×4.3) P=0.002 (P<0.5%)
FOLFOX: mean log (S.I.) baseline=0.18 (1.2) post-v=2.37 (10) change=2.19 (×8.9) P=0.002 (P<0.5%)
TT
IFL: mean log (S.I.) baseline=0.90 (2.5) post-v=1.06 (2.9) change=0.17 (×1.2) P=0.52 (NS)
FOLFOX: mean log (S.I.) baseline=1.42 (4.1) post-v=1.50 (4.5) change=0.08 (×1.1) P=1.00 (NS)

Conclusion: Proliferative responses to 5T4 and TT show no significant change from baseline to post-TroVax vaccination. However, responses to MVA show a significant increase.

(b) change in proliferative responses from baseline to during chemotherapy
(weeks −2 and 0 versus weeks 4 to week 19)
5T4
IFL: mean log (S.I.) baseline=1.05 (2.9) during=0.76 (2.2) change=−0.29 (×0.75) P=0.11 (NS)
FOLFOX: mean log (S.I.) baseline=0.69 (2.0) during=0.94 (2.6) change=0.25 (×1.3) P=0.64 (NS)
MVA
IFL: mean log (S.I.) baseline=0.17 (1.2) during=1.17 (3.2) change=1.00 (×2.7) P=0.03 (P<5%)
FOLFOX: mean log (S.I.) baseline=0.18 (1.2) during=1.99 (7.3) change=1.81 (×6.1) P=0.003 (P<0.5%)
TT
IFL: mean log (S.I.) baseline=0.90 (2.5) during=0.98 (2.7) change=0.09 (×1.1) P=0.79 (NS)
FOLFOX: mean log (S.I.) baseline=1.42 (4.1) during=1.47 (4.3) change=0.04 (×1.04) P=0.89 (NS)

Conclusion: Proliferative responses to 5T4 and TT show no significant change from baseline to post-TroVax vaccination time points occurring during chemotherapy. However, responses to MVA show a significant increase.

(c) change in proliferative responses from baseline to after chemotherapy (weeks −2 and 0 versus weeks 2 to week X+14 (IFL) or week X+10 (FOLFOX))
5T4
IFL: mean log (S.I.) baseline=1.05 (2.9) after=1.18 (3.3) change=0.13 (×1.1) P=0.79 (NS)
FOLFOX: mean log (S.I.) baseline=0.69 (2.0) after=1.82 (6.2) change=1.13 (×3.1) P=0.04 (P<5%)
MVA
IFL: mean log (S.I.) baseline=0.17 (1.2) after=2.05 (7.8) change=1.88 (×6.6) P=0.001 (P<0.2%)
FOLFOX: mean log (S.I.) baseline=0.18 (1.2) after=2.84 (17) change=2.66 (×14) P=0.003 (P<0.5%)
TT
IFL: mean log (S.I.) baseline=0.90 (2.5) after=1.16 (3.2) change=0.27 (×1.3) P=0.27 (NS)
FOLFOX: mean log (S.I.) baseline=1.42 (4.1) after=1.58 (4.9) change=0.16 (×1.2) P=0.90 (NS)

Conclusion: Proliferative responses to 5T4 (IFL only) and TT show no significant change from baseline to post-TroVax vaccination time points occurring following completion of chemotherapy. However, responses to MVA and 5T4 (FOLFOX only) show a significant increase.

(d) change in proliferative responses between weeks 19 and X+2
5T4
IFL: mean log (S.I.) week 19=0.33 (1.4) week X+2=1.49 (4.4) change=1.16 (×3.2) P=0.04 (P<5%)

FOLFOX:mean log (S.I.) week 19=0.75 (2.1) week X+2=1.64 (5.2) change=0.89 (×2.4) P=0.04 (P<5%)
MVA
IFL: mean log (S.I.) week 19=1.24 (3.5) week X+2=1.37 (3.9) change=0.13 (×1.1) P=0.68(NS)
FOLFOX:mean log (S.I.) week 19=2.02 (7.5) week X+2=2.33 (10) change=0.31 (×1.4) P=0.64 (NS)
TT
IFL: mean log (S.I.) week 19=1.42 (4.1) week X+2=1.13 (3.1) change=−0.29 (×0.75) P=0.34 (NS)
FOLFOX:mean log (S.I.) week 19=1.48 (4.4) week X+2=1.47 (4.3) change=−0.02 (×0.98) P=0.90 (NS)

Conclusion: Proliferative responses to MVA and TT show no significant change from week 19 to X+2. However, responses to 5T4 show a significant increase.

Summary

Antibody responses in the IFL group are suppressed by the chemo regimen compared to the FOLFOX group. However, in both groups a boosting effect can be seen in many patients following the $5^{th}$ and $6^{th}$ vaccinations—this was rarely seen in the previous TV1 trial. Indeed, mean 5T4 antibody titres were boosted following each of the 6 vaccinations in both IFL and FOLFOX trials.

At the cellular level, mean proliferative responses to both 5T4 and TT showed no significant increase post-TroVax vaccination compared to baseline levels. However, mean proliferative responses detected following completion of chemotherapy were significantly elevated compared to baseline in the FOLFOX trial. The increase in proliferative responses to 5T4 between weeks 19 and X+2 is intriguing. Responses to 5T4, but not MVA or TT, were significantly enhanced between these 2 time points despite the fact that no vaccinations occurred within this period (approximately 8 weeks). An analysis of the levels of regulatory T cells in the periphery may provide further insight into this observation.

4. T regulatory Cells

A subset of T cells was originally referred to as suppressor T cells in the 1970s due to their ability to induce tolerance and are now described as T regulatory cells (Gershon and Kondo, 1970. Immunology 18:723-737; Gershon 1975. Transplant Rev. 26:170-185; Taams and Akbar, 2005. Curr. Top. Microbiol. Immunol. 293:115-131). T regulatory (Tr) cells play an essential role in the induction and maintenance of tolerance to both foreign and self antigens. Different types of regulatory/suppressor cells have been described, including $CD4^+CD25^+$ T cells, TGF-β producing TH3 cells, IL-10 producing Tr1 cells and $CD8^+CD28^-$ T cells (for reviews see Levings and Roncarlo, 2005. CTMI. 292:303-326; Huehn, Siegmund and Hamann, 2005. CITR 293: 89-114; Faria and Weiner, 2005 Immunol. Rev. 206:232-259; Weiner, 2001 Immunol. Rev. 182:207-214; Weiner et al, 2001. Microbes Infect. 3: 947-954; Roncarolo et al, 2001 Immunol. Rev. 182: 68-79

4.1. $CD4^+CD25^+$ Tregs: Introduction

These regulatory T cells can be detected in human peripheral blood and are able to suppress bystander T cells in an antigen non-specific and contact-dependent manner. These Tregs are characterised by expression of high constitutive levels of the α-chain (CD25) of the IL-2 receptor and are often referred to as $CD4^{+CD}25^{hi+}$ Tregs. They also express high levels of the intracellular transcription factor FoxP3 and other cell receptors including CTLA-4, GITR (Glucocorticoid-induced TGFR superfamily member 18), CD45RO, CD45RB, ICOS and neuropilin 1. In contrast to murine $CD4^+CD25^+$ Tregs, human counterparts do not express high levels of the integrin CD103. Since all of the markers that can be used to identify $CD4^+ CD25^+$ cells can be expressed by other subsets of T cells, albeit in various levels and combinations, there is no single marker that defines a $CD4^+CD25^+$ Treg cell.

The precise molecular mechanism(s) by which $CD4^+CD25^+$ Tregs exert their suppressive function remains undefined, but requires cell contact and is not dependent on the Tregs secreting cytokines themselves (Takahashi et al, 1998 Int. Immunol. 10:1969-1980; Thorton and Shevach 1998. J. Exp. Med. 188:287-296). $CD4^+CD25^+$ Tregs can exert their suppressive effects on T cells, B cells, dendritic cells, NK cells (Shimuzu et al, 1999. J. Immunol. 163: 5211-5218), neutrophils, monocytes and macrophages (Maloy et al, 2003. J. Exp. Med. 197: 111-119; Taams et al, 2005. Hum. Immunol. 66: 222-230).

$CD4^+CD25^+$ Tregs may inhibit the induction and effector activities of both $CD4^+$ and $CD8^+$ (For review see Van Boehmer 2005. Nat. Immunol. 6:338-344). The modes of actions of these Tregs appear to vary and may include control of cytokine secretion (e.g. IL-2 and IFN-γ) from the effector T cells, suppression of cyolytic killing by $CD8^+$ T cells (Chen et al, PNAS 102:419-424), interference with receptor signalling, killing of effector T cells by a perforin dependent mechanism (Piccirillo and Shevach, 2004. Semin. Immunol. 16:81-88) and induction of IL-10 and TGF-β secreting T cells Jonuleit et al, 2002 J. Exp. Med. 196:255-260). Some of the later cells appear to be Tr1 Tregs (Levings et al, 2002 Int. Arch. Allergy Immunol. 129: 262-276) suggesting that $CD4^+CD25^+$ Tregs promote differentiation of other Tregs.

B cell activities can also be regulated by $CD4^+CD25^+$ Tregs. These Tregs have been found to suppress the maturation of autoantibody responses (Fields et al, 2005 J. Immunol. 175:4255-4264), activation and antibody secretion of B cells (Sakaguchi et al, 1995. J. Immunol. 155:1151-1164; Bystry et al, 2001. Nat. Immunol. 2:1126-1132). Killing of B cells involved in antigen presentation by Tregs via Fas/FasL interactions has also been reported (Janssens et al, 2003 J. Immunol. 171:4604-4612).

$CD4^+CD25^+$ Tregs may administer their suppressive effects on bystander cells by regulating the actions of antigen presenting cells. $CD4^+CD25^+$ Tregs may limit the stimulatory capacity of APCs by down-regulating cell surface expression of costimulatory molecules such as CD80 and CD86 and/or preventing maturity (Cederborn et al, 2000. Eur. J. Immunol. 30:1538-1543; Grundstorm et al, 2003. J. Immunol. 170:5008-5017; Taams et al, 2005. Hum. Immunol. 66:222-230; Misra et al, 2004. J. Immunol. 172:4676-4680). In another study, Tregs suppressed myeloid DC maturation, by both blocking costimulatory molecule up-regulation and inhibiting cytokine secretion, which resulted in poor antigen presentation capacity (Hout et al, 2006. J. Immunol. 176: 5293-5298). However, plasmacytoid DCs, that favour TH2 development, were insensitive to the actions of Tregs. Poor antigen presentation by monocytes (Taams et al, 2005. Hum. Immunol. 66:222-230) and monocyte-derived DC driven in the presence of Tregs has also been described (Misra et al, 2004. J. Immunol. 172:4676-4680). Tregs may also exert a negative feedback mechanism on Th1-type responses induced by mature DCs, thereby dampening the development of TH1 responses (Oldenhove et al, 2003. J. Exp. Med. 198: 259-266). In addition, Tregs may regulate a DCs ability to secrete indoleamine 2,3-dioxygenase (IDO), an enzyme that catabolises the depletion of the essential amino acid tryptophan and enhances the production of kynurenine that inhibit T cell proliferation and promote preferential apoptosis of activated T cells (Terness et al, 2002. J. Exp. Med. 196: 447-457). High levels of IDO results in depriving T cells of tryptophan and subsequent apoptosis (Fallarino et al, 2003. Nat. Immunol. 4:1206-1212). It has also been shown that the Tregs restrict contact between DCs and CD4+ helper cells (Tand and Knummel, 2006. Cuur. Opin. Immun. 18: 496-502).

Evidence suggests that CD4+CD25+ Tregs arise from the thymus and may differentiate from CD4+CD25- T cells in the periphery (For review see Huehn, Siegmun and Hamann, 2005. CTMI 293:89-114; Taams and Akbar, 2005 CTMI 293: 115-131; Akbar et al, 2003 Immunology 109:319-325; Bluestone and Abbas, 2003). FoxP3 expression is critical for the development and function of CD4+CD25+ Tregs (for review see Nomura and Sakaguchi, 2005. CTMI 293:287-302). In addition, numerous studies demonstrate that a variety of interactions between CD4+CD25+ Tregs and APCs are required for the development and function of Tregs (Rutella and Lemoli, 2004. Immunol. Lett. 94:11-26; Zheng et al, 2004 J.I. 173:2428; Herman et al, 2004. J. Exp. Med. 199: 1479; Min et al, 2003. J. Immunol. 170:1304-1312; Kumanogoh et al, 2001. J.I. 166:353; Salomom et al, 2000). For example, Tregs fail to develop in mice that lack CD28/B7 interactions. However, CD4+CD25+ Tregs may also affect the differentiation of DC (Min et al, 2003. J. Immunol. 170:1304-1312).

4.2. Analysis of CD4+CD25+ Tregs in PBMC from TV2 Patients

Levels of CD4+CD25+ Tregs were estimated by staining PBMCs with anti-CD4 and -CD25 antibodies, gating on CD4+ cells and setting a strict quadrant in order to only include CD4+CD25$^{hi+}$ cells as a positive readout. The same quadrant was used to evaluate all patients. An example of staining is shown in FIG. 5.

Intracellular staining was also performed to confirm that these cells expressed the transcription factor FoxP3 (FIG. 6).

In the literature, it is generally accepted that levels of CD4+CD25+ Tregs are represented as a percentage of the total CD4+ T cell population. Although there is some debate, CD4+CD25+ Treg cells represent up to a 2 to 10% maximum of CD4+T cells present in peripheral blood of healthy individuals (Maloy and Powrie 2001. Nat. Immunol. 2:816-822; Sakaguchi et al, 2001. Immunol. Rev. 182: 18-32; Gavin and Rudensky, 2003. Curr. Opin. Immunol. 15:690-696; Piccirillo and Shevach, 2004. Seim. Immunol. 16:81-88 Masteller, Tang and Bluestone 2006. Semin. Immunol. 18: 103-110).

Data for TV2-IFL and -FOLFOX patients are tabulated in Table 1. Patients appeared to comprise normal levels of CD4+CD25+ Tregs (up to 2-10%) within their peripheral blood CD4+ T cells prior to chemotherapy.

TABLE 19

Percentage of CD4+CD25+ Tregs in the total CD4+ T cell population.
Means for stage of trial are calculated as the average of each individual time point.

| Patient No. | -2 | 0 | 2 | 4 | 6 | 11 | 13 | 17 | 19 | X+2 | X+4 | X+6 | X+8 | X+10 | X+14 |
|---|---|---|---|---|---|---|---|---|---|---|---|---|---|---|---|
| TV2-002 | 0.99 | | | 1.22 | | 0.66 | | 0.60 | | 0.77 | | | | | 0.87 |
| TV2-003 | 1.20 | | 0.64 | | | 0.67 | | | 0.54 | 0.43 | | | | | 2.29 |
| TV2-012 | 0.87 | | | 0.53 | | 0.29 | | | 0.27 | 0.34 | | | | 0.99 | |
| TV2-014 | | 2.10 | | 2.15 | | | | | 0.98 | 1.84 | | | | | 2.27 |
| TV2-016 | 1.34 | | | 2.41 | | 0.59 | | | 1.06 | 0.95 | | | | | 1.61 |
| TV2-018 | 0.87 | | | 1.27 | | 0.55 | | | 0.14 | 0.37 | | | | | 0.63 |
| TV2-019 | | 3.68 | | 3.80 | | | 3.06 | | 2.90 | 1.98 | | | | | 3.09 |
| IFL Mean | 1.01 | 2.89 | 0.64 | 1.90 | | 0.55 | 3.06 | 0.60 | 0.98 | 0.95 | | | | 0.99 | 1.79 |
| IFL Mean During Trial Stage | | 1.55 | | 1.72 | | | | 0.95 | | | | | 1.32 | | |
| TV2-101 | | 2.63 | | | 1.90 | | 1.25 | | 1.62 | 1.73 | | | 2.85 | | |
| TV2-104 | 1.43 | | | 0.81 | | | | 0.59 | 1.02 | 0.75 | | | 0.85 | | |
| TV2-107 | | 2.44 | | 1.85 | | 2.26 | | | 2.75 | 2.41 | 3.33 | | | | |
| TV2-108 | | | | | 2.38 | 0.86 | 1.59 | | 1.37 | 2.44 | | | 1.46 | | |
| TV2-113 | | 3.27 | | 2.54 | | 1.31 | | 2.59 | | 2.17 | | | 2.33 | | |
| TV2-117 | | 4.40 | | | | | 3.01 | | 3.62 | 4.04 | 5.02 | | | 5.69 | |
| FOLFOX Mean | 1.43 | 2.78 | 4.40 | 1.73 | 2.14 | 1.48 | 1.64 | 2.59 | 2.08 | 2.26 | 4.18 | | 1.87 | 5.69 | |
| FOLFOX Mean During Trial Stage | | 2.44 | | 2.40 | | | 1.66 | | | | | | 2.70 | | |
| | Pre-Trial | | Pre-chemo | | | Chemotherapy | | | | | Post-Chemotherapy | | | | |

The antigen repertoire of CD4+CD25+ Tregs is thought to be as broad as that of naïve T cells, enabling recognition of a wide array of both self- and non-self-antigens, thus allowing control of various immune responses. In order to exert their suppressive capacity, activation of their TCR is required. However, once activated they can suppress antigen non-specifically (Jonuleit et al, 1999. J. Immunol. 193:1285; Thornton and Shevach, 2000. J. Immunol. 164: 183-190; Levings, Sangregorio and Roncarolo, 2001 J. Exp. Med. 193:1295; Yamagiwa et al, 2001 J. Immunol. 166:7282). After TCR-mediated stimulation, the same Tregs suppressed the activation of naïve CD4+ CD25- T cells activated by alloantigens and mitogens (Levings, 2001) Evidence also suggests that peripheral antigen is required for the development, maintenance, or expansion of some Tregs (Mastellar, Tang and Bluestone 2006. Semin. Immunol. 18:103-110).

Both IFL and FOLFOX Treatment Resulted in Depletion of Tregs.

For the IFL patients (n=7) Tregs decreased during chemotherapy in the range of 15-83% compared to pre-chemotherapy time points. For the FOLFOX patients (n=5), the range observed was 31-52% (note patient TV2-108 excluded as there was no pre-chemotherapy time point examined).

Following chemotherapy, levels of Tregs increased compared to the chemotherapy stage, suggesting that the effects of both IFL and FOLFOX are transient. In some patients, levels of Tregs returned to pre-trial levels.

The means of the percentage of CD4+CD25+ Tregs in the CD4+ populations during various stages of the trial has been plotted in FIG. 7. In general, the group of TV2-FOLFOX patients displayed higher levels of CD4+CD25+ Tregs than the group of TV2-IFL patients investigated. Although the levels of Tregs were higher in the TV2-FOLFOX patients (but within the expected range for healthy individuals), than the TV2-IFL patients, the mean changes that were observed throughout the trial in this cell population are similar for both trials. Tregs decreased during chemotherapy by approximately 30% compared to the pre-trial stage. Following chemotherapy, levels of these cells increased but remain within the expected normal range of $CD4^+CD25^+$ Tregs.

Statistical analysis of the data revealed that the percentage of $CD4^+CD25^+$ Tregs in the $CD4^+$ T cell population decreased significantly during chemotherapy compared to pre-chemotherapy in both trials. The geometric mean of Tregs decreased from 1.36 before chemotherapy to 0.68 during IFL treatment (p=0.001). The geometric mean of Tregs decreased from 2.31 prior to chemotherapy to 1.75 during FOLFOX treatment (p=0.0093).

However, levels of Tregs following chemotherapy were not significantly different to that before chemotherapy. The geometric mean of Tregs post-chemotherapy was 1.06 (p=0.2629) and 2.17 (p=0.4923) for the IFL and FOLFOX trials, respectively. This data implies that following depletion of $CD4^+CD25^+$ Tregs during either IFL and FOLFOX treatment, levels of Tregs can increase. As measured by this study, levels of Tregs recovered in the IFL and FOLFOX patients within 14 and 10 weeks following chemotherapy, respectively.

4.3. Conclusions

Both IFL and FOLFOX treatment resulted in a reduction of Tregs.

Although the levels are slightly higher in the FOLFOX group of patients the IFL group, the percentage of $CD4^+CD25^+$ Tregs in the total $CD4^+$ T cell population decreased by 30% during chemotherapy in both TV2 trials.

4.4. Discussion

Patients with a range of different types of cancer have shown an increase in $CD4^+CD25^+$ Tregs in peripheral blood, lymph nodes, tumour ascites and tumour tissue (For review see Nomura & Sakaguci, 2005 Curr. Top. Microbiol. Immunol. 293:287). It has also been shown that increasing tumour burden is associated with an increase in the proportion of Tregs (Liyanage et al, 2002. J. Immunol. 169:2756-2761; Woo et al, 2001. Cancer Res. 61:4766-4772). In this study of TV2 patients, $CD4^+CD25^+$ Tregs appear to be present in the peripheral blood of most patients within the expected normal range (up to 2-10% of the total peripheral blood). However, this study does not address the probability that Tregs have increased in the vicinity of the tumour(s) in these patients, locally suppressing the ability of other immune cells to initiate or sustain a response against inappropriately expressed self or tumour-associated antigen(s).

Both IFL and FOLFOX chemotherapies resulted in a decrease (30%) in the percentage of $CD4^+CD25^+$ Tregs of the total $CD4^+$ T cell population in peripheral blood when measured 1 week after a chemotherapy dose. A number of other chemotherapy treatments have been described where decreased levels of $CD4^+CD25^+$ Tregs in human peripheral blood was observed including cyclophosphamide (Ghirighelli et al, 2004; Eur. J. Immunol. 34: 336-344; Lutsiak et al, 2005. Blood 105:2862-2868), GOLF (gemcitabine [GEM], oxaliplatin, LF and FU; Correale et al, 2005. J. Clin. Oncol. 23:147-162) and temozolomide (Su et al, 2004. J. Clin. Oncol. 4:610-616). ONTAK (recombinant IL-2 diptheria toxin conjugate DAB389IL-2) has also been shown to deplete $CD4^+CD25^+$ Tregs from human PBMCs and allow DC transfected with RNA to prime/boost immune responses (Dannull et al, 2005 J. Clin. Invest. 115: 3623-3633).

In this study of TV2 patients the decrease in $CD4^+CD25^+$ Tregs observed in peripheral blood could reflect a loss due to apoptosis/cell death, or a change in location whereby peripheral blood Tregs have been recruited into tissues or lymph nodes. Since these cells administer their suppressive affects through cell contact, they must migrate to the appropriate sites. Within secondary lymphoid tissues, Tregs must be present to suppress the priming of immune responses and memory responses. Within inflammatory sites, $CD4^+CD25^+$ Tregs must migrate to potentially hamper a variety of possible immune reactions.

More importantly, loss of function of $CD4^+CD25^+$ Tregs may be the crucial factor rather than loss of absolute numbers of Tregs, in order to have the capacity to initiate or sustain immune responses against self and tumour-associated antigens (Coulie and Connerotte, 2005. Curr. Opin. Immunol. 17:320-325). The mechanism by which cyclophosphamide (CY) is able to enhance immune responses by affecting Tregs has recently been elucidated (Lutsiak et al, 2005. Blood 105: 2862-2868). Not only are Treg numbers decreased, CY inhibits their suppressive capacity by increasing apoptosis, decreasing homeostatic proliferation. CY also alters gene expression and down-regulates GITR and FoxP3. The effects of CY on Tregs are transient whereby the absolute numbers of Tregs return to pre-treatment levels 10 days after CY exposure. The transient decrease of Tregs may be essential for successful immunotherapy, whilst maintaining some defence against auto-immunity. It would also be interesting to determine whether the IFL and FOLFOX affect the function of the Tregs in similar or different ways.

Inhibitors of molecules involved in the differentiation, maturation and maintenance of Treg cells, such as FoxP3, may be exploited in order to enhance immune responses to a tumour antigen. Inhibitors of FoxP3 include anti-sense treatment of its' mRNA (Veldman et al, 2006. J. Immunol. 176: 3215-3222) and factors that disrupt its transcription via the transcription factor NFAT, such as cyclosporine A (Mantel et al, 2006 3. Immunol. 3593-360). Interactions of FoxP3 protein with target genes also involves NFAT (Wu et al, 2006. Cell 126:375-387). Dopamine as also been shown to inhibit Treg suppressive activity (Kipnis et al 2004 J. Neurosci. 24:6133-6143)

Although deletion of Treg cells enhances tumour immune responses, complete absence of Treg cells is not sufficient to treat established tumours expressing self antigen (Antony and Restifo, 2002. J. Immunother. 25:202; Antony et al, 2005. J. Immunol. 174:2591-2601). This suggests that tumour regression ideally involves a decrease in Tregs combined with the generation of effector T cells. Hence, strategies that combine vaccination with a factor that causes the loss of Treg and/or Treg function may be ideal for tumour immunotherapy.

The study of frozen PBMCs from TV2 patients measured only one type of regulatory T cell, $CD4^+CD25^+$ Tregs. A decrease of 30% was observed during chemotherapy in both trials. $CD4^+$ $CD25^{hi+}$ Tregs may originate from the thymus (natural Tregs) or from the periphery (adaptive Tregs; Bluestone and Abbas, 2003). There is no evidence to suggest that Tregs that suppress immune responses against self antigens arise only from the thymus, or only from the periphery. Ablation of thymic-derived Tregs may result in a decrease of Tregs for a few weeks before they can be regenerated from the appropriate bone marrow precursors.

Appendix One: Patient Demographics

TV2 FOLFOX

| Subject Number | Age (Years at trial entry) | Gender | Race |
|---|---|---|---|
| 101 | 68 | Male | White |
| 102 | 65 | Male | White |
| 103 | 65 | Male | White |
| 104 | 59 | Female | White |
| 105 | 56 | Male | White |
| 106 | 54 | Female | White |
| 107 | 67 | Male | White |
| 108 | 59 | Male | White |
| 109 | 66 | Male | Black |
| 110 | 55 | Male | White |
| 111 | 65 | Female | White |
| 112 | 72 | Female | White |
| 113 | 47 | Male | Asian |
| 114 | 56 | Female | White |
| 115 | 62 | Male | White |
| 116 | 49 | Female | White |
| 117 | 51 | Male | White |

TV2 IFL

| Subject Number | Age (Years at trial entry) | Gender | Race |
|---|---|---|---|
| 001 | 60 | Female | White |
| 002 | 65 | Male | White |
| 003 | 66 | Male | White |
| 004 | 55 | Male | Black |
| 005 | 58 | Male | White |
| 006 | 66 | Male | White |
| 007 | 62 | Female | White |
| 008 | 68 | Female | White |
| 009 | 64 | Female | White |
| 010 | 49 | Female | White |
| 011 | 66 | Male | White |
| 012 | 64 | Male | White |
| 013 | 65 | Female | White |
| 014 | 73 | Male | White |
| 015 | 46 | Male | White |
| 016 | 63 | Male | White |
| 017 | 62 | Male | White |
| 018 | 61 | Male | White |
| 019 | 62 | Male | White |

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method of treating cancer in a patient, said method comprising:
    determining a baseline level of peripheral blood $CD4^+CD25^+$ Tregs of the patient,
    administering chemotherapy to the patient,
    determining a level of peripheral blood $CD4^+CD25^+$ Tregs of the patient during or after the chemotherapy, and
    immunizing the patient with an antigen when the patient has a reduced level of peripheral blood $CD4^+CD25^+$ Tregs,
    wherein the antigen is 5T4.

2. The method of claim 1, comprising immunizing the patient with the antigen prior to administering the chemotherapy.

3. The method of claim 1, comprising immunizing the patient with the antigen during a same time frame as administering the chemotherapy.

4. The method of claim 1, comprising immunizing the patient with the antigen after the chemotherapy.

5. The method of claim 1, wherein the chemotherapy is FOLFOX (5-fluorouracil, leucovorin and oxaliplatin) or IFL (irinotecan, 5-fluorouracil and leucovorin).

* * * * *